US011155827B2

(12) United States Patent
Li et al.

(10) Patent No.: US 11,155,827 B2
(45) Date of Patent: *Oct. 26, 2021

(54) METHODS FOR GENERATING TRANSGENIC PLANTS

(71) Applicant: SYNGENTA PARTICIPATIONS AG, Basel (CH)

(72) Inventors: Xianggan Li, Research Triangle Park, NC (US); Sivamani Elumalai, Research Triangle Park, NC (US)

(73) Assignee: Syngenta Participations AG, Basel (CH)

(*) Notice: Subject to any disclaimer, the term of this patent is extended or adjusted under 35 U.S.C. 154(b) by 125 days.

This patent is subject to a terminal disclaimer.

(21) Appl. No.: 16/558,380

(22) Filed: Sep. 3, 2019

(65) Prior Publication Data

US 2019/0390206 A1 Dec. 26, 2019

Related U.S. Application Data

(63) Continuation of application No. 14/298,328, filed on Jun. 6, 2014, now Pat. No. 10,443,063.

(60) Provisional application No. 61/833,607, filed on Jun. 11, 2013.

(51) Int. Cl.
*C12N 15/82* (2006.01)
(52) U.S. Cl.
CPC ..... *C12N 15/8209* (2013.01); *C12N 15/8205* (2013.01); *C12N 15/8201* (2013.01)
(58) Field of Classification Search
CPC .................... C12N 15/8205; C12N 15/8209
See application file for complete search history.

(56) References Cited

U.S. PATENT DOCUMENTS

| 7,575,917 | B2 | 8/2009 | Gilbertson et al. | |
|---|---|---|---|---|
| 8,053,636 | B2* | 11/2011 | Van Thournout | C12N 15/8271 |
| | | | | 800/285 |
| 8,592,650 | B2 | 11/2013 | Mason et al. | |
| 10,443,063 | B2* | 10/2019 | Li | C12N 15/8201 |
| 2006/0191038 | A1 | 8/2006 | Flasinkski | |
| 2009/0260103 | A1* | 10/2009 | Charng | C12N 15/8265 |
| | | | | 800/278 |
| 2010/0319089 | A1 | 12/2010 | Azhakanandam | |
| 2011/0047651 | A1 | 2/2011 | Engler et al. | |
| 2011/0077223 | A1 | 3/2011 | Conner et al. | |
| 2012/0021506 | A1 | 1/2012 | Nuccio et al. | |
| 2012/0131699 | A1 | 5/2012 | Ye et al. | |
| 2012/0180162 | A1 | 7/2012 | Patterson et al. | |
| 2012/0278950 | A1* | 11/2012 | Que | C12N 15/8246 |
| | | | | 800/294 |
| 2012/0324600 | A1 | 12/2012 | Hipskind | |
| 2013/0007908 | A1* | 1/2013 | Huang | A01N 65/44 |
| | | | | 800/272 |
| 2013/0074403 | A1 | 3/2013 | Lee et al. | |

FOREIGN PATENT DOCUMENTS

WO 1999032642 A2 7/1999

OTHER PUBLICATIONS

Zhao et al (Co-transformation of gene expression cassettes via particle bombardment to generate safe transgenic plant without any unwanted DNA. In Vitro Cell. Dev. Biol.—Plant 43:328-334, 2007). (Year: 2007).*
Ye et al., "Enhanced production of single copy backbone-free transgenic plants in multiple crop species using binary vectors with a pRi replication origin in Agrobacterium tumefaciens" Transgenic Research (2011) 20:773-786.
Lowe et al., "Enhanced single copy integration events in corn via particle bombardment using low quantities of DNA" Transgenic Research (2009) 18:831-840.
Matzke et al., "Epigenetic silencing of plant transgenes as a consequence of diverse cellular defence responses," Cell. Mol. Life Sci. 54 (1998) 94-103.
Meyer et al., "Homology-Dependent Gene Siliencing in Plants," Annu. Rev. Plant Physiol. Plant Mol. Biol. (1996) 47:23-48.
Hanson et al., "A simple method to enrich an Agrobacterium-transformed population for plants containing only T-DNA sequences," The Plant Journal (1999) 19(6):727-734.
Ye et al., "Plant development inhibitory genes in binary vector backbone improve quality event efficiency in soybean transformation," Transgenic Res. (2008) 17:827-838.
Jackson et al., "Comparison of Agrobacterium and particle bombardment using whole plasmid or minimal cassette for production of high-expressing, low-copy transgenic plants," Transgenic Res. (2013) 22:143-151.
Sugita et al., "A transformation vector for the production of marker-free transgenic plants containing a single copy transgene at high frequency," The Plant Journal (2000) 22(5):461-469.
Oltmanns et al., "Generation of Backbone-Free, Low Transgene Copy Plants by Launching T-DNA from the Agrobacterium Chromosome," Plant Physiology (2010) 152:1158-1166.
Fu et al., "Linear transgene constructs lacking vector backbone sequences generate low-copy-number transgenic plants with simple integration patterns," Transgenic Research (2000) 9:11-19.
Srivastava et al., "Single-copy transgenic wheat generated through the resolution of complex integration patterns," Proc. Natl. Acad. Sci. USA (1999) 96:11117-11121.
Kondrak et al., "Generation of Marker- and Backbone-Free Transgenic Potatoes by Site-Specific Recombination and a Bi-Functional Marker Gene in a Non-Regular One-Border Agrobacterium Transformation Vector," Transgenic Research (2006) 15:729-737.

(Continued)

*Primary Examiner* — Ashley K Buran
*Assistant Examiner* — Wayne Zhong
(74) *Attorney, Agent, or Firm* — Dale Skalla

(57) ABSTRACT

This invention provides a method for generating transgenic plants with a low copy number. Plant cells are transformed with polynucleotides containing transcriptional cassettes designed to trigger silencing of a gene which is essential for the plant cell to survive the transformation and regeneration process. The present invention enables the recovery of an increased number of transgenic plants which have only one copy of each desired transcriptional cassette.

10 Claims, 13 Drawing Sheets

Specification includes a Sequence Listing.

(56) References Cited

OTHER PUBLICATIONS

Kuraya et al., "Suppression of transfer of non-T-DNA 'vector backbone' sequences by multiple left border repeats in vectors for transformation of higher plants mediated by Agrobacterium tumefaciens," Molecular Breeding (2004) 14:309-320.

Notification of Transmittal of the International Search Report and the Written Opinion of the International Searching Authority in corresponding PCT Application No. PCT/US2014/041270 dated Jan. 13, 2015 (24 pages).

Stoykova et al., "PMI (manA) as a nonantibiotic selectable marker gene in plant biotechnology", Plant Cell, Tissue and Organ Culture, 2011, vol. 105, pp. 141-148.

* cited by examiner

METHODS FOR GENERATING TRANSGENIC PLANTS

CROSS REFERENCE TO RELATED APPLICATIONS

This application is a continuation of U.S. application Ser. No. 14/298,328, filed on Jun. 6, 2014, which claims priority to U.S. Provisional Application No. 61/883,607, filed on Jun. 11, 2013, the entire contents of each of which are incorporated herein by reference.

SEQUENCE LISTING

This application is accompanied by a sequence listing entitled 80253-US-REG-C-NAT-1_SeqListing.txt, created Aug. 30, 2019, which is approximately 102,825 bytes in size. This sequence listing is incorporated herein by reference in its entirety. This sequence listing is submitted herewith via EFS-Web, and is in compliance with 37 C.F.R. § 1.824(a)(2)-(6) and (b).

FIELD OF THE INVENTION

The present invention relates generally to the field of plant biotechnology. More specifically, the present invention relates to producing an increased number of transformed plants having a single copy of each transcriptional cassette of interest. Specifically, the invention includes compositions and methods for silencing or significantly reducing the expression of a gene which is essential for the plant cell to survive the transformation and regeneration process, so that an increased number of transgenic plants with a single copy of each transcriptional cassette of interest, relative to plants having multiple copies, are generated.

BACKGROUND

Cultivated crops such as maize, soybean, and cotton have substantial commercial value throughout the world. The development of scientific methods useful in improving the quantity and quality of important crops is, therefore, of significant commercial interest. Significant effort has been expended to improve the quality of cultivated crop species by conventional plant breeding. Conventional means for crop and horticultural improvements utilize selective breeding techniques to identify plants having desirable characteristics. However, such selective breeding techniques have several drawbacks, namely that these techniques are often labor intensive and result in plants that often contain heterogeneous genetic components that may not always result in the desirable trait being passed on from the parent plants. Advances in molecular biology have allowed mankind to modify the germplasm of animals and plants. Genetic engineering of plants entails the isolation and manipulation of genetic material (typically in the form of DNA) and the subsequent introduction of that genetic material into a plant's genome. Such technology has the capacity to deliver crops or plants having various improved economic, agronomic or horticultural traits.

The introduction of the foreign genetic material into a plant's genome is typically performed through one of two ways, although other ways are known to those skilled in the art. The first is biolistic particle bombardment, whereby the foreign DNA, or "transgene," is coated onto a metal particle, which is then shot into plant tissue. Some of that foreign genetic material is taken up by the plant cells, which are thereby "transformed." The second method is by Agrobacterium-mediated transformation, which involves exposing plant cells and tissues to a suspension of Agrobacterium cells that contain certain DNA plasmids. In both methods, the foreign DNA typically encodes for a selectable marker that permits transformed plant cells to grow in the presence of a selection agent, for example an antibiotic or herbicide. These cells can be further manipulated to regenerate into whole fertile transgenic plants.

For both Agrobacterium-mediated transformation and biolistic transformation, there is a possibility of the insertion of more than one copy of the transgene in a plant genome. For biolistic transformation, it is known in the art that a significant percentage of transgenic events contain more than one copy of the transgene. For Agrobacterium-mediated transformation, the transformation method utilizes a T-DNA (transferred DNA) that incorporates the genetic elements of a transgene and transfers those genetic elements into the genome of a plant. The transgene(s) are constructed in a DNA plasmid vector and are usually bordered by an Agrobacterium Ti plasmid right border DNA region (RB) and a left border DNA region (LB). During the process of Agrobacterium mediated transformation, the DNA plasmid is nicked by VirD2 endonuclease at the right and left border regions and the T-DNA region is inserted into the plant genome. The integration of the T-DNA into the plant genome generally begins at the RB and continues to the end of the T-DNA, at the LB. However, it has been found that more than one copy of the T-DNA is frequently inserted into the plant genome. (Tzfira et al 2004, *Trends in Genetics*, 20: 375-383; Windels et al, 2008, "*Agrobacterium tumefaciens*-mediated transformation: patterns of T-DNA integration into the host genome." In *Agrobacterium: from Biology to Biotechnology*, Tzfira, T. and Citovsky, V., Eds. Springer, New York, N.Y.: 441-481, and references within).

It is important to produce transformed plants that have only one copy of the foreign DNA integrated into its genome. Significant resources are directed toward screening transformed plants for the presence of a single copy of the transgene. Methods such as TAQMAN™ analysis and Southern blot analysis are most frequently used. Typically, the initially transformed tissue has gone through several stages of selection and regeneration before it has enough tissue to be sampled for transgene copy number to be accurately ascertained by TAQMAN™ Designing constructs to increase the incidence of a single insertion in the genome would be very valuable.

SUMMARY OF THE INVENTION

The present invention includes a novel method of generating transgenic plant cells, wherein an increased percentage of plant cells incorporate a single copy of the transgene into the plant genome compared to standard methods. The present invention includes a method of generating transgenic plant cells using a plant transformation process, wherein the T-DNA includes a transcriptional cassette that comprises a sequence that is capable of silencing or substantially inhibiting expression of a gene which is essential for the plant cell to survive the transformation and regeneration process.

The invention also provides for a DNA plasmid comprising an Agrobacterium Ti-plasmid which contains one or more T-DNAs, wherein one T-DNA comprises a transcriptional cassette encoding for a polynucleotide which induces silencing of a gene essential for the plant to survive the transformation and regeneration process, such as the silencing of a native gene or a selectable marker.

One aspect of the invention is directed toward a transformation method for generating transgenic plant cells, where an increased percentage of transgenic plant cells carry only one copy of the transcriptional cassettes. This method comprises providing a first transcriptional cassette, wherein the first transcription cassette comprises a selectable marker, providing a second transcriptional cassette comprising a DNA fragment at least 20 polynucleotides in length of a gene which is essential for the plant cell to survive the transformation and regeneration process, and providing at least one transcriptional cassette comprising a trait gene. Next, the cassettes are transformed into a plurality of plant cells to produce a plurality of transgenic plant cells, and the transgenic plant cells are selected for in the presence of a selection agent using the selectable marker. The selected transgenic plant cells are then grown into transgenic tissue. The transgenic plant cells which incorporated at least two copies of the transcriptional cassette comprising a DNA fragment at least 20 polynucleotides in length of a gene which is essential for the plant cell to survive the transformation and regeneration process have reduced survival rates through the transformation and regeneration process. Therefore, an increased percentage of the transgenic cells which do survive the transformation and regeneration process carry only one copy of each transcriptional cassette, compared to methods which do not include the second transcriptional cassette.

The invention includes a transcriptional cassette which comprises at least a DNA fragment of a gene which is essential for the plant cell to survive the transformation and regeneration process, wherein the DNA fragment is at least 20, at least 30, at least 40, at least 50, at least 100, at least 200, at least 500, or at least 1000 polynucleotides of a gene which is essential for the plant cell to survive the transformation and regeneration process, wherein the transcriptional cassette is used with other transcriptional cassettes in a transformation method for generating transgenic plant cells. For this transformation method, an increased percentage of transgenic plant cells carry only one copy of the transcriptional cassettes.

The invention includes a transcriptional cassette which comprises at least a DNA fragment of a gene which is essential for the plant cell to survive the transformation and regeneration process, wherein the DNA fragment is at least 60%, at least 70%, at least 75%, at least 80%, at least 85%, at least 90%, at least 95%, or at least 98% homologous to a gene which is essential for the plant cell to survive the transformation and regeneration process, wherein the transcriptional cassette is used with other transcriptional cassettes in a transformation method for generating transgenic plant cells. For this transformation method, an increased percentage of transgenic plant cells carry only one copy of the transcriptional cassettes.

The invention includes a transcriptional cassette which comprises at least a DNA fragment of a gene which is essential for the plant cell to survive the transformation and regeneration process, wherein the DNA fragment or the gene is selected from the group comprising ZmEPSPS, empty pericarp2, empty pericarp4, defective endosperm18, embryo defective 12, ameiotic1, ZmWHY1, or viviparous-5, wherein the transcriptional cassette is used with other transcriptional cassettes in a transformation method for generating transgenic plant cells. For this transformation method, an increased percentage of transgenic plant cells carry only one copy of the transcriptional cassettes.

The invention includes a transcriptional cassette which produces an RNA molecule of at least 20 polynucleotides in length, wherein the RNA molecule is sufficient in length and identity to induce reduced expression or silencing of a native gene which is essential for the plant cell to survive the transformation and regeneration process, wherein the transcriptional cassette is used with other transcriptional cassettes in a transformation method for generating transgenic plant cells, where an increased percentage of transgenic plant cells carry only one copy of the transcriptional cassettes.

The invention includes a transcriptional cassette which comprises at least a DNA fragment of a gene which is essential for the plant cell to survive the transformation and regeneration process, wherein the gene encodes for a selectable marker which is used for selecting for transgenic plant cells in the presence of the suitable selection agent and wherein the transcriptional cassette is used with other transcriptional cassettes in a transformation method for generating transgenic plant cells, where an increased percentage of transgenic plant cells carry only one copy of the transcriptional cassettes.

Another aspect of the invention is directed toward an *Agrobacterium*-mediated transformation method for generating transgenic plant cells, where an increased percentage of transgenic plant cells carry only one copy of each transcriptional cassette. This method comprises a T-DNA comprising a first transcriptional cassette, wherein the first transcription cassette comprises a selectable marker, a second transcriptional cassette comprising a DNA fragment at least 20 polynucleotides in length of a gene which is essential for the plant cell to survive the transformation and regeneration process, and at least one transcriptional cassette comprising a trait gene. The cassettes are transformed into a plurality of plant cells by an *Agrobacterium*-mediated method, wherein a plurality of transgenic cells are generated.

Transgenic plant cells are selected for in the presence of a selection agent using the selectable marker. The selected transgenic plant cells are then grown into transgenic tissue. The transgenic plant cells which incorporated at least two copies of the transcriptional cassette comprising a DNA fragment at least 20 polynucleotides in length of a gene which is essential for the plant cell to survive the transformation and regeneration process have reduced survival rates through the transformation and regeneration process. Therefore, an increased percentage of the transgenic cells which do survive the transformation and regeneration process carry only one copy of each transcriptional cassette, compared to methods which do not include the second transcriptional cassette.

Another aspect of the invention is directed toward a transformation method for generating transgenic plant cells, where an increased percentage of transgenic plant cells carry only one copy of each transcriptional cassette. This method comprises providing a first transcriptional cassette, wherein the first transcriptional cassette comprises a gene which is a mutated version or homologue of a native gene, and whose expression confers a selectable phenotype, such that transformed cells grown in the presence of a suitable selection agent survive, and non-transformed cells do not survive. This method also comprises providing at least one transcriptional cassette encoding a trait gene. The cassettes are transformed into a plurality of plant cells to produce a plurality of transgenic plant cells, and transgenic plant cells are selected for in the presence of a selection agent using the introduced mutated version or homologue of a native gene as a selectable marker. The selected transgenic plant cells are then grown into transgenic tissue. The transgenic plant cells that incorporated at least two copies of the transcriptional cassette comprising a gene which is a mutated version or homologue of a native gene have reduced survival rates through the transformation and regeneration process. Therefore, an increased percentage of the transgenic cells which do survive the transformation and regeneration process carry only one copy of each transcriptional cassette, compared to methods which do not include the transcriptional cassette comprising a gene which is a mutated version or homologue of a native gene.

Another aspect of the invention is directed toward a transformation method for generating transgenic plant cells, where an increased percentage of transgenic plant cells carry only one copy of each transcriptional cassette. This method comprises providing a first transcriptional cassette, wherein the first transcriptional cassette comprises an EPSPS polynucleotide sequence which is at least 60% homologous to the native EPSPS of the plant cells being transformed and which produces an EPSPS protein whose activity is not inhibited by glyphosate, and providing at least one transcriptional cassette encoding a trait gene. The cassettes are transformed into a plurality of plant cells to produce a plurality of transgenic plant cells, and transgenic plant cells are selected for in the presence of a selection agent using EPSPS as a selectable marker. The selected transgenic plant cells are then grown into transgenic tissue. The transgenic plant cells which incorporated at least two copies of the transcriptional cassette comprising the EPSPS polynucleotide sequence have reduced survival rates through the transformation and regeneration process. Therefore, an increased percentage of the transgenic cells which do survive the transformation and regeneration process carry only one copy of each transcriptional cassette, compared to methods which do not include the transcriptional cassette comprising the EPSPS polynucleotide sequence.

Another aspect of the invention is directed toward a transformation method for generating transgenic plant cells with an increased percentage of the transgenic plant cells carrying only one copy of each transcriptional cassette. This method comprises providing a first transcriptional cassette, wherein the first transcriptional cassette comprises a promoter and at least 20 polynucleotides of an exon of a gene which is essential for the plant cell to survive the transformation and regeneration process. The exon has a mutated start codon, so it cannot promote translation. For this transcriptional cassette, the promoter and exon comprise the 5'regulatory sequence of the transcriptional cassette. The 5' regulatory sequence also comprises a translation initiation sequence, such as a Kozak sequence, at its 3'end. This method also comprises providing at least one transcriptional cassette encoding a selectable marker, providing at least one transcriptional cassette comprising a trait gene, and transforming all the cassettes into a plurality of plant cells to produce a plurality of transgenic plant cells. Transgenic plant cells are selected for in the presence of a selection agent using the selectable marker. The selected transgenic plant cells are then grown into transgenic tissue. The transgenic plant cells which incorporated at least two copies of the transcriptional cassette comprising the 5'-regulatory sequence have reduced survival rates through the transformation and regeneration process. Therefore, an increased percentage of the transgenic cells which do survive the transformation and regeneration process carry only one copy of each transcriptional cassette, compared to methods which do not include the transcriptional cassette comprising the 5' regulatory sequence.

Another aspect of the invention is directed toward a transformation method for generating transgenic plant cells with an increased percentage of the transgenic plant cells carrying only one copy of each transcriptional cassette. This method comprises providing a first transcriptional cassette, wherein the first transcriptional cassette comprises a promoter operably linked to the first exon of a gene which is essential for the plant cell to survive the transformation and regeneration process, which is further operably linked to the first intron or a linker, further operably linked to at least 20 polynucleotides of the second exon of the essential gene. For this transcriptional cassette, the promoter, exon 1, intron 1 or linker, and exon 2 comprise the 5'regulatory sequence of the transcriptional cassette. The 5' regulatory sequence also comprises a translational initiation sequence, such as a Kozak sequence, at its 3'end. In some embodiments, the 5' regulatory sequence is SEQ ID NO: 6. This method also comprises, in addition to providing the first transcriptional cassette, providing a transcriptional cassette encoding a selectable marker, a transcriptional cassette comprising a trait gene, and transforming these cassettes into a plurality of plant cells to produce a plurality of transgenic plant cells. In some embodiments, the first transcriptional cassette comprises SEQ ID NO: 6 operably linked to PMI, and at least one transcriptional cassette comprises a trait gene. Transgenic plant cells are selected for in the presence of a selection agent using the selectable marker. The selected transgenic plant cells are then grown into transgenic tissue. The transgenic plant cells which incorporated at least two copies of the transcriptional cassette comprising the 5'-regulatory sequence have reduced survival rates through the transformation and regeneration process. Therefore, an increased percentage of the transgenic cells which do survive the transformation and regeneration process carry only one copy of each transcriptional cassette, compared to methods which do not include the transcriptional cassette comprising the 5' regulatory sequence.

Another aspect of the invention is directed toward an *Agrobacterium*-mediated transformation method for generating transgenic plant cells with an increased percentage of the transgenic plant cells carrying only one copy each transcriptional cassette of interest. This method comprises providing a first T-DNA polynucleotide comprising all transcriptional cassettes of interest, wherein the first transcriptional cassette comprises a selectable marker and at least one transcriptional cassette comprises a trait gene, and providing a second T-DNA polynucleotide, comprising a transcriptional cassette whose expression induces silencing of the selectable marker. Next, a DNA plasmid for *Agrobacterium*-mediated transformation, comprising the first T-DNA polynucleotide and the second T-DNA polynucleotide, is produced, and *Agrobacterium*-mediated transformation of a plurality of plant cells is performed to produce a plurality of transgenic plant cells. Transgenic plant cells which contain the first T-DNA polynucleotide are selected for in the presence of a selection agent using the selectable marker mentioned above. The selected transgenic plant cells are then grown into transgenic tissue. The transgenic plant cells which incorporated the second T-DNA polynucleotide have reduced survival rates through the transformation and regeneration process. Therefore, an increased percentage of the transgenic cells which do survive the transformation and regeneration process carry only one copy of each transcriptional cassette from the first T-DNA polynucleotide, compared to methods which do not include the second T-DNA polynucleotide.

Another aspect of the invention includes the step of determining the copy number of each transcriptional cassette encoding a selectable marker or a trait gene introduced into the transgenic tissue produced by any of the transformation methods.

Another aspect of the invention includes the step of growing the transgenic plant cell or tissue produced by any of the transformation methods into a fertile plant.

Another aspect of the invention is a transgenic plant, plant cell, or plant tissue comprising a single copy of the transcriptional cassettes of interest produced by any of the transformation methods for generating transgenic plant cells with an increased percentage of the transgenic plant cells carrying only one copy of each transcriptional cassette.

BRIEF DESCRIPTION OF THE SEQUENCES

SEQ ID NO: 1 is the e35S-08-e35S-10-e35S-09-prCMP-xOTPSSUct-01-cZmEPSPSct-01-tNOS-05-01 transcriptional cassette located in binary vector 19096.

SEQ ID NO: 2 is the xOTPSSUct-01-cZmEPSPSct-01-tNOS-05-01 polynucleotide sequence located in binary vector 19094.

SEQ ID NO: 3 is the cZmEPSPS-16-tNOS-05-01 polynucleotide sequence located in binary vector 19095.

SEQ ID NO: 4 is the e35S-08-e35S-10-e35S-09-prCMP-04-xOTPSSUct-01-rZmEPSPSct-01-tNOS-05-01 transcriptional cassette located in binary vector 19120.

SEQ ID NO: 5 is the e35S-08-e35S-10-e35S-09-prCMP-04-OTPSSUct-ΔTG-rZmEPSPSct-02-tNOS-05-01 transcriptional cassette located in binary vector 19122.

SEQ ID NO: 6 is the OsMADS1-05 5' regulatory sequence, which includes the OsMADS1 promoter, first exon, first intron, and part of exon 2. This sequence is referred to as prOsMADS1-05.

SEQ ID NO: 7 is the eFMV-03-e35S-05-prOsMADS1-05-cT6PP-01-tOsMADS1-03 transcriptional cassette located in binary vector 20070.

SEQ ID NO: 8 is the eFMV-03-e35S-05-prOsMADS1-05-tOsMADS1-03 polynucleotide sequence located in binary vector 21099.

SEQ ID NO: 9 is the eFMV-03-e35S-05-prOsMADS2-01-cT6PP-tOsMADS2-01 transcriptional cassette located in binary vector 20096.

SEQ ID NO: 10 is the prUbi1-04-cPMI-01-tNOS-05-01 transcriptional cassette located in binary vector 12678 and in binary vector 12672.

SEQ ID NO: 11 is the prCMP-04-PMIexon-iAtBAF60-01-PMIexon-t35s-08 transcriptional cassette located in binary vector 13481.

SEQ ID NO: 12 is the ZmEPSPS coding sequence with two introduced mutations so that the translated polypeptide is not inhibited by the selection agent glyphosate.

SEQ ID NO: 13 is the coding sequence of the phosphomannose isomerase (PMI) gene.

SEQ ID NO: 14 is the part of SEQ ID NO: 6 which is transcribed, comprising exon 1, intron 1, and part of exon 2 of the OsMADS1 gene.

SEQ ID NO: 15 is the coding sequence of rZmEPSPSct-01, which is found in the transcriptional cassette of SEQ ID NO: 4.

SEQ ID NO: 16 is the transcribed region of SEQ ID NO: 11, comprising a fragment of PMI, the intron iAtBAF60, and a fragment of PMI complementary to the first fragment.

SEQ ID NO: 17 is the eFMV-03-e35S-05-prOsMADS1-05-cPMI-01-tOsMADS1-03 transcriptional cassette located in binary vector 22230.

DETAILED DESCRIPTION OF THE INVENTION

Figure 1:
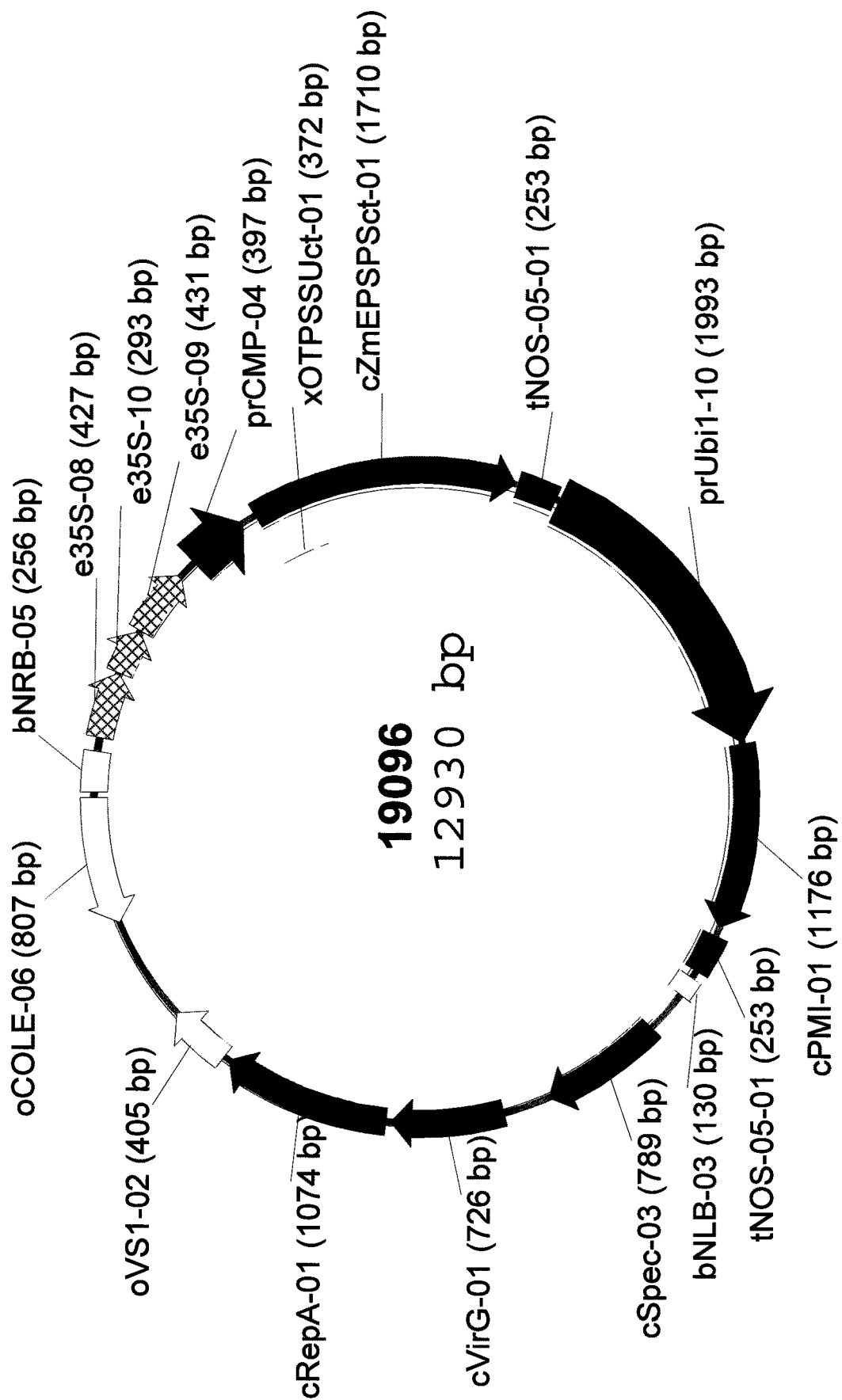
FIG. 1: Plasmid map of binary vector 19096.
Figure 2:
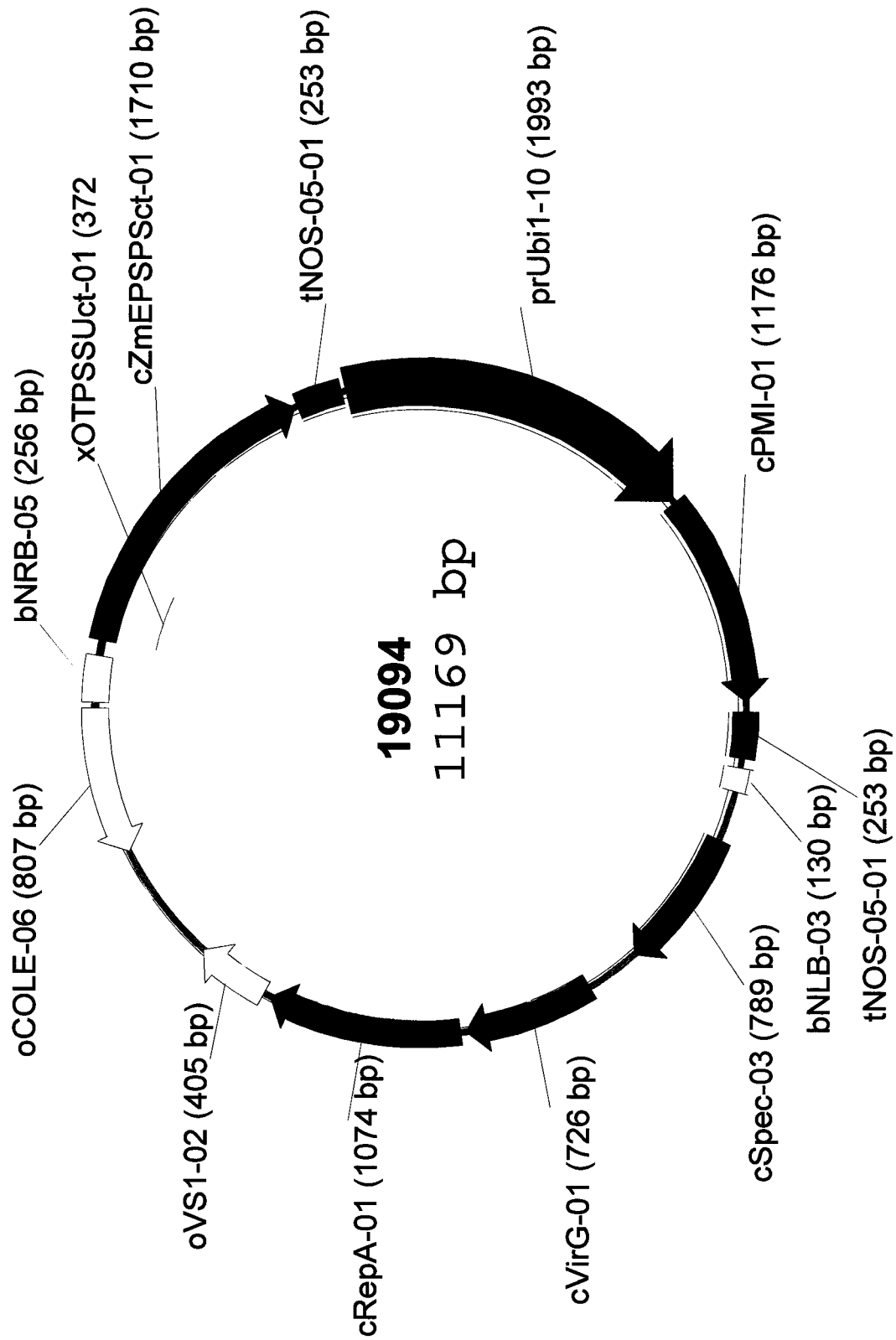
FIG. 2: Plasmid map of binary vector 19094.
Figure 3:
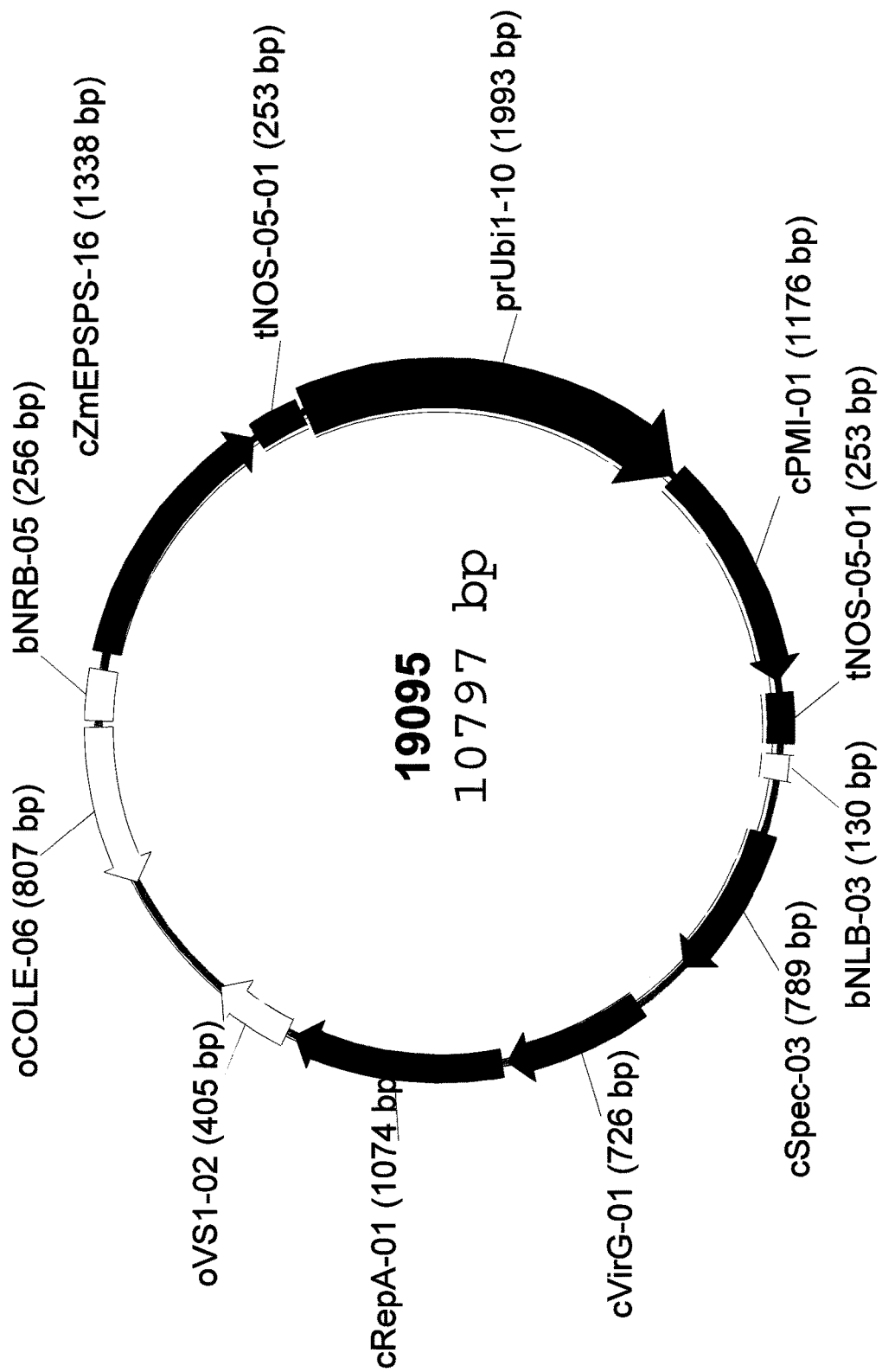
FIG. 3: Plasmid map of binary vector 19095.
Figure 4:
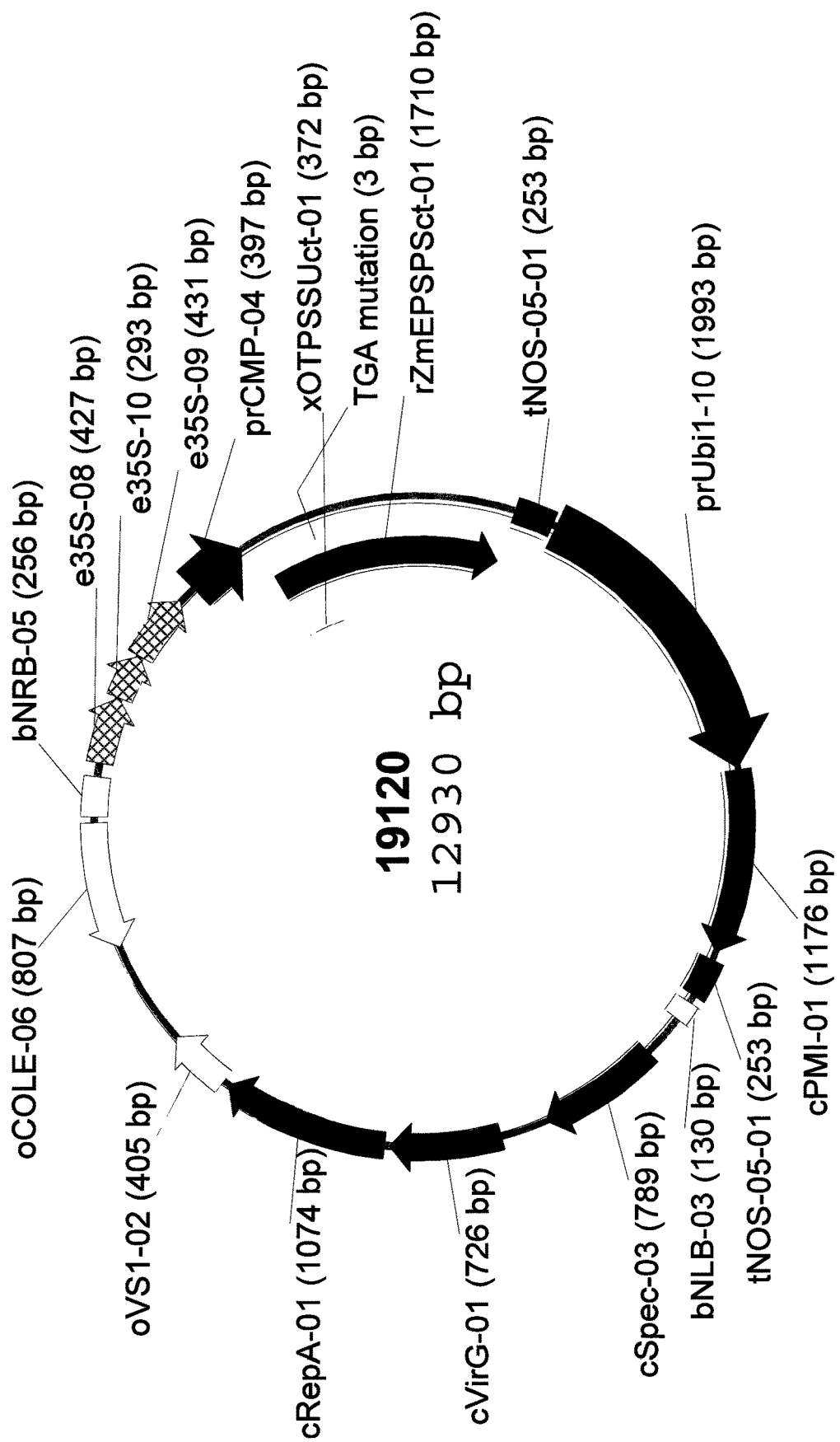
FIG. 4: Plasmid map of binary vector 19120.
Figure 5:
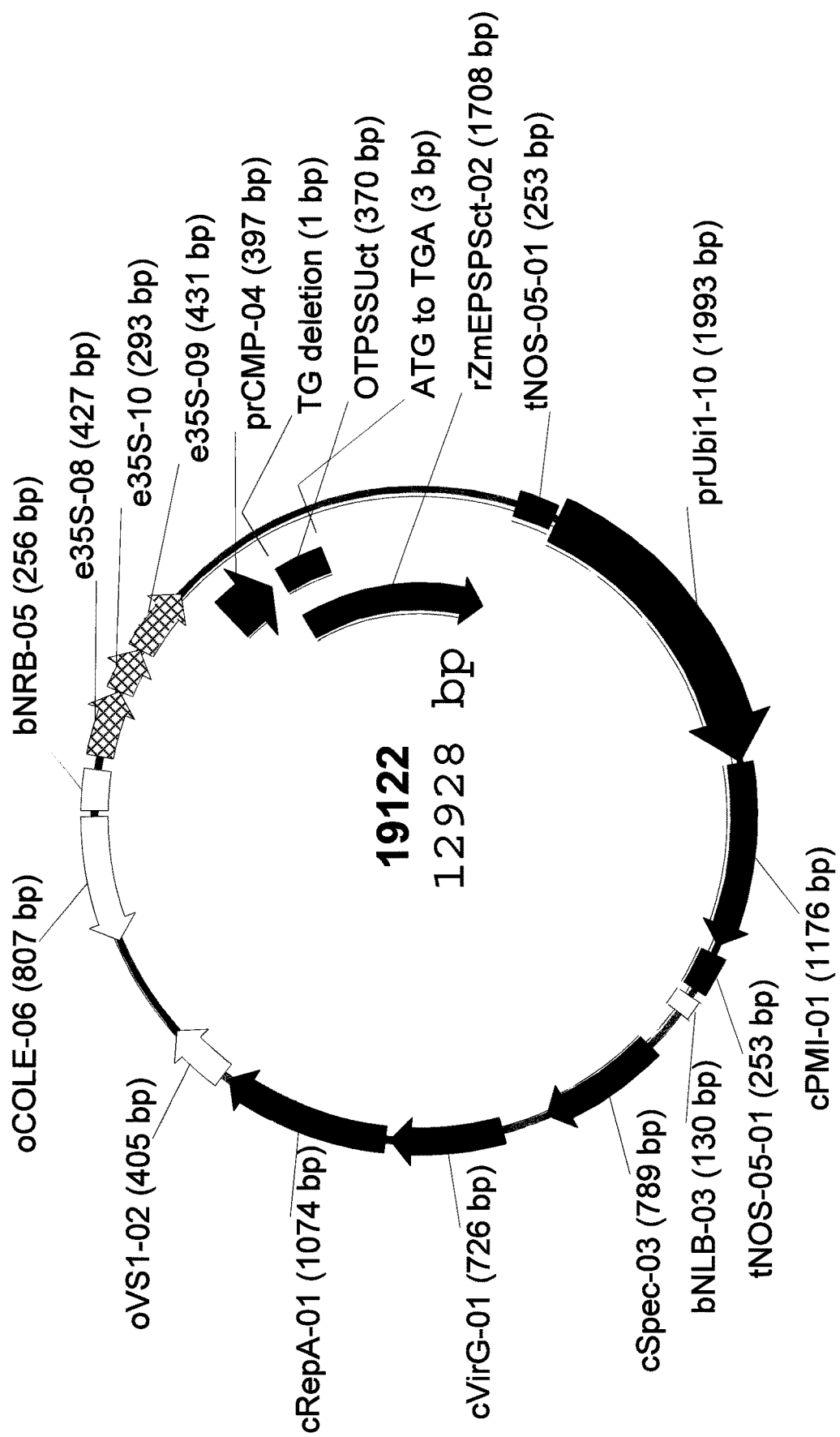
FIG. 5: Plasmid map of binary vector 19122.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

It will be understood that, although the terms "first," "second," etc. may be used herein to describe various elements, these elements should not be limited by these terms. These terms are only used to distinguish one element from another. Thus, a "first" element (e.g., a first promoter sequence) as described herein could also be termed a "second" element (e.g., a second promoter sequence) without departing from the teachings of the present invention.

The term "plant" refers to any plant, particularly to agronomically useful plants (e.g. seed plants), and "plant cell" is a structural and physiological unit of the plant, which comprises a cell wall but may also refer to a protoplast. The plant cell may be in form of an isolated single cell or a cultured cell, or as a part of higher organized units such as for example, a plant tissue, or a plant organ differentiated into a structure that is present at any stage of a plant's development. The promoters and compositions described herein may be utilized in any plant. Examples of plants that may be utilized in contained embodiments herein include, but are not limited to, maize (corn), wheat, rice, barley, soybean, cotton, sorghum, beans in general, rape/canola, alfalfa, flax, sunflower, safflower, millet, rye, sugarcane, sugar beet, cocoa, tea, tropical sugar beet, Brassica spp., cotton, coffee, sweet potato, flax, peanut, clover; vegetables such as lettuce, tomato, cucurbits, cassava, potato, carrot, radish, pea, lentils, cabbage, cauliflower, broccoli, Brussel sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, Indiangrass, Big bluestem grass, Miscanthus and the like. It is recognized that mixtures of plants can be used.

The term "RNA" includes any molecule comprising at least one ribonucleotide residue, including those possessing one or more natural ribonucleotides of the following bases: adenine, cytosine, guanine, and uracil; abbreviated A, C, G, and U, respectively, modified ribonucleotides, and non-ribonucleotides. "Ribonucleotide" means a nucleotide with a hydroxyl group at the 2' position of the D-ribofuranose moiety.

As used herein, the terms and phrases "RNA," "RNA molecule(s)," and "RNA sequence(s)," are used interchangeably to refer to single-stranded RNA, double-stranded RNA, isolated RNA, partially purified RNA, essentially pure RNA, synthetic RNA, recombinant RNA, intracellular RNA, and also includes RNA that differs from naturally occurring RNA by the addition, deletion, substitution, and/or alteration of one or more nucleotides of the naturally occurring RNA.

As used herein, "heterologous" refers to a nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g. present in a different copy number, different location, and/or under the control of different regulatory sequences, than that found naturally in nature.

As used herein, the term "nucleic acid," "nucleic acid molecule," and/or "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the sequence rules for the U.S. Patent and Trademark Office, 37 CFR § 1.821-1.825, and the World Intellectual Property Organization (WIPO) Standard ST.25.

As used herein, the term "gene" is used broadly to refer to any segment of nucleic acid associated with a biological function. Thus, genes include coding sequences and/or the regulatory sequences required for their expression. For example, "gene" refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation, or splicing, of the RNA within the cell to create the mature mRNA that can be translated into a protein.

"Operably linked" refers to the association of nucleic acid sequences on a single nucleic acid fragment so that the function of one is affected by the other. For example, a promoter is operably linked to a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

The terms "complementary" or "complementarity," or "complement" as used herein, refer to the natural binding of polynucleotides under permissive salt and temperature conditions by base-pairing. For example, the sequence "A-G-T" binds to the complementary sequence "T-C-A." The term "complementarity" includes within its meaning two single-stranded molecules that are "partial," in which only some of the nucleotides bind, or where two single-stranded molecules that are complete when total complementarity exists between the single stranded molecules. The degree of complementarity between nucleic acid strands has significant effects on the efficiency and strength of hybridization between nucleic acid strands.

The term "nucleic acid fragment," "DNA fragment" or a fragment of a gene will be understood to mean a nucleotide sequence of reduced length relative to a reference nucleic acid or nucleotide sequence and comprising, consisting essentially of and/or consisting of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of and/or consist of, oligonucleotides having a length of at least about 6, 7, 8, 9, 10, 11, 12, 13, 14, 15, 16, 17, 18, 19, 20, 21, 22, 23, 24, 25, 50, 75, 100, 150, 200, 250, 300, 350, 400, 450, 500, 750, or 1000 consecutive nucleotides of a nucleic acid or nucleotide sequence according to the invention.

An "isolated" nucleic acid of the present invention is generally free of nucleic acid sequences that flank the nucleic acid of interest in the genomic DNA of the organism from which the nucleic acid was derived (such as coding sequences present at the 5' or 3' ends). However, the nucleic acid of this invention can include some additional bases or moieties that do not deleteriously affect the basic structural and/or functional characteristics of the nucleic acid. "Isolated" does not mean that the preparation is technically pure (homogeneous). Thus, an "isolated nucleic acid" is present in a form or setting that is different from that in which it is found in nature and is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. Thus, a nucleic acid found in nature that is removed from its native environment and transformed into a plant is still considered "isolated" even when incorporated into the genome of the resulting transgenic plant. It also includes a recombinant nucleic acid that is part of a hybrid nucleic acid encoding an additional polypeptide or peptide sequence.

The term "isolated" can further refer to a nucleic acid, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. As used herein, the terms "protein" and "polypeptide" are used interchangeably and encompass peptides, unless indicated otherwise. Polypeptides, proteins, and peptides may comprise naturally occurring amino acids, non-naturally occurring amino acids, or a combination of both. The polypeptides, proteins, and peptides may be isolated from sources (e.g., cells or tissues) in which they naturally occur, produced recombinantly in cells in vivo or in vitro or in a test tube in vitro, or synthesized chemically. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., NY, 1987).

The term "transgene" as used herein, refers to any nucleic acid sequence used in the transformation of a plant, animal, or other organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic microorganism, or transgenic animal, is an organism into which a transgene has been delivered or introduced and the transgene can be expressed in the transgenic organism to produce a product, the presence of which can impart an effect and/or a phenotype in the organism. "Transgenic" cells and tissues refer to cells and tissues into which a transgene has been delivered or introduced and the transgene can be expressed in the cells and tissues to produce a product, the presence of which can impart an effect and/or phenotype in the cell or tissue.

Different nucleic acids or polypeptides having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins.

"Expression" refers to the transcription and stable accumulation of mRNA. Expression may also refer to the production of protein.

The terms "transcriptional cassette," "expression cassette," or "cassette" as used herein means a DNA sequence capable of directing expression of a particular nucleotide sequence in an appropriate host cell, comprising a promoter operably linked to the nucleotide sequence which is operably linked to termination signals. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development. The expression cassette also typically comprises sequences required for proper translation of the nucleotide sequence. The coding region usually codes for a protein of interest but may also code for a functional RNA of interest, for example antisense RNA or a nontranslated RNA, in the sense or antisense direction. The transcriptional cassette comprising the nucleotide sequence of interest may be chimeric. "Chimeric" is used to indicate that a DNA sequence, such as a vector or a gene, is comprised of two or more DNA sequences of distinct origin that are fused together by recombinant DNA techniques resulting in a DNA sequence, which does not occur naturally. A transcriptional cassette, expression cassette or cassette can incorporate numerous nucleotide sequences, promoters, regulatory elements, nucleotide sequences of interest, etc.

"Trait gene" refers to transgenes of agronomic interest which provide beneficial agronomic traits to crop plants. Trait genes include but are not limited to genetic elements comprising or that relate to herbicide resistance, increased yield, insect control, fungal disease resistance, virus resistance, nematode resistance, bacterial disease resistance, starch production, modified oils production, high oil production, modified fatty acid content, high protein production, fruit ripening, enhanced animal and human nutrition, biopolymers, environmental stress resistance, pharmaceutical peptides, improved processing traits, improved digestibility, industrial enzyme production, improved flavor, nitrogen fixation, hybrid seed production, and biofuel production.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 of Adh1 was found to be particularly effective and enhanced expression in fusion constructs with the chloramphenicol acetyltransferase gene (Callis et al. 1987, Genes Develop. 1: 1183-1200). In the same experimental system, the intron from the maize bronze 1 gene had a similar effect in enhancing expression. Intron sequences have been routinely incorporated into plant transformation vectors, typically within the non-translated leader.

"Linker" refers to a polynucleotide that comprises the connecting sequence between two other polynucleotides. The linker may be at least 1, 3, 5, 8, 10, 15, 20, 30, 50, 100, 200, 500, 1000, or 2000 polynucleotides in length. A linker may be synthetic, such that its sequence is not found in nature, or it may naturally occur, such as an intron.

"Exon" refers to a section of DNA which carries the coding sequence for a protein or part of it. Exons are separated by intervening, non-coding sequences (introns).

"Transit peptides" generally refer to peptide molecules that when linked to a protein of interest directs the protein to a particular tissue, cell, subcellular location, or cell organelle. Examples include, but are not limited to, chloroplast transit peptides, nuclear targeting signals, and vacuolar signals. To ensure localization to the plastids it is conceivable to use, but not limited to, the signal peptides of the ribulose bisphosphate carboxylase small subunit (Wolter et al. 1988, PNAS 85: 846-850; Nawrath et al., 1994, PNAS 91: 12760-12764), of the NADP malate dehydrogenase (Galiardo et al. 1995, Planta 197: 324-332), of the glutathione reductase (Creissen et al. 1995, Plant J 8: 167-175) or of the R1 protein Lorberth et al. (1998, Nature Biotechnology 16: 473-477).

The term "transformation" as used herein refers to the transfer of a nucleic acid fragment into the genome of a host cell, resulting in genetically stable inheritance. In some particular embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or a combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al 1993, Plant Cell 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hagen and Willmitzer 1988, Nucleic Acids Res 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of nontransformed tissue. Positive selection can be of many types from inactive forms of plant growth regulators that are then converted to active forms by the transferred enzyme to alternative carbohydrate sources that are not utilized efficiently by the nontransformed cells, for example mannose, which then become available upon transformation with an enzyme, for example phosphomannose isomerase, that allows them to be metabolized. Nontransformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90: 217-23), spectinomycin (Svab and Maliga 1993, Plant Mol Biol 14: 197-205), streptomycin (Maliga et al. 1988, Mol Gen Genet 214: 456-459), hygromycin B (Waldron et al. 1985, Plant Mol Biol 5: 103-108), bleomycin (Hille et al. 1986, Plant Mol Biol 7: 171-176), sulphonamides (Guerineau et al. 1990, Plant Mol Biol 15: 127-136), streptothricin (Jelenska et al. 2000, Plant Cell Rep 19: 298-303), or chloramphenicol (De Block et al. 1984, EMBO J 3: 1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. No. 5,561,236); aryloxy alkanoate dioxygenase or AAD-1, AAD-12, or AAD-13 which confer resistance to 2,4-D; genes such as Pseudomonas HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone); and genes conferring resistance to dicamba, such as dicamba monoxygenase (Herman et al. 2005, J Biol Chem 280: 24759-24767 and U.S. Pat. No. 7,812,224 and related applications and patents). Other examples of selectable markers can be found in Sundar and Sakthivel (2008, J Plant Physiology 165: 1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37: 287-96). Finally, other selection systems may use hormone-free medium as the selection agent. One non-limiting example the maize homeobox gene kn1, whose ectopic expression results in a 3-fold increase in transformation efficiency (Luo et al. 2006, Plant Cell Rep 25: 403-409). Examples of various selectable markers and genes encoding them are disclosed in Miki and McHugh (J Biotechnol, 2004, 107: 193-232; incorporated by reference).

In some embodiments of the invention, the selectable marker may be plant derived. An example of a selectable marker which can be plant derived includes, but is not limited to, 5-enolpyruvylshikimate-3-phosphate synthase (EPSPS). The enzyme 5-enolpyruvylshikimate-3-phosphate synthase (EPSPS) catalyzes an essential step in the shikimate pathway common to aromatic amino acid biosynthesis in plants. The herbicide glyphosate inhibits EPSPS, thereby killing the plant. Transgenic glyphosate-tolerant plants can be created by the introduction of a modified EPSPS transgene which is not affected by glyphosate (for example, U.S. Pat. No. 6,040,497; incorporated by reference). Other examples of a modified plant EPSPS which can be used as a selectable marker in the presence of glyphosate includes a P106L mutant of rice EPSPS (Zhou et al 2006, Plant Physiol 140: 184-195) and a P106S mutation in goosegrass EPSPS (Baerson et al 2002, Plant Physiol 129: 1265-1275). Other sources of EPSPS which are not plant derived and can be used to confer glyphosate tolerance include but are not limited to an EPSPS P101S mutant from Salmonella typhimurium (Comai et al 1985, Nature 317: 741-744) and a mutated version of CP4 EPSPS from *Agrobacterium* sp. Strain CP4 (Funke et al 2006, PNAS 103: 13010-13015). Although the plant EPSPS gene is nuclear, the mature enzyme is localized in the chloroplast (Mousdale and Coggins 1985, Planta 163:241-249). EPSPS is synthesized as a preprotein containing a transit peptide, and the precursor is then transported into the chloroplast stroma and proteolytically processed to yield the mature enzyme (della-Cioppa et al. 1986, PNAS 83: 6873-6877). Therefore, to create a transgenic plant which has tolerance to glyphosate, a suitably mutated version of EPSPS which correctly translocates to the chloroplast could be introduced. Such a transgenic plant then has a native, genomic EPSPS gene as well as the mutated EPSPS transgene. Glyphosate could then be used as a selection agent during the transformation and regeneration process, whereby only those plants or plant tissue that are successfully transformed with the mutated EPSPS transgene survive.

A "gene which is essential" or an "essential gene" for the plant cell to survive the transformation and regeneration process may be a selectable marker. It may also be but is not limited to a native, endogeneous gene essential for cell cycle, housekeeping, embryo development, or tissue differentiation. It may also a gene essential for but not limited to DNA or chromosome dynamics, RNA synthesis, RNA modification, protein synthesis, protein modification, metabolism, essential enzymatic pathways, photosynthesis, cell structure, intracellular transport, transcriptional regulation, chromatin remodeling, or essential signaling pathways. Examples of essential genes in maize include but are not limited to empty pericarp2 (Fu et al 2002, Plant Cell 14: 3119-3132), empty pericarp4 (Gutierrez-Marcos et al. 2007, Plant Cell 19: 196-210), defective endosperm18 (Bernardi et al 2012, Plant Physiology 160: 1318-1328), embryo defective 12 (Shen et al. 2013, Plant J DOI: 10.1111/tpj.12161), ameiotic1 (Pawlowski et al. 2009, PNAS: 3603-3608), ZmWHY1 (Prikryl et al 2008, Nucleic Acids Res 36: 5152-5165), g18a/g18b together (Dietrich et al 2005, Plant J 42: 844-61), and viviparous-5 (Hable et al 1998, Mol Gen Genet 257: 167-76). Additional examples of essential maize genes may be found at www.maizegdb.org (Lawrence et al. 2004, Nucleic Acids Research 32: D393-D397). Additional examples of essential plant genes are in Meinke et al., Trends in Plant Sci, 2008, 13: 483-491, herein incorporated by reference.

The term "tissue" refers to a group of living cells which can be but not limited to callus or differentiated into an organ or plant.

The terms "event," "transgenic event," or "transgenic plant event" refers to a transgenic plant produced by transformation and regeneration of a single plant cell with heterologous DNA, such as an expression cassette that includes a gene of interest. The term "event" also refers to progeny produced by the event.

The terms "low copy number" or "low copy" as used herein are in reference to the number of identical copies of a transgene that are present in a transgenic event. An event with a low copy number or low copy has only one complete copy of the T-DNA or introduced polynucleotide of interest incorporated into its genome, with one and only one copy of each transcriptional cassette comprising the T-DNA or introduced polynucleotide of interest and no partial copies. Therefore, the "percent of low copy number" refers to the percentage of transgenic events in a transformation experiment which have incorporated only one complete copy of each transcriptional cassette present in the T-DNA or introduced polynucleotide of interest.

An "interfering RNA" (e.g., siRNA and miRNA) is a RNA molecule capable of post-transcriptional gene silencing, RNA suppression, RNA silencing, and/or decreasing gene expression. Interfering RNAs affect sequence-specific, post-transcriptional gene silencing in animals and plants by base pairing to the mRNA sequence of a target nucleic acid. Thus, the siRNA is at least partially complementary to the silenced gene. The partially complementary siRNA may include one or more mismatches, bulges, internal loops, and/or non-Watson-Crick base pairs (i.e., G-U wobble base pairs).

The terms "gene silencing" "silencing" or "suppression" are used interchangeably to generally describe homology-dependent suppression of transgenes or endogenous nuclear genes. Gene silencing may be transcriptional, when the suppression is due to decreased transcription of the affected genes, or post-transcriptional, when the suppression is due to increased turnover (degradation) of RNA species homologous to the affected genes. (English et al 1996, Plant Cell 8:179-188). This suppression results in substantial and measurable reductions of the amount of the target mRNA available in the cell for binding and decoding by ribosomes. The transcribed RNA can be in the sense orientation to effect what is referred to as co-suppression, in the anti-sense orientation to effect what is referred to as anti-sense suppression, or in both orientations producing a double-stranded RNA to effect what is referred to as RNA interference. A "silenced" gene includes within its definition a gene that is subject to silencing or suppression of the mRNA encoded by the gene.

While the invention is not meant to be limited to any particular mechanism of action or bound by theory, it is possible that the methods disclosed result in an increase in the integration of a single copy of each transcriptional cassette in the transformed plant cell due to an RNA-dependent mechanism, such as co-suppression or RNAi. Methods for reducing or eliminating the expression of a gene in a plant are well known in the art, and any such method may be used in the methods of the present invention. Co-suppression involves transforming plants with a DNA construct comprising a promoter that drives expression in a plant operably linked to at least a portion of a polynucleotide that complements the transcript of the gene of interest, target gene, or other target sequence. The target gene is typically an endogenous, or native gene, but can also be a transgene. Co-suppression involves a heterologous gene sequence expressed in a plant of interest in the sense orientation to suppress the expression of the target gene in the plant. Co-suppression involves a threshold level, where more copies of the heterologous gene increase the likelihood of co-suppression. The heterologous nucleotide sequence is constructed or chosen to have substantial sequence identity to the sequence of the transcript of the target gene, typically greater than about 60% sequence identity, more typically greater than about 80% sequence identity, more typically greater than about 90% sequence identity, and in some instances greater than about 95% sequence identity. Generally, sequences of at least about 20 nucleotides, at least about 30 nucleotides, at least about 40 nucleotides, at least about 50 nucleotides, at least about 100 nucleotides, at least about 200 nucleotides, at least about 300, at least about 400, at least about 450, at least about 500, at least about 550, or greater may be used. This mechanism may act in a threshold-type fashion, where more than one copy of a target gene increases the likelihood of co-suppression occurring. Methods for co-suppression are known in the art. See, for example, Taylor 1997, Plant Cell 9:1245; Jorgensen 1990, Trends Biotech. 8:340-344; Jorgensen et al. 1996, Plant Mol Biol 31:957-973; Johansen and Carrington 2001, Plant Physiol 126:930-938; Broin et al. 2002, Plant Cell 14:1417-1432; Stoutjesdijk et al. 2002, Plant Physiol 129:1723-1731; Yu et al. 2003 Phytochemistry 63:753-763; Flavell 1994, PNAS 91:3490-3496; Finnegan et al. 1994, Bio/Technology 12:883-888; Neuhuber et al. 1994, Mol. Gen. Genet. 244:230-241; and U.S. Pat. Nos. 5,034,323, 5,283,184, and 5,942,657; all of which are herein incorporated by reference.

In some embodiments of the invention, antisense constructions, in which the transgene is complementary to at least a portion of the messenger RNA (mRNA) for the target sequence, may be utilized. Antisense nucleotides are constructed to hybridize with the corresponding mRNA. Modifications of the antisense sequences may be made as long as the sequences hybridize to and interfere with expression of the corresponding mRNA. In this manner, antisense constructs having at least about 70%, at least about 80%, at least about 85% or higher sequence identity to the corresponding sense sequences may be used. Furthermore, portions of the antisense nucleotides may be used to disrupt the expression of the target gene. Generally, sequences of at least about 20 nucleotides, at least about 30 nucleotides, at least about 40 nucleotides, at least about 50 nucleotides, at least about 100 nucleotides, at least about 200 nucleotides, at least about 300, at least about 400, at least about 450, at least about 500, at least about 550, or greater may be used. Antisense methods are known in the art, See, for example, Sheehy et al. 1988, PNAS 85:8805-8809; and U.S. Pat. Nos. 5,107,065; 5,453,566; and 5,759,829, each of which is herein incorporated by reference.

RNA interference (RNAi) can also be used to down-regulate genes. See, generally, Napoli et al. 1990, Plant Cell 2:279-289; U.S. Pat. No. 5,034,323; Sharp 1999, Genes Dev 13:139-141; Zamore et al. 2000, Cell 101:25-33; and Montgomery et al. 1998, PNAS 95:15502-15507. In RNAi, long double-stranded RNAs (dsRNAs), typically >200 nucleotides, can be used to silence the expression of a target gene in a plant. Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme. These siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA. Cleavage of cognate RNA takes place near the middle of the region bound by the siRNA strand.

While the invention is not meant to be limited to any particular mechanism of action or bound by theory, it is possible that the methods disclosed result in an increase in the integration of a single copy of each transcriptional cassette in the transformed plant cell due to an RNA-dependent mechanism, such as co-suppression or RNAi. In some embodiments of the invention, double-stranded RNA (dsRNA) interference may be used. For dsRNA interference, a sense and an antisense RNA molecule that is fully or partially complementary to the sense RNA molecule are expressed in the same cell, resulting in inhibition of the expression of the corresponding messenger RNA. This corresponding mRNA may be a transcript produced from an endogenous native gene or from a second transgene.

The sense and antisense molecules can be expressed from a single or separate expression cassette. Alternatively, multiple plant lines transformed with the dsRNA interference expression cassette or expression cassettes may then be screened to identify plant lines that show the greatest inhibition of gene expression. Methods for using dsRNA interference to inhibit the expression of plant genes are described in Waterhouse et al. 1998, PNAS 95:13959-13964, Liu et al. 2002, Plant Physiol. 129:1732-1743, and WO 99/49029, WO 99/53050, WO 99/61631, and WO 00/49035; each of which is herein incorporated by reference.

In some embodiments of the invention, inhibition of the expression of a gene may be obtained by hairpin RNA (hpRNA) interference or intron-containing hairpin RNA (ihpRNA) interference. A short hairpin RNA (shpRNA) is a sequence of RNA that makes a tight hairpin turn that can be used to silence gene expression. These methods are highly efficient at inhibiting the expression of endogenous genes or other transgenes. See, Waterhouse and Helliwell 2003, Nat Rev Genet 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. Generally, sense and antisense sequences of the base-paired stem region of the molecule of at least about 20 nucleotides, at least about 30 nucleotides, at least about 40 nucleotides, at least about 50 nucleotides, at least about 100 nucleotides, at least about 200 nucleotides, at least about 300, at least about 400, at least about 450, at least about 500, at least about 550, or greater may be used. hpRNA molecules are highly efficient at inhibiting the expression of endogenous genes or other transgenes, and the RNA interference they induce is inherited by subsequent generations of plants. See, for example, Chuang and Meyerowitz 2000, PNAS 97:4985-4990; Stoutjesdijk et al. 2002, Plant Physiol 129:1723-1731; and Waterhouse and Helliwell 2003, Nat Rev Genet 4:29-38. Methods for using hpRNA interference to inhibit or silence the expression of genes are described, for example, in Chuang and Meyerowitz 2000, PNAS 97:4985-4990; Stoutjesdijk et al. 2002, Plant Physiol 129:1723-1731; and Waterhouse and Helliwell 2003, Nat Rev Genet 4:29-38, and U.S. Patent Publication No. 20030175965; each of which is herein incorporated by reference.

Interfering hairpin RNA (ihpRNA) may also be used in the methods of the invention. ihpRNA have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, thus increasing the efficiency of interference. See, for example, Smith et al. 2000, Nature 407: 319-320. Generally, sense and antisense sequences of the base-paired stem region of the molecule of at least about 20 nucleotides, at least about 30 nucleotides, at least about 40 nucleotides, at least about 50 nucleotides, at least about 100 nucleotides, at least about 200 nucleotides, at least about 300, at least about 400, at least about 450, at least about 500, at least about 550, or greater may be used. Methods for using ihpRNA interference to inhibit the expression of endogenous plant genes or other transgenes are described, for example, in Smith et al. 2000, Nature 407:319-320; Wesley et al. 2001, Plant J. 27:581-590; Wang and Waterhouse 2001, Curr Opin Plant Biol 5:146-150; Waterhouse and Helliwell 2003, Nat Rev Genet 4:29-38; Helliwell and Waterhouse 2003, Methods 30:289-295, and U.S. Patent Publication No. 20030180945, each of which is herein incorporated by reference. See also WO 02/00904 where the hpRNA is designed such that the loop region determines the specificity of the RNA interference.

In some embodiments of the invention, RNA interference by expression of a gene encoding a micro RNA (miRNA) may be used. miRNAs are regulatory agents consisting of about 22 ribonucleotides. miRNA are highly efficient at inhibiting the expression of endogenous genes. See, for example Javier et al. 2003, Nature 425: 257-263, herein incorporated by reference. For miRNA interference, the expression cassette is designed to express an RNA molecule that is modeled on an endogenous miRNA gene. The miRNA gene encodes an RNA that forms a hairpin structure containing about a 22-nucleotide sequence that is complementary to the target transcript. For example, a 22-nucleotide sequence is selected from a target transcript sequence and contains 22 nucleotides of the target sequence in sense orientation and 22 nucleotides of a corresponding antisense sequence that is complementary to the sense sequence. See, for example, U.S. Pat. Nos. 8,137,910 and 8,097,710, each of which is incorporated herein by reference.

The following examples are intended solely to illustrate one or more preferred embodiments of the invention and are not to be construed as limiting the scope of the invention.

EXAMPLES

Example 1: Constructs Triggering RNA-Dependent Silencing of Essential Native Gene Increases the Number of Low Copy Transgenic Events For this example, constructs 19096, 19094, 19095, 19120, and 19122 (FIGS. 1, 2, 3, 4, and 5, respectively) were synthesized. Construct 19096 consists of two expression cassettes flanked by right and left borders. The first cassette (SEQ ID NO: 1), comprises a synthetic codon engineered maize double mutant EPSPS (ZmEPSPS or cZmEPSPSct-01) operably linked to a sunflower/maize plastid transit peptide which comprises the sunflower rubisco small subunit transit peptide (xOTPSSUct-01; U.S. Pat. No. 6,040, 497) under the control of three 35S enhancers (e35S), the CMP promoter sequence (prCMP-04) and further operably linked to the nopaline synthase (NOS) 3' end transcription termination and polyadenylation, or terminator, sequence (tNOS, or tNOS-05-01). The second cassette comprises a maize ubiquitin promoter (prUbi1-10) (Christensen et al, 1992, Plant Mol Biol 18: 675) operably linked to a phosphomannose isomerase (PMI) coding sequence (cPMI, or cPMI-01; U.S. Pat. No. 5,767,378, incorporated by reference) further operably linked to the tNOS-05-01 terminator. The prUbi1-10-cPMI-01-tNOS-05-01 transcriptional cassette is also in vectors 19096, 19094, 19095 19120, and 19122, and PMI is used as the selectable marker following transformation of each of the vectors.

The 19096 construct described above served as the control and reference for the remaining constructs. Construct 19094 is the same as 19096, except the cZmEPSPSct-01 cassette in 19094 (which is disclosed as SEQ ID NO: 2) does not contain a promoter or enhancers to drive the expression of the cZmEPSPSct-01 coding sequence. Therefore, the cZmEPSPSct-01 coding sequence was not expected to be expressed. However, if a transcript were to be expressed, the cZmEPSPSct-01 coding region was still operably linked to sunflower/maize xOTPSSUct-01 plastid transit peptide, such that any cZmEPSPSct-01 protein which might be made would target to the chloroplast. Like 19094, the cZmEPSPSct-01 cassette in 19095 also lacks a promoter and enhancers. However, the cZmEPSPS-16 cassette in 19095 (SEQ ID NO: 3) also does not contain the sunflower/maize xOTPS-SUct-01 plastid transit peptide. Therefore, if a transcript were to be expressed, any cZmEPSPS-16 protein which might be made would not target to the chloroplast. The rZmEPSPSct-01 cassette in construct 19120, (SEQ ID NO: 4), is similar to 19096 except that the first ATG start codon of the rZmEPSPSct-01 coding region was changed to a TGA stop codon, resulting in a non-sense RNA that would not translate to the EPSPS enzyme. However, the non-sense RNA could still be translated into a polypeptide and translocated into the plastids by the sunflower/maize xOTPS-SUct-01 plastid transit peptide. The transcriptional cassette which contains rZmEPSPSct-02 in construct 19122, which is disclosed as SEQ ID NO: 5, is similar to construct 19120 except that the OTPSSUct-ΔTG plastid transit peptide has a two nucleotide deletion (ΔTG), resulting in an out-of-frame transit peptide and downstream rZmEPSPSct-02 coding sequence. In this case, the cassette would express a non-sense RNA that would neither translate to a polypeptide nor translocate to the plastids. To summarize, plants transformed with constructs 19094 or 19095 were expected to produce little to no ZmEPSPS mRNA or protein. Plants transformed with constructs 19120 or 19122 produce mutated ZmEPSPS mRNAs which could not be translated into functional EPSPS proteins. Plants transformed with construct 19096 produce both a functional EPSPS mRNA and protein.

Each of these constructs was introduced into *A. tumefaciens* strain LBA4404, which was used for maize transformation. Immature maize embryos were harvested from surface sterilized immature ears 8-12 day after pollination. Embryos were mixed with the suspension of *Agrobacterium* cells harboring the construct of interest, on a co-cultivation medium and allowed to incubate for an additional 5 minutes. Excess *A. tumefaciens* solution was aspirated and embryos were co-cultured with the remaining *A. tumefaciens* at 23° C. for 2-3 days in the dark. Embryos were transferred to culture medium supplemented with timentin (200 mg/L; PhytoTechnology Laboratories®), to kill the remaining *A. tumefaciens* and to promote callus growth of the embryos, and incubated in the dark for 10-14 days. After this stage, the calli are grown in media containing either glyphosate, which is a selection agent for the EPSPS (5-enolpyruvylshikimate-3-phosphate synthase) selectable marker, or a selection agent for the PMI (phosphomannose isomerase) selectable marker, such as mannose. The selection agent is used for selecting the transformed plant cells. After selection, the surviving calluses were transferred to regeneration medium where morphogenesis occurs and tiny shoots develop from the surviving calluses. These tiny shoots were transferred to rooting medium and small putative transgenic plantlets were developed.

DNA from the regenerated plantlets, now referred to as events, was isolated and analyzed using TAQMAN™ qPCR to determine copy number of the introduced PMI gene. TAQMAN™ assays were performed following standard methodology using JumpStart™ Taq ReadyMix™ (Sigma-Aldrich) and the ABI PRISM® 7900HT sequence detection system. Events were considered low-copy, meaning they were likely to have only one copy of the analyzed sequence, if they had a raw TAQMAN™ copy number value of 0.3 to 1.3. Events with a raw TAQMAN™ number above 1.3 were considered medium to high copy number, and are believed to contain more than one copy of the PMI gene. Transformation frequency is calculated as the percentage of transgenic events for a given construct with a given number of immature embryos used for the transformation. For example, if 100 immature maize embryos were initially transformed, and it was eventually determined that 5 of the events contained full or part of the T-DNA, the transformation frequency would be 5%. Table 1 shows the percentage of low copy events (LC %), based on the results of the TAQMAN™ analysis, and the calculated transformation frequency (TF %) for each of the given constructs.

TABLE 1

Copy number analysis and calculated transformation frequency of events transformed with EPSPS constructs

| Construct | Transcriptional Cassette | # Embryos Transformed | LC %* | TF % |
|---|---|---|---|---|
| 19096 | e35S-08-e35S-10-e35S-09-prCMP-04-xOTPSSUct-01-cZmEPSPSct-01-tNOS-05-01 | 943 | 64.20$^a$ | 22.35 |
| 19094 | xOTPSSUct-01-cZmEPSPSct-01-tNOS-05-01 | 536 | 39.68$^b$ | 12 |

TABLE 1-continued

Copy number analysis and calculated transformation frequency of events transformed with EPSPS constructs

| Construct | Transcriptional Cassette | # Embryos Transformed | LC %* | TF % |
|---|---|---|---|---|
| 19095 | cZmEPSPS-16-tNOS-05-01 | 520 | 40.58$^b$ | 26.54 |
| 19120 | e35S-08-e35S-10-e35S-09-prCMP-04-xOTPSSUct-01-rZmEPSPSct-01-tNOS-05-01 | 829 | 57.63$^a$ | 7.12 |
| 19122 | e35S-08-e35S-10-e35S-09-prCMP-04-OTPSSUct-ΔTG-rZmEPSPSct-02-tNOS-05-01 | 515 | 62.07$^a$ | 33.79 |

*Different letters indicate significant differences in a two tailed student's t test (p < 0.05).

Results indicate that constructs 19120 and 19122, which would produce a mutated ZmEPSPS mRNA that would not translate into a functional ZmEPSPS protein, resulted in an event population that had a similar percentage of low copy events as events transformed with 19096, which produced both a functional ZmEPSPS mRNA and protein. The population of events transformed with 19094 or 19095, which lacked a promoter and enhancers to express the ZmEPSPS transgene, have a significantly lower percentage of low copy events. These results show that the ZmEPSPS mRNA is an important factor in increasing the amount of low-copy events.

To determine what the mRNA and protein levels were for ZmEPSPS for each of the constructs, qRT-PCR and quantitative ELISA assays were performed using standard techniques known in the art. To perform qRT-PCR analysis, RNA was extracted from leaf samples followed by DNA digestion. TaqMan assays were selected based on the target of interest which consists of a forward and reverse primer and a FAM-labeled probe that were specific to the target sequence. A species specific, TET-labeled reference target was also employed for each sample for relative expression calculation. One-step RT-PCR reactions were set up in triplicate (3 for endogenous reference gene, 3 for target gene) in 384 well PCR plates. A wild type control and no-RT negative control were included on each plate to test for non-specific amplification and DNA contamination, respectively. Results were captured on a real-time thermocycler, where threshold values are set by the analyzer for each reporter and the resulting data is reported. Relative expression ($2^{-\Delta Ct}$ where $\Delta Ct$=target Ct−reference Ct) was calculated for each sample. Results for qRT PCR were calculated as relative expression level for the gene of interest (the "target") compared to an endogenous reference gene.

For quantitative ELISA, leaf extracts were prepared and were quantitatively analyzed for ZmEPSPS by ELISA (Tjissen, 1985, Practice and Theory of Enzyme Immunoassays) using Protein A purified rabbit anti-rice EPSPS and monoclonal 17 anti-soy EPSPS. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented. Results for ELISAs are expressed as nanogram EPSPS protein per milligram total solution protein (TSP).

TABLE 2

ZmEPSPS RNA and Protein Accumulation

| Construct | Transcriptional Cassette | ZmEPSPS RNA Accumulation | ZmEPSPS Protein Accumulation (ng/mg TSP) |
|---|---|---|---|
| 19096 | e35S-08-e35S-10-e35S-09-prCMP-04-xOTPSSUct-01-cZmEPSPSct-01-tNOS-05-01 | 1957.42 ± 518.08 | 2.45 ± 0.31 |
| 19094 | xOTPSSUct-01-cZmEPSPSct-01-tNOS-05-01 | 3.75 ± 0.20 | 0.00 |
| 19095 | cZmEPSPS-16-tNOS-05-01 | 10.98 ± 0.75 | 0.00 |
| 19120 | e35S-08-e35S-10-e35S-09-prCMP-04-xOTPSSUct-01-rZmEPSPSct-01-tNOS-05-01 | 7120.67 ± 2089.77 | 0.00 |
| 19122 | e35S-08-e35S-10-e35S-09-prCMP-04-OTPSSUct-ATG-rZmEPSPSct-02-tNOS-05-01 | 5056.11 ± 574.57 | 0.00 |

The results of Table 2 confirm that the constructs performed as expected. Very little ZmEPSPS mRNA was produced in events transformed with constructs 19094 or 19095, which lacked a promoter to express the ZmEPSPS transgene. Additionally, no ZmEPSPS protein was detected in events transformed with constructs 19094, 19095, 19120, or 19122.

The results of Table 1 and Table 2 indicate that ZmEPSPS RNA transcripts were needed for an increase in low copy number transformants, but the protein was not. This suggests an RNA-dependent mechanism, such as silencing or co-suppression, may be involved. As stated above, plants have a native, genomic copy of an EPSPS gene, and the ZmEPSPS cassette is introduced transgenically. One scenario consistent with the results, but is not to be construed as limiting the scope of the invention, is where multiple copies of the ZmEPSPS cassette trigger co-suppression of all copies, such that the transformed cell can no longer synthesize the EPSPS enzyme, whereas tissue or plants having a single copy of the ZmEPSPS cassette do not trigger co-suppression. Because EPSPS is essential, a cell wherein EPSPS expression is suppressed would not survive the transformation and regeneration process.

Figure 6:
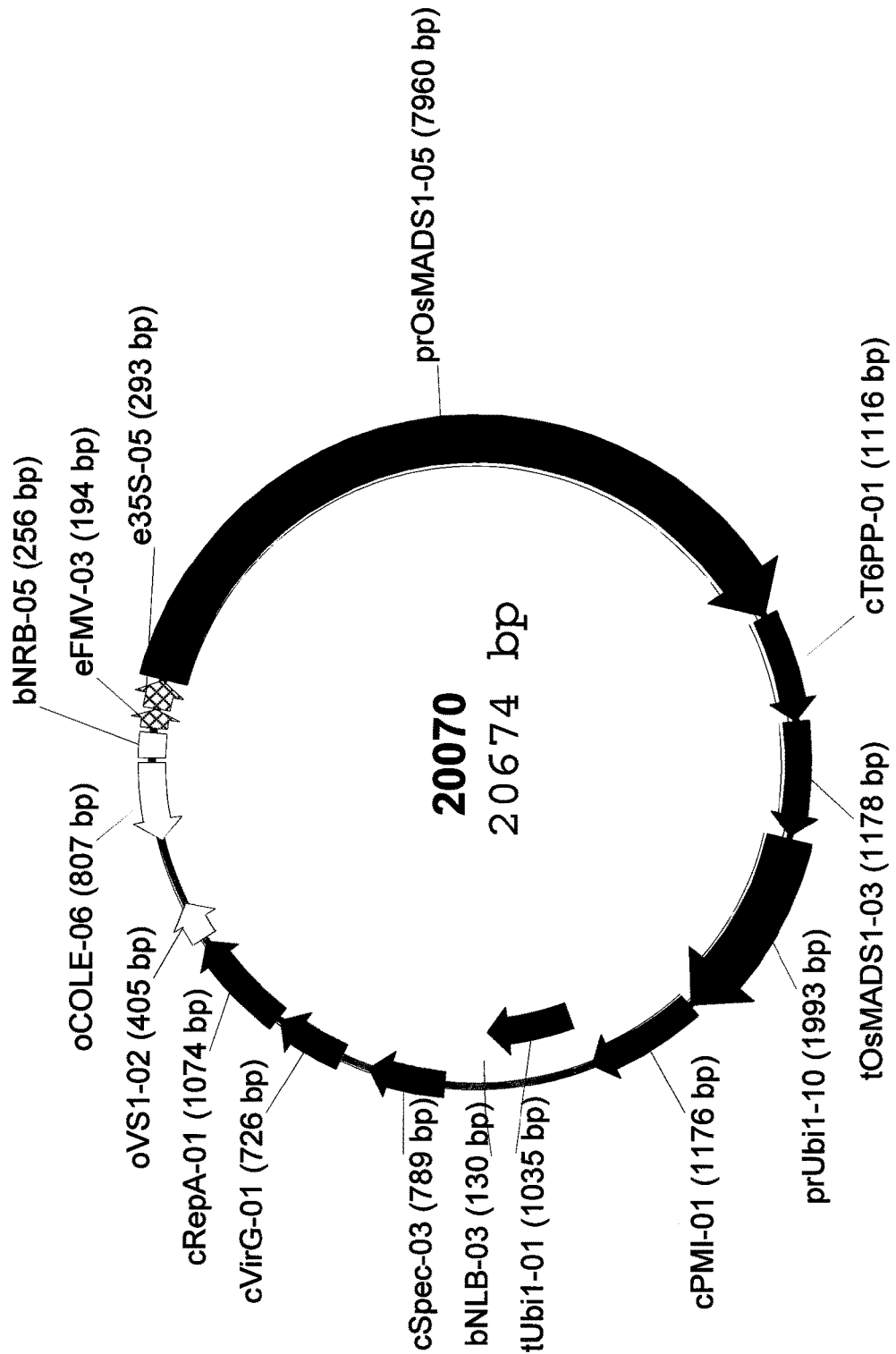
FIG. 6: Plasmid map of binary vector 20070.
Figure 7:
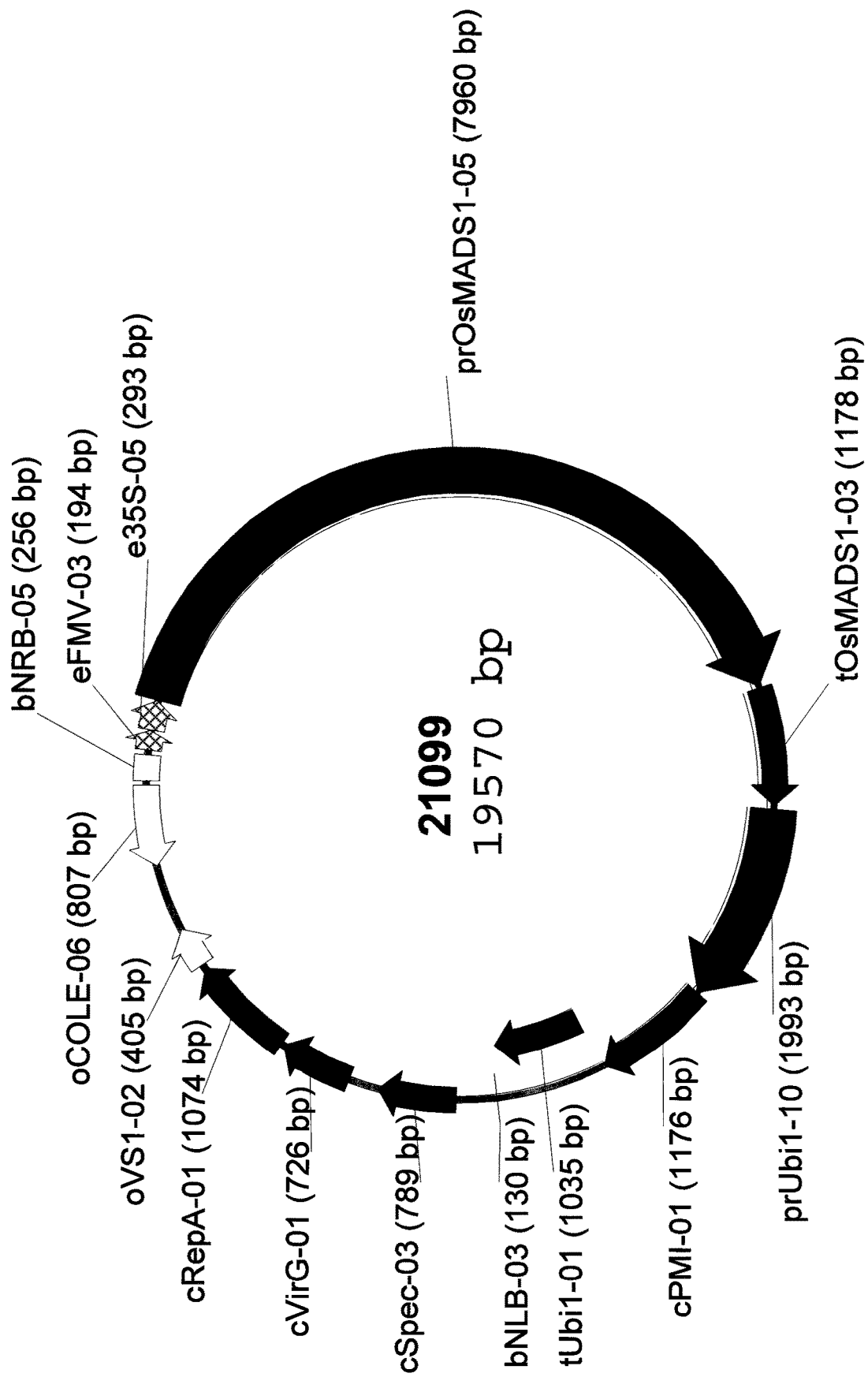
FIG. 7: Plasmid map of binary vector 21099.

Example 2: Constructs Containing OsMADS1 Promoter and 5' Genomic Sequence Increase the Number of Low Copy Transgenic Events For this example, constructs 20070 and 21099 (FIGS. 6 and 7, respectively) were produced. Construct 20070 comprises two expression cassettes between the right and left borders of the T-DNA. The first cassette contains a 7.9 kb promoter based on the OsMADS1 gene, from *Oryza sativa* (GenBank accession AF204063; U.S. Pat. No. 8,129,588). This promoter construct, prOsMADS1-05 (SEQ ID NO: 6), comprises the OsMADS1 promoter, operably linked to the 5'-nontranscribed sequence, exon 1, intron 1 and part of exon 2 of the OsMADS1 gene. Exon 1 contains a mutated ATG to ACA so that no translation initiates from the OsMADS1 exon 1. prOsMADS1-05 contains a maize optimized Kozak sequence at its 3' end to promote translation of a coding sequence. In construct 20070, prOsMADS1-05 is operably linked at the 5' end to enhancers from Figwort mosaic virus (eFMV-03) and the 35S promoter of Cauliflower Mosaic Virus (e35S-05). prOsMADS1-05 is operably linked at its 3' end to the coding sequence of an *Oryza sativa* trehalose-6-phosphate phosphatase (cT6PP-01) gene, further operably linked to the tOsMADS terminator (tOsMADS1-03; U.S. Pat. No. 8,129,588). The eFMV-03-e35S-05-prOsMADS1-05-cT6PP-01-tOsMADS1-03 transcriptional cassette is disclosed as SEQ ID NO: 7. The second expression cassette comprises a maize ubiquitin promoter (prUbi1-10) operably linked to a PMI coding sequence (cPMI-01) further operably linked to a maize ubiquitin 3' end terminator sequence (tUbi1-01). Construct 21099 is similar to construct 20070. However, the first expression cassette comprising the prOsMADS1-05 promoter operably linked to the tOsMADS1-03 terminator does not contain the coding sequence of the rice T6PP (SEQ ID NO: 8). The second cassette is identical to the PMI cassette of 20070, as described above.

Each of the above described constructs was introduced into *A. tumefaciens*, transformed into maize, and transformants were grown on PMI selectable media as described in Example 1. DNA from the regenerated plantlets, now referred to as events, was isolated and analyzed using TAQMAN™ qPCR to determine copy number of the introduced PMI gene, as described in Example 1. Results from copy number analysis and the calculated transformation frequency for each event population transformed with each construct are shown in Table 3. Results were compared to previous results using comparable constructs containing PMI (PMI). These constructs also contain a PMI transcriptional cassette and an additional transcriptional cassette which did not have the OsMADS1-05 promoter.

TABLE 3

Copy number analysis and calculated transformation frequency of events transformed with OsMADS1-05 promoter constructs

| Construct | Transcriptional Cassette | # Events Tested | LC %* | TF % |
|---|---|---|---|---|
| 20070 | eFMV-03-e35S-05-prOsMADS1-05-cT6PP-01-tOsMADS1-03 | 103 | 62.16[a] | 6.788 |
| 21099 | eFMV-03-e35S-05-prOsMADS1-05-tOsMADS1-03 | 235 | 62.65[a] | 19.7 |
| PMI | prUbi1-10-cPMI-01-tNOS-05-01 | 462 | 41.36[b] | 22.5 |

*Different letters indicate significant differences in a two tailed student's t test (p < 0.05).

Results shown in Table 3 indicate that the number of low copy events was not dependent upon the cT6PP-01 coding sequence, suggesting that the OsMADS1-05 promoter plays an important role in the relatively low number of successfully transformed events and the high number of those events which have a single T-DNA insertion. One possible mechanism for this phenomenon is co-suppression of a maize MADS-box homologous gene or genes which play an essential role for the plant cell to survive the transformation and regeneration process. MADS-box genes encode transcription factors which are typically involved in regulating the processes of development and signal transduction in eukaryotic organisms. In addition to flower development, MADS-box gene family members have been shown to be involved in fruit ripening, embryo development, and development of vegetative organs such as root and leaf (Riechmann and Meyerowitz, 1997, Biol Chem 378: 1079-101;

Alvarez-Buylla et al. 2000, Plant J: 4: 457-466; Ng and Yanofsky, 2001, Nat Rev Genet 2: 186-195). While the invention is not meant to be limited to any particular mechanism of action or bound by theory, it is possible that the introduction of the prOsMADS1-05 promoter construct, which is comprised of the OsMADS1 promoter itself operably linked to 5'-nontranscribed sequence, exon 1, intron 1 and part of exon 2 of the OsMADS1 gene, triggers co-suppression of one or more native, genomic maize genes when the prOsMADS1-05 element is present in more than one copy in the transformed plant cell. This proposed mechanism is non-limiting to the invention.

Figure 12:
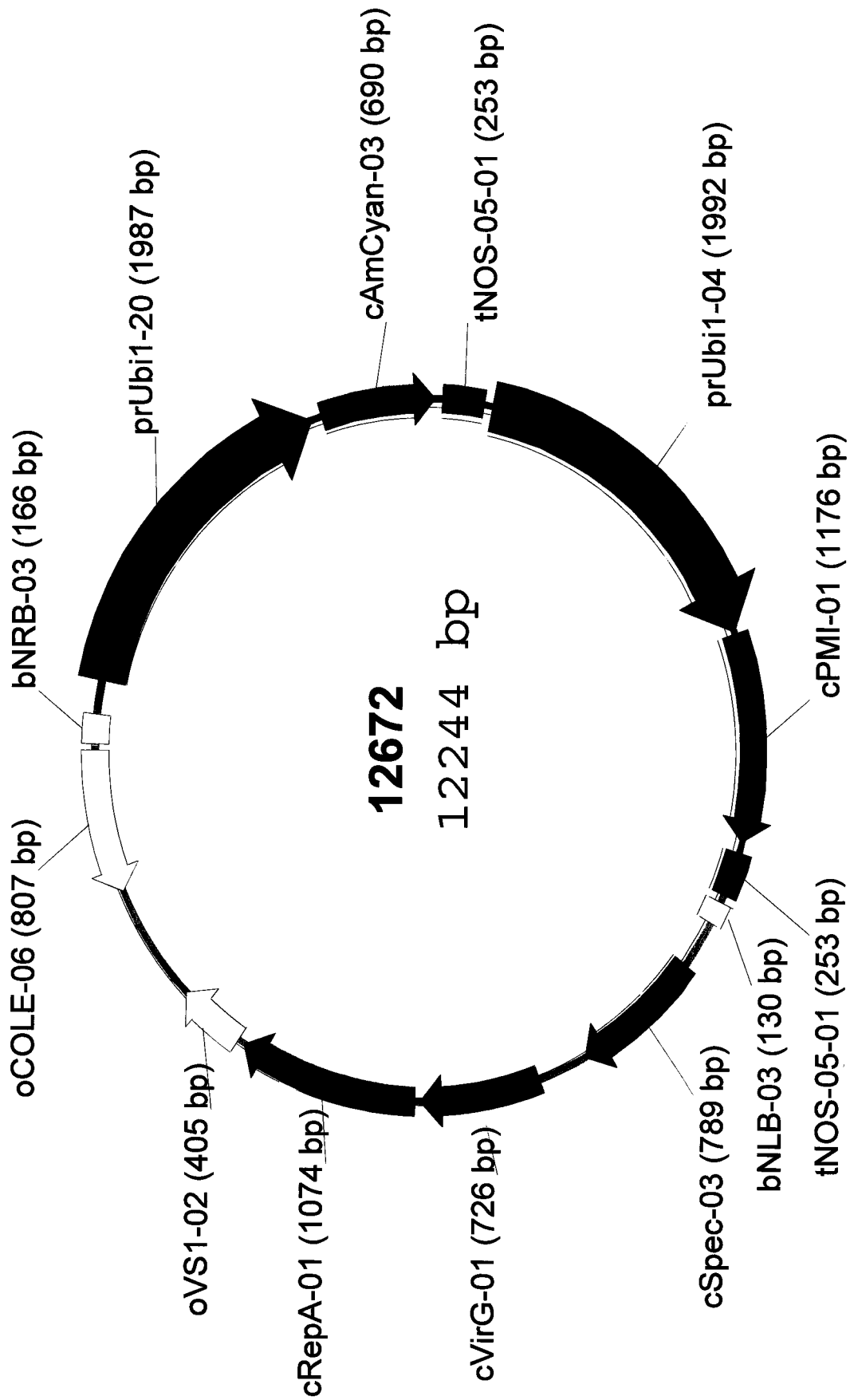
FIG. 12: Plasmid map of binary vector 12672.
Figure 13:
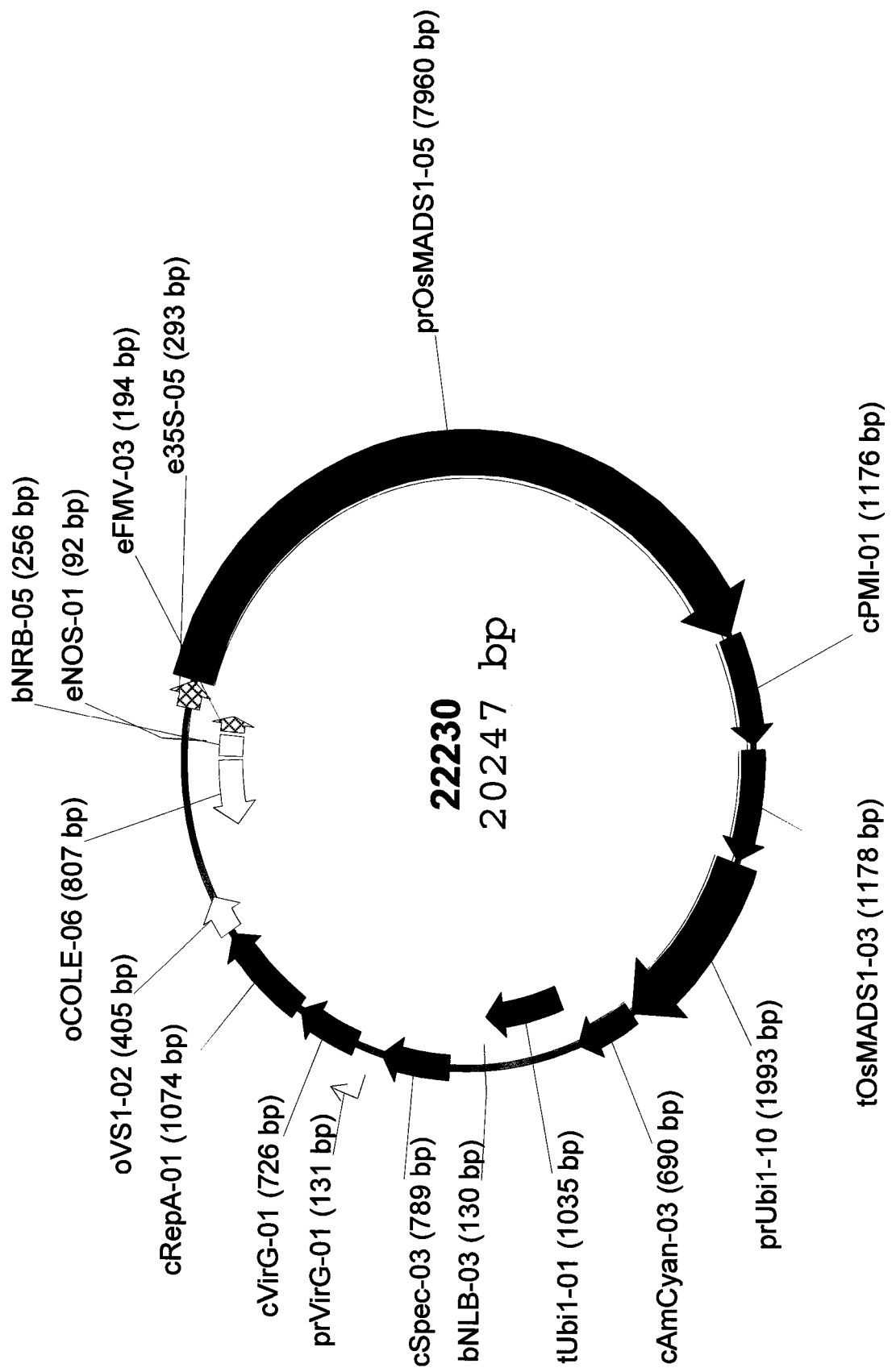
FIG. 13: Plasmid map of binary vector 22230.

To determine if a similar number of low copy events could be obtained if the OsMADS1-05 promoter was operably linked to a different coding sequence, constructs 12672 (FIG. 12) and 22230 (FIG. 13) were designed and tested. Construct 22230 is similar to construct 20070. However, the expression cassette comprising the prOsMADS1-05 promoter is operably linked to the coding sequence of PMI, further operably linked to the tOsMADS1-03 terminator (SEQ ID NO: 17). Additionally, a separate second expression cassette comprises the coding sequence for a cyan fluorescent protein (Clontech Laboratories), operably linked to an ubiquitin promoter at the 5'end and operably linked to an ubiquitin terminator at the 3' end. Construct 12672 comprises two expression cassettes. One cassette comprises an ubiquitin promoter operably linked to the coding sequence of a cyan fluorescent protein (Clontech Laboratories), operably linked to the NOS terminator sequence. The second cassette comprises the prUbi1-04 promoter operably linked to the coding sequence of PMI (cPMI-01), operably linked to the tNOS-05-01 terminator sequence (SEQ ID NO: 10).

Figure 8:
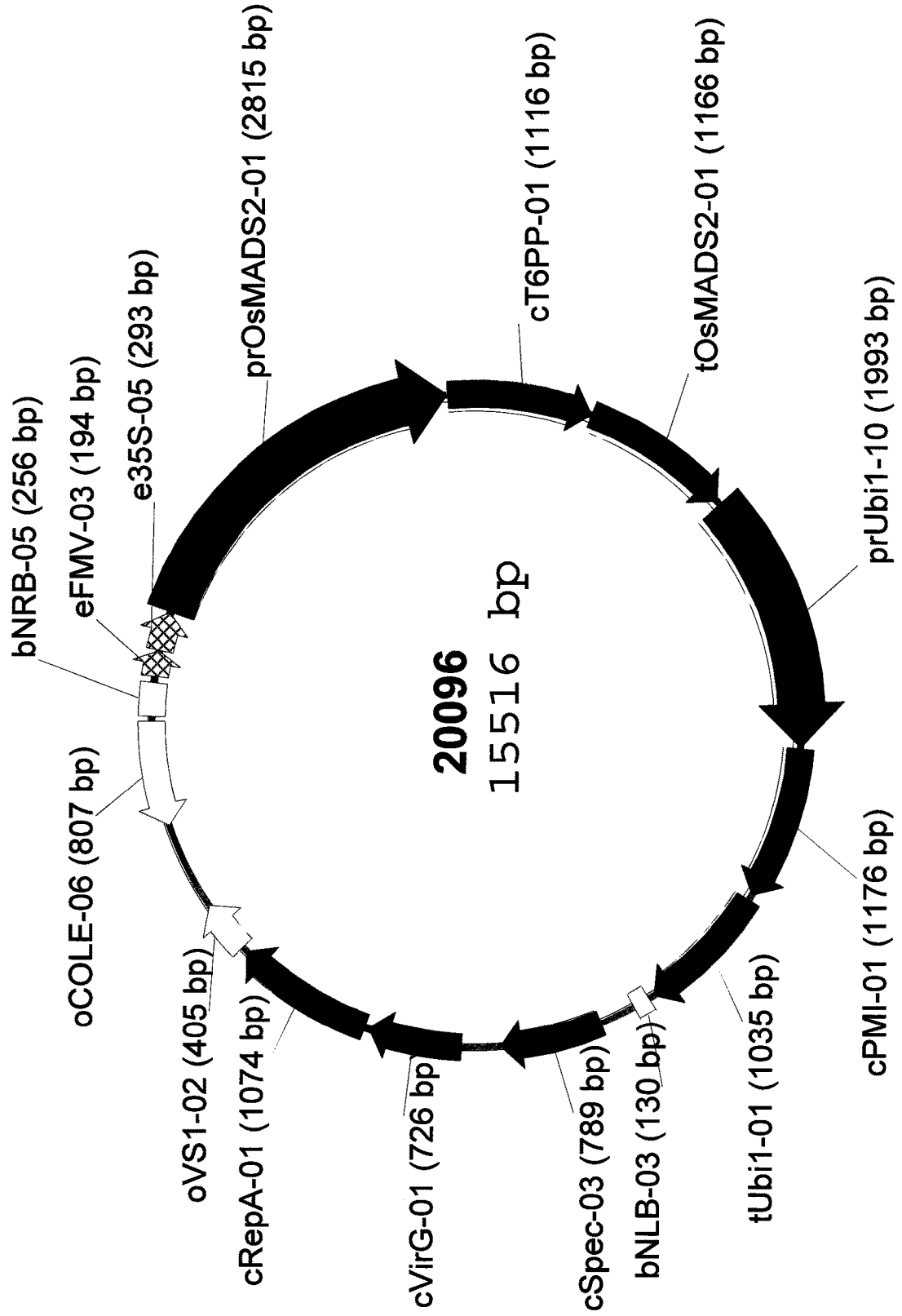
FIG. 8: Plasmid map of binary vector 20096.
Figure 9:
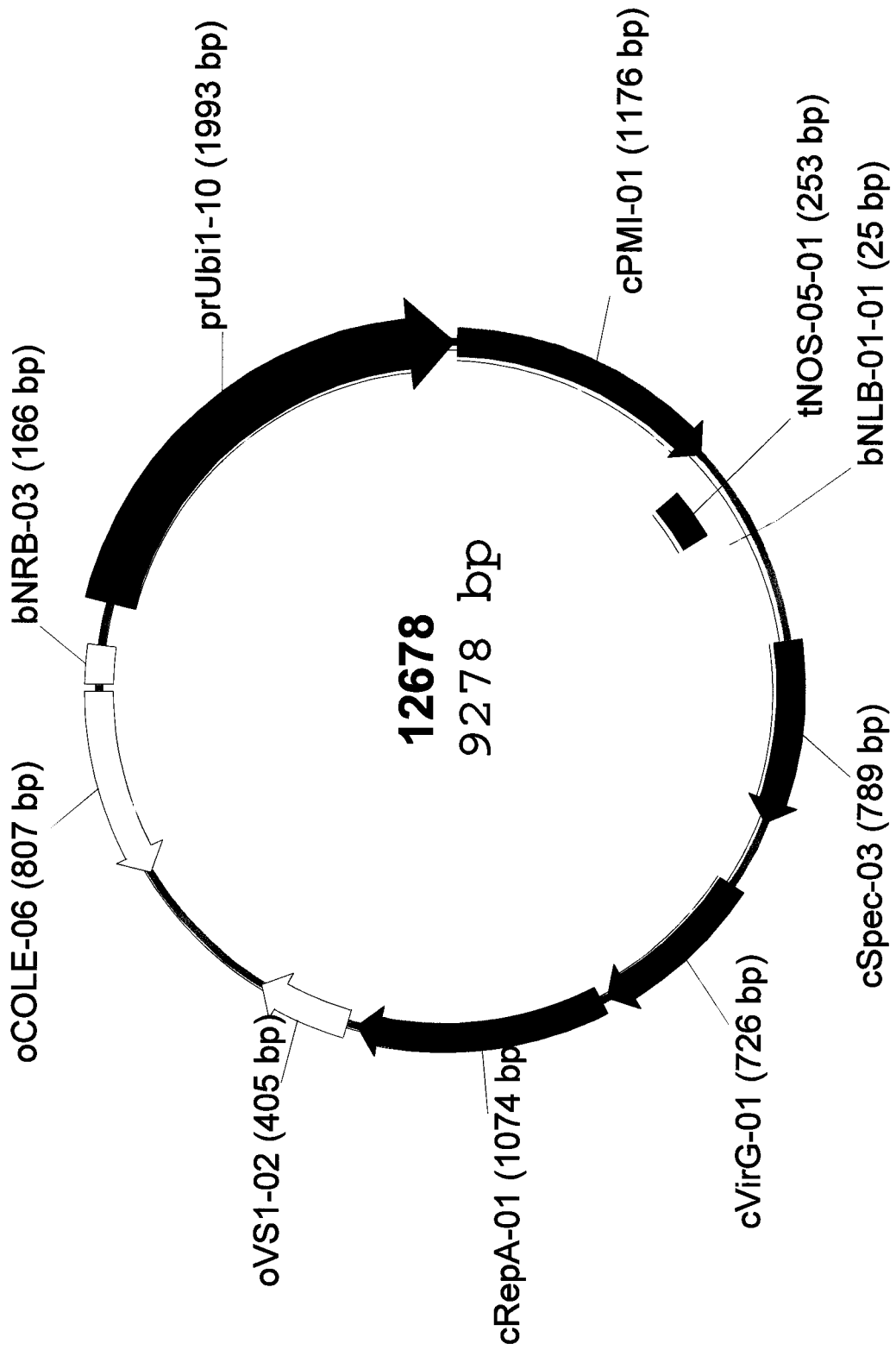
FIG. 9: Plasmid map of binary vector 12678.

To determine if the LC % effect observed with OsMADS1 promoter and 5' genomic sequence is specific for OsMADS1, construct 20096 (FIG. 8) was produced. Like 20070, 20096 comprises the coding sequence for a rice trehalose-6-phosphate phosphatase (cT6PP-01) gene. They differed in their 5' regulatory regions and terminator sequences. The cT6PP-01 transcriptional cassette for construct 20096 comprises the terminator from *Oryza sativa* OsMADS2 (tOsMADS-01; GenBank accession AF095645). The 5' regulatory region of construct 20096 comprises the OsMADS2 promoter (GenBank accession AF095645), the 5' non-transcribed sequence, exon 1, intron 1, and part of exon 2. This eFMV-03-e35S-05-prOsMADS2-01-cT6PP-01-tOsMADS2-01 cassette is disclosed as SEQ ID NO: 9. Similar to 20070, the ATG start codon in exon 1 of the OsMADS2-01 promoter in construct 20096 has been mutated to prevent translation, and the prOsMADS2-01 is operably linked to a maize-optimized Kozak sequence at its 3' end. Like 20070, 20096 has a second expression cassette, comprising a maize ubiquitin promoter (prUbi1-10) operably linked to the coding sequence of PMI (cPMI-01), operably linked to the maize tUbi1-01 terminator sequence (FIG. 9).

Constructs 12672, 22230, 20070, 20096, and construct 20070 were introduced into *A. tumefaciens*, transformed into maize, and transformants were grown on PMI selectable media as described in Example 1. DNA from the regenerated plantlets, now referred to as events, was isolated and analyzed using TAQMAN™ qPCR to determine copy number of the introduced PMI gene, as described in Example 1. Results from copy number analysis and the calculated transformation frequency for each event population transformed with each construct is shown in Table 4.

TABLE 4

Copy number analysis and calculated transformation frequency of events transformed with OsMADS1 promoter constructs

| Construct | Transcriptional Cassette | # Events Tested | LC %* | TF % |
|---|---|---|---|---|
| 22230 | eFMV-03-e35S-05-prOsMADS1-05-cPMI-01-tOsMADS1-03 | 83 | 47.11$^a$ | 21.00$^a$ |
| 21099 | eFMV-03-e35S-05-prOsMADS1-05-tOsMADS1-03 | 407 | 47.68$^a$ | 17.44$^a$ |
| 20070 | eFMV-03-e35S-05-prOsMADS1-05-cT6PP-01-tOsMADS1-03 | 215 | 35.01$^a$ | 10.16$^b$ |
| 20096 | eFMV-03-e35S-05-prOsMADS2-01-cT6PP-01-tOsMADS2-01 | 133 | 28.51$^b$ | 11.34 |
| 12672 | prUbi1-20-cPMI-01-tNOS-05-01 | 2483 | 24.44$^b$ | 42.65$^a$ |

*Different letters indicate significant differences in a two tailed student's t test ($p < 0.05$).

As can be seen from Table 4, significantly more of the events comprising constructs 22230, 21099, and 20070 were low-copy events. Additionally, results in Table 4 show that the 5' regulatory regions in prOsMADS2-01 do not confer the same increase in the percent of low copy events observed with the 5'regulatory region in prOsMADS1-05 (see Table 4). This may be due to insufficient homology between the OsMADS2 gene and a maize MADS gene which is essential for the maize plant cell to survive the transformation and regeneration process.

Figure 10:
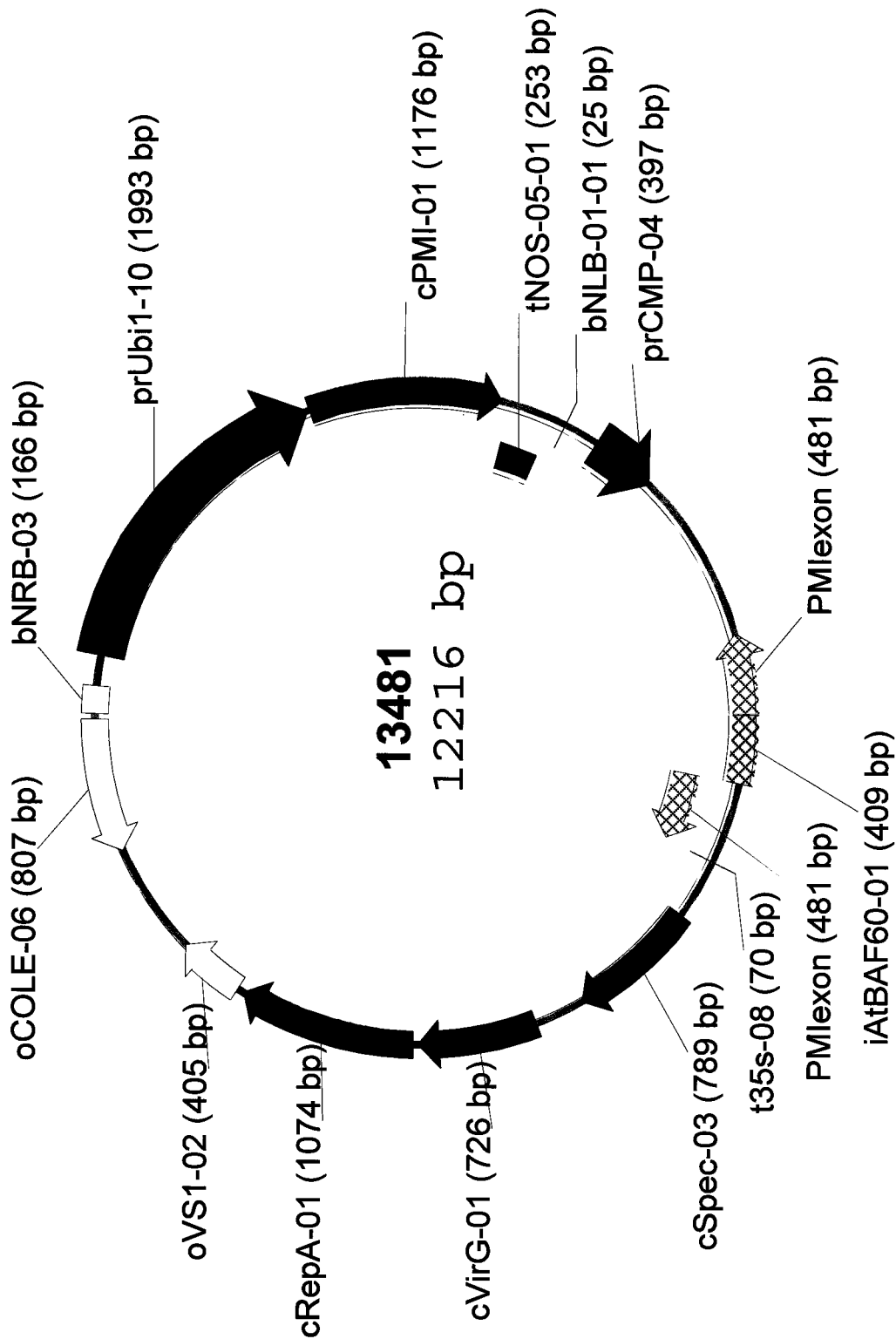
FIG. 10: Plasmid map of binary vector 13481.
Figure 11:
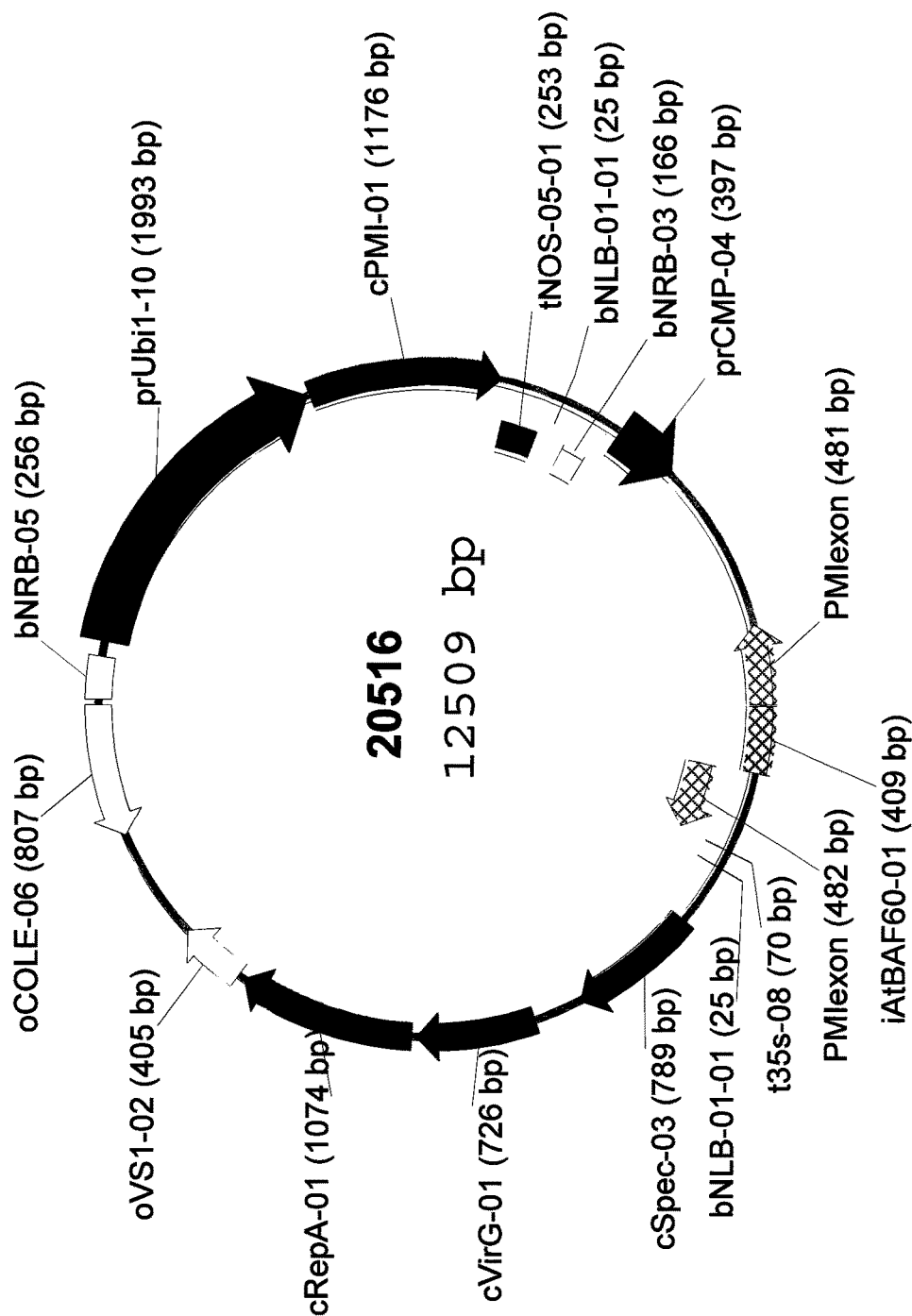
FIG. 11: Plasmid map of binary vector 20516.

Example 3: A Construct Designed to Trigger RNA-Mediated Silencing of the Selectable Marker Increases the Number of Single Copy Events Recovered in Zea Mays Agrobacterium-Mediated Transformation For this example, constructs 12678, 13481 and 20516 (FIGS. 9, 10, and 11) were synthesized. Construct 12678 comprises a single transcriptional cassette comprising a maize ubiquitin promoter (prUbi1-10) (Christensen et al. 1992 Plant Mol Biol 18: 675) operably linked to a PMI coding sequence (cPMI-01) further operably linked to a nopaline synthase (NOS) 3' end transcription termination and polyadenylation, or terminator, sequence (tNOS-05-01). This single transcriptional cassette (SEQ ID NO: 10) is located between right and left T-DNA borders (bNRB and bNLB, respectively) on a binary vector, which also contains appropriate antibiotic selectable markers, origins of replication, and *Agrobacterium* genes known in the art to be typical for a binary vector (FIG. 9). This construct served as a control for the RNAi constructs. Construct 13481 comprises a PMI cassette within the right and left T-DNA borders, similar to 12678. In addition, a second PMI RNAi-type cassette (SEQ ID NO: 11) was introduced in the vector backbone region. This RNAi-type cassette comprises a Cestrum yellow leaf curl virus (CMP) promoter sequence (prCMP-04; U.S. Pat. No. 7,166,770), operably linked to a 481 bp fragment from the PMI gene in the sense orientation (PMI exon), operably linked to an *Arabidopsis thaliana* BAF60 intron (iAtBAF60-01), operably linked to a second 481 bp fragment from the PMI gene that was complementary to the first 481 bp PMI fragment, in the anti-sense orientation (PMI exon), operably linked to a 35S terminator sequence (t35s-08). The binary plasmid 20516 comprises a PMI cassette and a PMI RNAi-type cassette identical to those of 13481. However, in the 20516 construct each cassette is flanked by right and left T-DNA borders. Specifically, in 20516 the PMI RNAi-type cassette is between a right T-DNA border in proximity to the prCMP-04 promoter sequence and a left T-DNA borders in proximity to the t35S-08 terminator sequence.

Each of the above described constructs was introduced into A. tumefaciens, transformed into maize embryos and transformants were grown on PMI selectable media as described in Example 1. DNA from the regenerated plantlets, now referred to as events, was isolated and analyzed using TAQMAN™ qPCR to determine copy number of the introduced PMI gene, as described in Example 1. Results from copy number analysis and the calculated transformation frequency for each event population transformed with each construct are shown in Table 5.

TABLE 5

Copy number analysis and calculated transformation frequency of events transformed with PMI RNAi-type constructs

| Construct | Cassettes flanked by right and left T-DNA borders | # Embryos Transformed | LC % | TF % |
|---|---|---|---|---|
| 12678 | prUbi1-10-cPMI-01-tNOS-05-01 | 388 | 53.60$^a$ | 47.55 |
| 13481 | prUbi1-10-cPMI-01-tNOS-05-01 | 256 | 51.54$^a$ | 32.85 |
| 20516 | prUbi1-10-cPMI-01-tNOS-05-01; prCMP-04-PMIexon-iAtBAF60-01-PMIexon-t35s-08 | 170 | 76.21$^b$ | 21.60 |

*Different letters indicate significant differences in a two tailed student's t test ($p < 0.05$).

As shown in Table 5, construct 13481, which had the PMI RNAi-type cassette outside of the T-DNA borders, did not provide an improvement in the percent of events which were low-copy. However, the transformation frequency decreased significantly. It is known in the art that during transfer of the T-DNA into the host cell, read-through can occur such that information beyond the left border, where the PMI RNAi-type cassette was located, may be transferred into the host as well. Because the PMI RNAi-type cassette is designed to trigger silencing of PMI, the events where this occurred would not survive on PMI selectable media. This may be why the transformation frequency decreased for the 13481 events. The events transformed with construct 20516 resulted in both an increase in the number of low copy events and a significant decrease in the transformation frequency. The decrease in transformation frequency is likely due to a mechanism similar to that in events transformed with 13481. Because 20516 has the PMI RNAi-type cassette as a T-DNA, then those events which integrated both the PMI cassette and the PMI RNAi-type cassette could have silencing of PMI triggered, so that they would not survive on PMI selectable media. However, it is important to recognize that events with the 20516 construct also have a significantly greater percentage of the desirable low-copy events. Taken together, the data indicates that of the 20516 events which survive on PMI-selectable media, a much greater percentage are desirable low-copy events compared to events transformed with either the control 12678 construct or the 13481 construct.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. An *Agrobacterium*-mediated transformation method for making transgenic plant cells, comprising:
   a. providing a first T-DNA polynucleotide comprising all transcriptional cassettes of interest, wherein the first transcriptional cassette comprises a selectable marker, wherein the selectable marker is PMI, and at least one transcriptional cassette comprises a trait gene;
   b. providing a second T-DNA polynucleotide comprising a transcriptional cassette, wherein said transcriptional cassette is transcribed into RNA and whose expression induces reduced expression or silencing of said selectable marker;
   c. providing a DNA plasmid for *Agrobacterium*-mediated transformation, comprising said first T-DNA polynucleotide and said second T-DNA polynucleotide;
   d. performing *Agrobacterium*-mediated transformation on a plurality of cells to produce a plurality of transgenic plant cells;
   e. selecting for transgenic plant cells which only contain said first T-DNA polynucleotide using the selection agent for said selectable marker; and
   f. growing transgenic tissues from said transgenic plant cells of step (e), wherein transgenic plant cells with the second T-DNA polynucleotide of step (b) have reduced survivability through the transformation and regeneration process, and an increased percentage of said transgenic cells carrying only one copy of each transcriptional cassette within the first T-DNA polynucleotide of step (a) is generated compared to methods without step (b).

2. The method of claim 1, wherein the transcriptional cassette of step (b) has at least 60%, 70%, 80%, 85%, 90% or at least 95% sequence identity to said selectable marker, or a fragment thereof.

3. The method of claim 1, wherein the second T-DNA polynucleotide is further comprised of a first polynucleotide fragment of the selectable marker, wherein said first polynucleotide fragment is at least 20 nucleotides in length, operably linked to a polynucleotide linker, operably linked to a second polynucleotide fragment at least 20 polynucleotides in length which is complementary to the first polynucleotide fragment.

4. The method of claim 1, wherein said selectable marker provides selection in the presence of a selection agent, wherein the selection agent is selected from the group consisting of antibiotics, herbicides, drugs, metabolite analogs, metabolic intermediates, or phytohormone precursors.

5. The method of claim 1, wherein the selectable marker is PMI.

6. The method of claim 1, wherein said transcriptional cassette of step (b) comprises SEQ ID NO: 15.

7. A DNA plasmid comprising the first and second T-DNA polynucleotides of claim 1.

8. The method of claim 1, further comprising the step of determining the copy number of each transcriptional cassette of interest comprised in said transgenic tissues.

9. The method of claim 8, further comprising the step of selecting a transgenic tissue comprising a single copy of the transcriptional cassettes and growing the plant tissue into a plant.

10. A plant, plant tissue, or plant cell made by the method of claim 1, wherein the plant, plant tissue, or plant cell comprises the DNA plasmid comprising the first T-DNA polynucleotide and the second T-DNA polynucleotide.

* * * * *

SEQUENCE LISTING

<160> NUMBER OF SEQ ID NOS: 17

<210> SEQ ID NO 1
<211> LENGTH: 3741
<212> TYPE: DNA
<213> ORGANISM: Artificial Sequence
<220> FEATURE:
<223> OTHER INFORMATION: Sources:  Cestrum Yellow Leaf Curl Virus, Zea
      mays, Agrobacterium tumefaciens

<400> SEQUENCE: 1

```
aaagattcaa atagaggacc taacagaact cgccgtaaag actggcgaac agttcataca      60
gagtctctta cgactcaatg acaagaagaa aatcttcgtc aacatggtgg agcacgacac     120
gcttgtctac tccaaaaata tcaaagatac agtctcagaa gaccaaaggg caattgagac     180
ttttcaacaa agggtaatat ccggaaacct cctcggattc cattgcccag ctatctgtca     240
ctttattgtg aagatagtgg aaaaggaagg tggctcctac aaatgccatc attgcgataa     300
aggaaaggcc atcgttgaag atgcctctgc cgacagtggt cccaaagatg gacccccacc     360
cacgaggagc atcgtggaaa aagaagacgt tccaaccacg tcttcaaagc aagtggattg     420
atgtgataac ttttcaacaa agggtaatat ccggaaacct cctcggattc cattgcccag     480
ctatctgtca ctttattgtg aagatagtgg aaaaggaagg tggctcctac aaatgccatc     540
```

-continued

```
attgcgataa aggaaaggcc atcgttgaag atgcctctgc cgacagtggt cccaaagatg    600 gaccccccacc cacgaggagc atcgtggaaa agaagacgt tccaaccacg tcttcaaagc    660
aagtggattg atgtgataac tccactgacg taagggatga cgaacaatcc cactatcctt    720
cacccatgga gtcaaagatt caaatagagg acctaacaga actcgccgta aagactggcg    780
aacagttcat acagagtctc ttacgactca atgacaagaa gaaaatcttc gtcaacatgg    840
tggagcacga cacgcttgtc tactccaaaa atatcaaaga tacagtctca gaagaccaaa    900
gggcaattga gacttttcaa caaagggtaa tatccggaaa cctcctcgga ttccattgcc    960
cagctatctg tcactttatt gtgaagatag tggaaaagga aggtggctcc tacaaatgcc    1020
atcattgcga taaggaaag gccatcgttg aagatgcctc tgccgacagt ggtcccaaag    1080
atggaccccc acccacgagg agcatcgtgg aaaagaaga cgttccaacc acgtcttcaa    1140
agcaagtgga ttgatctgca gcggaccccg accctcatg agcggagaat taagggagtc    1200
acgttatgac ccccgccgat gacgcgggac aagccgtttt acgtttggaa ctgacagaac    1260
cgcaacgaag ctttggcaga caaagtggca gacatactgt cccacaaatg aagatggaat    1320
ctgtaaaaga aaacgcgtga aataatgcgt ctgacaaagg ttaggtcggc tgcctttaat    1380
caataccaaa gtggtcccta ccacgatgga aaaactgtgc agtcggtttg cttttttctg    1440
acgaacaaat aagattcgtg gccgacaggt ggggtccac catgtgaagg catcttcaga    1500
ctccaataat ggagcaatga cgtaagggct tacgaaataa gtaagggtag tttgggaaat    1560
gtccactcac ccgtcagtct ataaatactt agcccctccc tcattgttaa gggagcaaaa    1620
tctcagagag atagtcctag agagagaaag agagcaagta gcctagaagt ggatccacct    1680
cgagtatttt tacaacaatt accaacaaca acaaacaaca acaacatta caattactat    1740 ttacaattac acatgtaaac catggcttcg atctcctcct cagtcgcgac cgttagcagg    1800 accgccctg ctcaggccaa catggtggct ccgttcaccg gccttaagtc caacgccgcc    1860
ttccccacca ccaagaaggc taacgacttc tccacccttc ccagcaacgg tggaagagtt    1920
caatgtatgc aggtgtggcc ggcctacggc aacaagaagt tcgagacgct gtcgtacctg    1980
ccgccgctgt ctatgcgcc caccgtgatg atggcctcgt cggccaccgc cgtcgctccg    2040 ttccagggc tcaagtccac cgccagcctc cccgtcgccc gccgctcctc cagaagcctc    2100
ggcaacgtca gcaacggcgg aagaatccgg tgcatggccg gtgccgagga gatcgtgctg    2160
cagccgatca aggagatcag cggcaccgtg aagctgccgg gcagcaagag cctgagcaac    2220
cgcatcctgc tgctggccgc cctgagcgag gcaccaccg tggtggacaa cctgctgaac    2280
agcgaggacg tgcactacat gctgggcgcc ctgaggaccc tgggcctgag cgtggaggcc    2340
gacaaggccg ccaagagggc cgtggtggtg gctgcggcg gcaagttccc ggtggaggac    2400
gccaaggagg aggtgcagct gttcctgggc aacgccggca tcgccatgag gagcctgacc    2460
gccgccgtga ccgccgccgg cggcaacgcc acctacgtgc tggacggcgt gccgaggatg    2520
agggagaggc cgatcggcga cctggtggtg ggcctgaagc agctgggcgc cgacgtggac    2580
tgcttcctgg gcaccgactg cccgccggtg agggtgaacg gcatcggcgg cctgccgggc    2640
ggcaaggtga agctgagcgg cagcatcagc agccagtacc tgagcgccct gctgatggcc    2700
gccccgctgg ccctgggcga cgtggagatc gagatcatcg acaagctgat cagcatcccg    2760
tacgtggaga tgaccctgag gctgatggag aggttcggcg tgaaggccga gcacagcgac    2820
agctgggaca ggttctacat caaggggcgg cagaagtaca agagcccgaa gaacgcctac    2880
gtggagggcg acgccagcag cgccagctac ttcctggccg gcgccgccat caccggcggc    2940
```

```
accgtgaccg tggagggctg cggcaccacc agcctgcagg gcgacgtgaa gttcgccgag   3000
gtgctggaga tgatgggcgc caaggtgacc tggaccgaga ccagcgtgac cgtgaccggc   3060
ccgccgaggg agccgttcgg caggaagcac ctgaaggcca tcgacgtgaa catgaacaag   3120 atgccgacg tggccatgac cctggccgtg gtggccctgt cgccgacgg cccgaccgcc   3180 atcagggacg tggccagctg gagggtgaag gagaccgaga ggatggtggc catcaggacc   3240
gagctgacca agctgggcgc cagcgtggag gagggcccgg actactgcat catcaccccg   3300
ccggagaagc tgaacgtgac cgccatcgac acctacgacg accacaggat ggcgatggcc   3360
ttcagcctgg ccgcctgcgc cgaggtgccg gtgaccatca gagacccggg ctgcaccagg   3420
aagaccttcc cggactactt cgacgtgctg agcaccttcg tgaagaacta aagagctctt   3480
catatgacga tcgttcaaac atttggcaat aaagtttctt aagattgaat cctgttgccg   3540
gtcttgcgat gattatcata taatttctgt tgaattacgt taagcatgta ataattaaca   3600
tgtaatgcat gacgttattt atgagatggg tttttatgat tagagtcccg caattataca   3660
tttaatacgc gatagaaaac aaaatatagc gcgcaaacta ggataaatta tcgcgcgcgg   3720
tgtcatctat gttactagat c                                             3741

<210> SEQ ID NO 2
<211> LENGTH: 1980
<212> TYPE: DNA
<213> ORGANISM: Artificial Sequence
<220> FEATURE:
<223> OTHER INFORMATION: Sources:   Zea mays, Agrobacterium tumefaciens

<400> SEQUENCE: 2
atggcttcga tctcctcctc agtcgcgacc gttagcagga ccgcccctgc tcaggccaac     60
atggtggctc cgttcaccgg ccttaagtcc aacgccgcct tccccaccac caagaaggct    120
aacgacttct ccaccttcc cagcaacggt ggaagagttc aatgtatgca ggtgtggccg    180
gcctacggca acaagaagtt cgagacgctg tcgtacctgc cgccgctgtc tatggcgccc    240
accgtgatga tggcctcgtc ggccaccgcc gtcgctccgt tccaggggct caagtccacc    300
gccagcctcc ccgtcgcccg ccgctcctcc agaagcctcg gcaacgtcag caacggcgga    360
agaatccggt gcatggccgg tgccgaggag atcgtgctgc agccgatcaa ggagatcagc    420
ggcaccgtga agctgccggg cagcaagagc ctgagcaacc gcatcctgct gctggccgcc    480
ctgagcgagg gcaccaccgt ggtggacaac ctgctgaaca gcgaggacgt gcactacatg    540
ctgggcgccc tgaggaccct gggcctgagc gtggaggccg acaaggccgc caagagggcc    600
gtggtggtgg gctgcggcgg caagttcccg gtggaggacg ccaaggagga ggtgcagctg    660
ttcctgggca acgccggcat cgccatgagg agcctgaccg ccgccgtgac cgccgccggc    720
ggcaacgcca cctacgtgct ggacggcgtg ccgaggatga gggagaggcc gatcggcgac    780
ctggtggtgg gcctgaagca gctgggcgcc gacgtggact gcttcctggg caccgactgc    840
ccgccggtga gggtgaacgg catcggcggc ctgccgggcg gcaaggtgaa gctgagcggc    900
agcatcagca gccagtacct gagcgccctg ctgatggccg cccgctggc cctgggcgac    960 gtggagatcg agatcatcga caagctgatc agcatcccgt acgtggagat gaccctgagg   1020
ctgatggaga ggttcggcgt gaaggccgag cacagcgaca gctgggacag gttctacatc   1080
aagggcggcc agaagtacaa gagcccgaag aacgcctacg tggagggcga cgccagcagc   1140
gccagctact tcctggccgg cgccgccatc accggcggca ccgtgaccgt ggagggctgc   1200
```

-continued

```
ggcaccacca gcctgcaggg cgacgtgaag ttcgccgagg tgctggagat gatgggcgcc    1260
aaggtgacct ggaccgagac cagcgtgacc gtgaccggcc cgccgaggga gccgttcggc    1320
aggaagcacc tgaaggccat cgacgtgaac atgaacaaga tgccggacgt ggccatgacc    1380
ctggccgtgg tggccctgtt cgccgacggc ccgaccgcca tcaggacgtg gccagctgg     1440 agggtgaagg agaccgagag gatggtggcc atcaggaccg agctgaccaa gctgggcgcc    1500
agcgtggagg agggcccgga ctactgcatc atcaccccgc cggagaagct gaacgtgacc    1560
gccatcgaca cctacgacga ccacaggatg gcgatggcct tcagcctggc cgcctgcgcc    1620
gaggtgccgg tgaccatcag agacccgggc tgcaccagga gaccttccc ggactacttc     1680 gacgtgctga gcaccttcgt gaagaactaa agagctcttc atatgacgat cgttcaaaca    1740
tttggcaata aagtttctta agattgaatc ctgttgccgg tcttgcgatg attatcatat    1800
aatttctgtt gaattacgtt aagcatgtaa taattaacat gtaatgcatg acgttattta    1860
tgagatgggt ttttatgatt agagtcccgc aattatacat ttaatacgcg atagaaaaca    1920
aaatatagcg cgcaaactag gataaattat cgcgcgcggt gtcatctatg ttactagatc    1980
```

<210> SEQ ID NO 3
<211> LENGTH: 1608
<212> TYPE: DNA
<213> ORGANISM: Artificial Sequence
<220> FEATURE:
<223> OTHER INFORMATION: Sources: Zea mays, Agrobacterium tumefaciens

<400> SEQUENCE: 3

```
atggccggtg ccgaggagat cgtgctgcag ccgatcaagg agatcagcgg caccgtgaag      60
ctgccgggca gcaagagcct gagcaaccgc atcctgctgc tggccgccct gagcgagggc     120
accaccgtgg tggacaacct gctgaacagc gaggacgtgc actacatgct gggcgccctg     180
aggaccctgg gcctgagcgt ggaggccgac aaggccgcca gagggccgt ggtggtgggc      240 tgcggcggca agttcccggt ggaggacgcc aaggaggagg tgcagctgtt cctgggcaac     300
gccggcatcg ccatgaggag cctgaccgcc gccgtgaccg ccgccggcgg caacgccacc     360
tacgtgctgg acggcgtgcc gaggatgagg gagaggccga tcggcgacct ggtggtgggc     420
ctgaagcagc tgggcgccga cgtggactgc ttcctgggca ccgactgccc gccggtgagg     480
gtgaacggca tcgcggcct gccgggcggc aaggtgaagc tgagcggcag catcagcagc     540
cagtacctga gcgccctgct gatggccgcc ccgctggccc tgggcgacgt ggagatcgag     600
atcatcgaca agctgatcag catcccgtac gtggagatga ccctgaggct gatggagagg     660
ttcggcgtga aggccgagca cagcgacagc tgggacaggt tctacatcaa gggcggccag     720
aagtacaaga gcccgaagaa cgcctacgtg gagggcgacg ccagcagcgc cagctacttc     780
ctggccggcg ccgccatcac cggcggcacc gtgaccgtgg agggctgcgg caccaccagc     840
ctgcagggcg acgtgaagtt cgccgaggtg ctggagatga tgggcgccaa ggtgacctgg     900
accgagacca gcgtgaccgt gaccggcccg ccgagggagc cgttcggcag gaagcacctg     960
aaggccatcg acgtgaacat gaacaagatg ccggacgtgg ccatgaccct ggccgtggtg     1020
gccctgttcg ccgacggccc gaccgccatc agggacgtgg ccagctggag ggtgaaggag     1080
accgagagga tggtggccat caggaccgag ctgaccaagc tgggcgccag cgtggaggag     1140
ggcccggact actgcatcat caccccgccg gagaagctga acgtgaccgc catcgacacc     1200
tacgacgacc acaggatggc gatggccttc agcctggccg cctgcgccga ggtgccggtg     1260
accatcagag acccgggctg caccaggaag accttcccgg actacttcga cgtgctgagc     1320
```

-continued

| | |
|---|---|
| accttcgtga agaactaaag agctcttcat atgacgatcg ttcaaacatt tggcaataaa | 1380 |
| gtttcttaag attgaatcct gttgccggtc ttgcgatgat tatcatataa tttctgttga | 1440 |
| attacgttaa gcatgtaata attaacatgt aatgcatgac gttatttatg agatgggttt | 1500 |
| ttatgattag agtcccgcaa ttatacattt aatacgcgat agaaaacaaa atatagcgcg | 1560 |
| caaactagga taaattatcg cgcgcggtgt catctatgtt actagatc | 1608 |

<210> SEQ ID NO 4
<211> LENGTH: 3741
<212> TYPE: DNA
<213> ORGANISM: Artificial Sequence
<220> FEATURE:
<223> OTHER INFORMATION: Sources: CaMV, Cestrum Yellow Leaf Curl Virus, Zea mays, Agrobacterium tumefaciens

<400> SEQUENCE: 4

| | |
|---|---|
| aaagattcaa atagaggacc taacagaact cgccgtaaag actggcgaac agttcataca | 60 |
| gagtctctta cgactcaatg acaagaagaa aatcttcgtc aacatggtgg agcacgacac | 120 |
| gcttgtctac tccaaaaata tcaaagatac agtctcagaa gaccaaaggg caattgagac | 180 |
| ttttcaacaa agggtaatat ccggaaacct cctcggattc cattgcccag ctatctgtca | 240 |
| ctttattgtg aagatagtgg aaaggaagg tggctcctac aaatgccatc attgcgataa | 300 |
| aggaaaggcc atcgttgaag atgcctctgc cgacagtggt cccaaagatg gacccccacc | 360 |
| cacgaggagc atcgtggaaa aagaagacgt tccaaccacg tcttcaaagc aagtggattg | 420 |
| atgtgataac ttttcaacaa agggtaatat ccggaaacct cctcggattc cattgcccag | 480 |
| ctatctgtca ctttattgtg aagatagtgg aaaggaagg tggctcctac aaatgccatc | 540 |
| attgcgataa aggaaaggcc atcgttgaag atgcctctgc cgacagtggt cccaaagatg | 600 |
| gacccccacc cacgaggagc atcgtggaaa aagaagacgt tccaaccacg tcttcaaagc | 660 |
| aagtggattg atgtgataac tccactgacg taagggatgc cgaacaatcc cactatcctt | 720 |
| cacccatgga gtcaaagatt caaatagagg acctaacaga actcgccgta agactggcg | 780 |
| aacagttcat acagagtctc ttacgactca atgacaagaa gaaaatcttc gtcaacatgg | 840 |
| tggagcacga cacgcttgtc tactccaaaa atatcaaaga tacagtctca gaagaccaaa | 900 |
| gggcaattga cttttcaa caagggtaa tatccggaaa cctcctcgga ttccattgcc | 960 |
| cagctatctg tcactttatt gtgaagatag tggaaaagga aggtggctcc tacaaatgcc | 1020 |
| atcattgcga taaaggaaag gccatcgttg aagatgcctc tgccgacagt ggtcccaaag | 1080 |
| atggaccccc acccacgagg agcatcgtgg aaaagaaga cgttccaacc acgtcttcaa | 1140 |
| agcaagtgga ttgatctgca gcggaccccg gaccctcatg agcggagaat aagggagtc | 1200 |
| acgttatgac ccccgccgat gacgcgggac aagccgtttt acgtttggaa ctgacagaac | 1260 |
| cgcaacgaag ctttggcaga caaagtggca gacatactgt cccacaaatg aagatggaat | 1320 |
| ctgtaaaaga aaacgcgtga ataatgcgt ctgacaaagg ttaggtcggc tgcctttaat | 1380 |
| caataccaaa gtggtcccta ccacgatgga aaaactgtgc agtcggtttg cttttttctg | 1440 |
| acgaacaaat aagattcgtg gccgacaggt ggggtccac catgtgaagg catcttcaga | 1500 |
| ctccaataat ggagcaatga cgtaagggct tacgaaataa gtaagggtag tttgggaaat | 1560 |
| gtccactcac ccgtcagtct ataaatactt agccctccc tcattgttaa gggagcaaaa | 1620 |
| tctcagagag atagtcctag agagagaaag agagcaagta gcctagaagt ggatccacct | 1680 |
| cgagtatttt tacaacaatt accaacaaca acaaacaaca aacaacatta caattactat | 1740 |

```
ttacaattac acatgtaaac catggcttcg atctcctcct cagtcgcgac cgttagcagg   1800
accgcccctg ctcaggccaa catggtggct ccgttcaccg gccttaagtc caacgccgcc   1860
ttccccacca ccaagaaggc taacgacttc tccacccttc ccagcaacgg tggaagagtt   1920
caatgtatgc aggtgtggcc ggcctacggc aacaagaagt tcgagacgct gtcgtacctg   1980
ccgccgctgt ctatggcgcc caccgtgatg atggcctcgt cggccaccgc cgtcgctccg   2040
ttccaggggc tcaagtccac cgccagcctc cccgtcgccc gccgctcctc cagaagcctc   2100
ggcaacgtca gcaacggcgg aagaatccgg tgctgagccg gtgccgagga gatcgtgctg   2160
cagccgatca aggagatcag cggcaccgtg aagctgccgg gcagcaagag cctgagcaac   2220
cgcatcctgc tgctggccgc cctgagcgag ggcaccaccg tggtggacaa cctgctgaac   2280
agcgaggacg tgcactacat gctgggcgcc ctgaggaccc tgggcctgag cgtggaggcc   2340
gacaaggccg ccaagagggc cgtggtggtg ggctgcggcg gcaagttccc ggtggaggac   2400
gccaaggagg aggtgcagct gttcctgggc aacgccggca tcgccatgag gagcctgacc   2460
gccgccgtga ccgccgccgg cggcaacgcc acctacgtgc tggacggcgt gccgaggatg   2520
agggagaggc cgatcggcga cctggtggtg ggcctgaagc agctgggcgc cgacgtggac   2580
tgcttcctgg caccgactg cccgccggtg agggtgaacg catcggcgg cctgccgggc   2640 ggcaaggtga agctgagcgg cagcatcagc agccagtacc tgagcgccct gctgatggcc   2700
gccccgctgg ccctgggcga cgtggagatc gagatcatcg acaagctgat cagcatcccg   2760
tacgtggaga tgaccctgag gctgatggag aggttcggcg tgaaggccga gcacagcgac   2820
agctgggaca ggttctacat caagggcggc cagaagtaca agagcccgaa gaacgcctac   2880
gtggagggcg acgccagcag cgccagctac ttcctggccg cgccgccat caccggcggc   2940 accgtgaccg tggagggctg cggcaccacc agcctgcagg gcgacgtgaa gttcgccgag   3000
gtgctggaga tgatgggcgc caaggtgacc tggaccgaga ccagcgtgac cgtgaccggc   3060
ccgccgaggg agccgttcgg caggaagcac ctgaaggcca tcgacgtgaa catgaacaag   3120
atgccggacg tggccatgac cctggccgtg gtggccctgt cgccgacgg cccgaccgcc   3180 atcagggacg tggccagctg gagggtgaag gagaccgaga ggatggtggc catcaggacc   3240
gagctgacca gctgggcgc cagcgtggag gagggcccgg actactgcat catcaccccg   3300
ccggagaagc tgaacgtgac cgccatcgac acctacgacg accacaggat ggcgatggcc   3360
ttcagcctgg ccgcctgcgc cgaggtgccg gtgaccatca gagacccggg ctgcaccagg   3420
aagaccttcc cggactactt cgacgtgctg agcaccttcg tgaagaacta aagagctctt   3480
catatgacga tcgttcaaac atttggcaat aaagtttctt aagattgaat cctgttgccg   3540
gtcttgcgat gattatcata taatttctgt tgaattacgt taagcatgta ataattaaca   3600
tgtaatgcat gacgttattt atgagatggg ttttatgat tagagtcccg caattataca   3660
tttaatacgc gatagaaaac aaaatatagc gcgcaaacta ggataaatta tcgcgcgcgg   3720
tgtcatctat gttactagat c                                            3741
```

<210> SEQ ID NO 5
<211> LENGTH: 3739
<212> TYPE: DNA
<213> ORGANISM: Artificial Sequence
<220> FEATURE:
<223> OTHER INFORMATION: Sources: CaMV, Cestrum Yellow Leaf Curl Virus,
      Zea mays, Agrobacterium tumefaciens

<400> SEQUENCE: 5

-continued

```
aaagattcaa atagaggacc taacagaact cgccgtaaag actggcgaac agttcataca      60
gagtctctta cgactcaatg acaagaagaa atcttcgtc aacatggtgg agcacgacac      120
gcttgtctac tccaaaaata tcaaagatac agtctcagaa gaccaaaggg caattgagac     180
ttttcaacaa agggtaatat ccggaaacct cctcggattc cattgcccag ctatctgtca     240
ctttattgtg aagatagtgg aaaaggaagg tggctcctac aaatgccatc attgcgataa     300
aggaaaggcc atcgttgaag atgcctctgc cgacagtggt cccaaagatg accccccacc     360
cacgaggagc atcgtggaaa aagaagacgt tccaaccacg tcttcaaagc aagtggattg     420
atgtgataac ttttcaacaa agggtaatat ccggaaacct cctcggattc cattgcccag     480
ctatctgtca ctttattgtg aagatagtgg aaaaggaagg tggctcctac aaatgccatc     540
attgcgataa aggaaaggcc atcgttgaag atgcctctgc cgacagtggt cccaaagatg     600
gaccccacc cacgaggagc atcgtggaaa aagaagacgt tccaaccacg tcttcaaagc      660
aagtggattg atgtgataac tccactgacg taagggatga cgaacaatcc cactatcctt     720
cacccatgga gtcaaagatt caaatagagg acctaacaga actcgccgta aagactggcg     780
aacagttcat acagagtctc ttacgactca atgacaagaa gaaaatcttc gtcaacatgg     840
tggagcacga cacgcttgtc tactccaaaa atatcaaaga tacagtctca gaagaccaaa     900
gggcaattga cttttcaa caaagggtaa tatccggaaa cctcctcgga ttccattgcc       960
cagctatctg tcactttatt gtgaagatag tggaaaagga aggtggctcc tacaaatgcc    1020
atcattgcga taaggaaaag gccatcgttg aagatgcctc tgccgacagt ggtcccaaag    1080
atggaccccc acccacgagg agcatcgtgg aaaagaaga cgttccaacc acgtcttcaa     1140
agcaagtgga ttgatctgca gcggaccccg gaccctcatg agcggagaat taagggagtc    1200
acgttatgac ccccgccgat gacgcgggac aagccgtttt acgtttggaa ctgacagaac    1260
cgcaacgaag ctttggcaga caaagtggca gacatactgt cccacaaatg aagatggaat    1320
ctgtaaaaga aaacgcgtga ataatgcgt ctgacaaagg ttaggtcggc tgcctttaat     1380
caataccaaa gtggtcccta ccacgatgga aaaactgtgc agtcggtttg gcttttctg     1440
acgaacaaat aagattcgtg gccgacaggt gggggtccac catgtgaagg catcttcaga    1500
ctccaataat ggagcaatga cgtaagggct tacgaaataa gtaagggtag tttgggaaat    1560
gtccactcac ccgtcagtct ataaatactt agccctcccc tcattgttaa gggagcaaaa    1620
tctcagagag atagtcctag agagagaaag agagcaagta gcctagaagt ggatccacct    1680
cgagtatttt tacaacaatt accaacaaca acaaacaaca aacaacatta caattactat    1740
ttacaattac acatgtaaac cagcttcgat ctcctcctca gtcgcgaccg ttagcaggac    1800
cgccctgct caggccaaca tggtggctcc gttcaccggc cttaagtcca acgccgcctt      1860
ccccaccacc aagaaggcta acgacttctc caccttccc agcaacggtg aagagttca     1920
atgtatgcag gtgtggccgg cctacggcaa caagaagttc gagacgctgt cgtacctgcc    1980
gccgctgtct atggcgccca ccgtgatgat ggcctcgtcg gccaccgccg tcgctccgtt    2040
ccagggggctc aagtccaccg ccagcctccc cgtcgcccgc cgctcctcca gaagcctcgg   2100
caacgtcagc aacggcggaa gaatccggtg ctgagcggt gccgaggaga tcgtgctgca     2160
gccgatcaag gagatcagcg gcaccgtgaa gctgccgggc agcaagagcc tgagcaaccg    2220
catcctgctg ctgccgcccc tgagcgaggg caccaccgtg gtggcaacc tgctgaacag    2280
cgaggacgtg cactacatgc tgggcgccct gaggaccctg ggcctgagcg tggaggccga    2340
```

```
caaggccgcc aagagggccg tggtggtggg ctgcggcggc aagttcccgg tggaggacgc    2400
caaggaggag gtgcagctgt tcctgggcaa cgccggcatc gccatgagga gcctgaccgc    2460
cgccgtgacc gccgccggcg gcaacgccac ctacgtgctg gacggcgtgc cgaggatgag    2520
ggagaggccg atcggcgacc tggtggtggg cctgaagcag ctgggcgccg acgtggactg    2580
cttcctgggc accgactgcc cgccggtgag ggtgaacggc atcgcggcc tgccgggcgg     2640 caaggtgaag ctgagcggca gcatcagcag ccagtacctg agcgccctgc tgatggccgc    2700
cccgctggcc ctgggcgacg tggagatcga gatcatcgac aagctgatca gcatcccgta    2760
cgtggagatg accctgaggc tgatggagag gttcggcgtg aaggccgagc acagcgacag    2820
ctgggacagg ttctacatca agggcggcca gaagtacaag agcccgaaga acgcctacgt    2880
ggagggcgac gccagcagcg ccagctactt cctggccggc gccgccatca ccggcggcac    2940
cgtgaccgtg gagggctgcg gcaccaccag cctgcagggc gacgtgaagt cgccggaggt    3000
gctggagatg atgggcgcca aggtgacctg accgagacc agcgtgaccg tgaccggccc     3060
gccgagggag ccgttcggca ggaagcacct gaaggccatc gacgtgaaca tgaacaagat    3120
gccggacgtg gccatgaccc tggccgtggt ggccctgttc gccgacggcc cgaccgccat    3180
cagggacgtg gccagctgga gggtgaagga gaccgagagg atggtggcca tcaggaccga    3240
gctgaccaag ctgggcgcca gcgtggagga gggcccggac tactgcatca tcaccccgcc    3300
ggagaagctg aacgtgaccg ccatcgacac ctacgacgac cacaggatgg cgatggcctt    3360
cagcctggcc gcctgcgccg aggtgccggt gaccatcaga gacccgggct gcaccaggaa    3420
gaccttcccg gactacttcg acgtgctgag caccttcgtg aagaactaaa gagctcttca    3480
tatgacgatc gttcaaacat ttggcaataa agtttcttaa gattgaatcc tgttgccggt    3540
cttgcgatga ttatcatata atttctgttg aattacgtta agcatgtaat aattaacatg    3600
taatgcatga cgttatttat gagatgggtt tttatgatta gagtcccgca attatacatt    3660
taatacgcga tagaaaacaa aatatagcgc gcaaactagg ataaattatc gcgcgcggtg    3720
tcatctatgt tactagatc                                                 3739
```

<210> SEQ ID NO 6
<211> LENGTH: 7960
<212> TYPE: DNA
<213> ORGANISM: Artificial Sequence
<220> FEATURE:
<223> OTHER INFORMATION: Source: Oryza sativa

<400> SEQUENCE: 6

```
acaaatttgt tgtaccacct acctaggggt gacaacactg cacatttggc tatttagggc      60
cacgcatata tgcatgaaaa attgacacac gacgttactt gagaacctat tcatgcaggt     120
ctatgagaaa accccaccaa aaaaaacaga tgtgcaaaat aatgctggat tttcatatgc     180
tataaattaa gtactacttt aatcaaacac cacattgaca cacaatgaca caaattaaat    240
actcttacga attcaagtca tatatactct aatacgcacg tgcagcttgt tactcaaata    300
aagaaacagg gcaatacgga tcagtatatc caaccaggct gcatgtaggc caagaacctg    360
acaattcgtt ttccttggag aaagcaaaga acgtttggaa cgtgtgatgt acatgcagat    420
cgaggaaaat agctaatcct gctctttccc tttccagcac aaaaaaagat tccttcgtag    480
ttcgcactgc atttatactc aaacctgcaa ggctcccaaa cagtttgaac caaggcgagg    540
gaaaaaaaaa acatctccat agccaagaga aaacatactg tacatgtcaa gagattccct    600
cttcatattc ttacaatcct atttactcaa attaaatctt catatttcac ttcgtaaatt    660
```

```
ccaacggcta atttggtcag cacaaattca gcatctcaat caacacaatt tcaatgcatg    720
aaggcgatca agctcaccac tctcctgcca tacaagatgg accgccaccg cttggaattt    780
ccgcagtgac ggcaacacga ggaagaggca acactagcgg atgtatgaag gagtctgcca    840
agctcggcta tttccggcga gcttgagagt ataatcgaga tagaggccgg tggaaagacg    900
aaaggcggcg tactcttggg cttagtgtgg aggcaacggt ggcggcctcg cggagaggtg    960
acgacacctt ggcttggcat ggcagagttc cacttctcaa cagggatgca tgacactcct   1020
aggtaagaag gcggcggtgc tggtgggtgt gggtggaggc acatggactt ctctcaacaa   1080
taaagttgct ctcgctgtca aactattccc tctgccaagt ttgatcactc aatttcttga   1140
tttggctagt cggataagat agtcaccgac atagccaacc agatgggata accccttttt   1200
ttttagcatg gagagtggga ccaaatgtcc aagctatctc ccatactccc tatgtccaaa   1260
aaaaaataat attttttaaa ttcatatcta acatacgaag ataatactct tcgttgaaaa   1320
aaaaacaact tcagaatcta gacacaactt tattttttat aagacggaaa gactgtactc   1380
ctatactcct acatttcacc attttttttcc ccgcgtaaaa acaaaccccc gaattgaccg   1440
tccactgtag catcactcca tcagacttga agcgagtgag agacagagcg ctgcgttaaa   1500
aagaaaagag gaaagaaccg gacgcagagc cctactgtca aactgacaag gcaggaagaa   1560
gaaagggaag ccccccctac caagccctag cctccttgtc cgtttgctcc ccccagcgc    1620 caccccccgt cgacacgcgt cgcccaccct ctgccattcc ctcttccgcc ctcccagcca   1680
ctactacgct tttactccct gccgcgcgcg cgagatcttc accttcaccg tatccgctcg   1740
cgttttgcac gcagttgatt tgcgctttgt ttttgcatcc tacgaaacta accgcacacc   1800
aatcacctcc tccaccaccg cacagagcta tagctagcga ggagcgtgct acagtgcgct   1860
gcgcaggaga gagaatcgat cgatggaaga acgcgacagg agcaagctag ccagcctagc   1920
tgtagcgacg tgacagcagt ttgatctttc ttttttttctt atgatggcta agcttatacg   1980
taagccgatc gatcgatggc gagatagatc agagattaat atacaggggt aattaatgta   2040
ctaattacaa ttaagtgtgt ggacgagcga gccgtgtgga gttacagcta gctagcgctt   2100
atgctactcc tacttaaggc gagaccccaa actccaagca tacgatcagg tagccaaacc   2160
acaccaccat aaagctagct tgcaaagggg atagagtagt agagagagag agagaggaga   2220
ggaggaggaa gaagtagggg aggggaaggg tggagctgaa gcggatcgag aacaagatca   2280
gccggcaggt gacgttcgcc aagcgcagga acggcctgct caagaaggcc tacgagcact   2340
ccctcctctg cgacgccgag gtcgcccctca tcatcttctc cggccgcggc cgcctcttcg   2400
agttctccag ctcatctagg tacgtatagc accaaaccaa cgccgccgcc gccgccggcg   2460
tgcttgttcc ggcgcagcag cgcatcatca tcgatcgatc taagtctaat aagataatca   2520 attacccta actaaataaa atgataagaa cagtatatat ggttatgatc agtgaaacac    2580
tcgtcgatct gagggaaaat ccggtcgaga tcgagggagt ggggagacaa attgaactgc   2640
aggctagcta atttaatcgt gtcgatcgat ttctagcttt tgttgatctt tatatatacg   2700
aacgcatgca cttcccctt tgttttttttt tcccttcgat ctgcttggag cacatatgct   2760
atagatcttg gggcatatgt atctgtcagc tttcgagagc ggctatgtcc atcgatccct   2820 ctttttttc tctttctttt tgtagtatca gctgccatgc atatatcaga tttcgttttc   2880
gcgtgctttt agtgcttcac ttatctgttc gccatatctg atttcttctc atcctttgcc   2940
gacgtcgtct gagcagtctg acctccaaga tctggcgaaa taaacctcaa tcgttgctat   3000
```

```
ttcttgcctt gaatctgcat aaacatgaca atagatcctt ctatttttt tcttcaagac    3060 aagatcttgc tgtttcttcc cttgctattt ttcattcaaa gattcttctt tttttctaa    3120 aagaactata tatatatgaa tcgagtttca tcttcatcga tctgtctctc tccttttgtt    3180
ttctgtaaac acacacacga gcgtacgtat atatactctc atctctactt ttatcaaaaa    3240
gaaacacaca tgttctagct tcagatccca aaataatcaa acaggaaaat atatataata    3300
tgcaattagt tcagatcccg aggtagattt cttgattatt tccatttttcc aaagtgaggc    3360 gcgcgacaac tcgacgcggt tcctctttgc acacacacac agtataactg tacgcaaggg    3420
gtaagaacaa aggagcaatc ccttctgggt tgctgcttgc ttctcccatt tttagctatt    3480
tcagaatttc actttctgag actcatctct ctctctctac cagctgcatt atttcacttc    3540 cctttttcc catttctgcc tattacacgg atggcctctt tgtggactcg tccaaattga    3600
ggcacggtag ctggtgtcaa aatgaacctg caggcccagc ccggttatgt atatgtatag    3660
ctatatagct tttcttgcaa gaggtatata cactttgtag ttttagccag tggtccagct    3720
agccaaggat ggatatatta tacacacgta tatatagtca atgtatgtac gagtgttaat    3780
taaactcgtt tagttaattt ccaaagtcct ttttattac tacagctagc ctgatctgtg    3840
ttttagtgtg ttactgttcc attagttact gttctattga agagagcgcg tacacgttgt    3900
tgttttattt ctcttttcc gatccggtgt tcctttttt tttctttgg tcatcttcct    3960 cgagtcccga gcagtagaaa tactactact gccctgcaaa gcacacacat caagtgatgt    4020 gttttcttc agagcttcag acgtgtcata tcaagcaggt cagcacgcat tacatgcaat    4080
ataatactcc tatatggaca cgcagaactc actttgatca tgtgtgacca agctggatga    4140
gccgttaatt tgttgttggg acagggtatt gaatcattaa ttgcggtttt tcctcttttt    4200
cctgtcttgt tctactcaga gaattgaacg gtgaactgta taggcagagc tagtcctgca    4260
tgcatcggtt ttctgaaaat attaactata cacacacatg cacaattgct aaatctggta    4320
tacatgtctt gctgactcac atattcgttc ctcctaatta aagcactcat ttatttattt    4380
tacacggttt tcaatgatat actttaaata ttaatttgtt tgatgttata tttctatgaa    4440
tatgaaatta gcatcatatg aaaatacttt aaaacaaata tagtgatata acatgcataa    4500
tacttagcat atacttgtat gattagcatg gtcattaatc aaaagttgcc gagcttgaat    4560
tttctaaagg acagggtgcc ttgtaatttg ggacaaagaa ccattggaaa acgaacacaa    4620
agaaactttc attacattaa ttatctgaaa aagaaagaaa ctttcattaa cctcgtacag    4680
taaatagaaa agaggaacta tgcatgtata acgaaatagc taggatcaca gcaattaatt    4740
agttgttctc tggctttact tttcttttgg agtaacttta atttttcttt ggaggatgaa    4800
gtagttaatt atacaggttt ccaattcttg tttggtagat ccttttttat gttcctggaa    4860
gagctactat atttttgtac ttgagatgga gctgaggtac cgttatctag ctatgtcgca    4920
tctcaaggag ttacgaatta acatatatca ccaatatcac aaaaatgctc atacaaaaa    4980 gatcataaaa attcttgaat ttgcttgctg tgttttttta ctatatatgc ttggaattaa    5040
aaaaatgact gaattaatcg tttgcaatct ttaacggtgc gtgcagtacc aaattggaaa    5100
ggtatccact tgttcaaact taaaatatt ttttttactg atattactct ctaaaaaggt    5160
gcatgggaaa tgctattgga actactagtt ttcgggacat tataagaaaa tgtatgcata    5220
tatatatata tatatggact tatgatatgg gccagatacc tatatatata gaagatatat    5280
gtgtgctact acctccattc aacaatacaa gcatttgagc cagttctggt caaggatata    5340
aacatcctgc actattagct tgtacttgtc aaattaatga tctctaattc aaactttctt    5400
```

```
gctactttac ccccaatcac ccttcccaac catcttaatc tttgctaaac attctagaaa    5460
tgcttattgt tggatggagg aagtagctat taactactcc tatagttttt ttaactacct    5520
catattaatt ttgtaatcct aataaatgca ctatatatgc ccacttttac cgtgtttcca    5580
aactggcatc aagctaaaat gaatgttaat ttagtttccc cataattta tgagaatcgc    5640 aaaattgtac ctattttaaa caaatcaaag tcactgaaca aatgaacgga ggttaattat    5700
tatattcacc tgatataggc agactaggtt gggctaagag ggacattaat ttgggcatct    5760
aggttttgaa atgggagata tggagagtga accaaaaaaa aactgttagt gaattagtac    5820
atgatatata ctagtattat tagtgggaac ctagagaaat gcaaagaatg ttgcgcaaat    5880
catcattttg tgtaaattaa aatgggatat acactatggg gaactatagc tgagtgtcaa    5940
tccccacctt ttgtttgtaa ttaaacatgt gtttatgcta caaattactc cctccgtact    6000
cataaaggaa gtcgtttagg acaatgttta agtcaaacct tgggaatata aattatgaat    6060
aactctcaag ttgttgagtt tgaaaatgta aaaaatatat gaatagattt gtcttgaaaa    6120
atactttcat aaaagtatac atatatcact tttcaataaa tattttatag aaacaagaag    6180
tcaaaattgt gttttggaga ccgtgtcact gtccaaaacg acttctttac gagtacggag    6240
ggagtatgtt ctacatattg gctaatattg ttgaacccct cggatcaatc ttagacacag    6300
tagccatttt acccactgat gcagcaaccc aattaggtat ctactaatta gcatcatagt    6360
gcaaatttgt acttttcaag tggaaaatag aaattatttg tcctccttta ctttaatttc    6420
ttgataatat gatatatgta acataatttc tctttgctcc caagcatata aaaaacttca    6480
atttgatatg tccaaaaaat gtcatatata tagcatgtaa tcctctgtgg caaacacgtt    6540
tttttggctc aaattaagaa gaggaaaaaa tggtatatat gtataaacct aacaaaaatg    6600
ccccaacaag aatagcttta ttttgtgaac aaggtcatat agaccaggga acaaaaaccc    6660
tgtactgtgc ttctattttg ctatgcattt tggataagtg attctacaga aatatgacta    6720
tataggagat attctcaaat ctgatctttt ctattaatta gcccatacga tatgaagaca    6780
tatcttcctc tgttctgatt ctatttgttg tgctaagata gtctacagga tttgctaggt    6840
tgccacctgc cgtcaacaaa attcagctca tcagattttg ttatagttgc tagcacagtt    6900
atattatacg tatatctctt ttgagaatat attattacag tccattgatt tttcttgtag    6960
agtggaaaat attattgtgt tttctaaccg taggagttca tgtggtgtta tttattttgg    7020
ataatgtggt gtattttat gagaaatcag gatcgcgtca acatgaaagt ttcatctaat    7080
acattattaa gtgcatcgta gcaacaattc atatattaac tcaaaggtag ctttgaaatt    7140
aagatgcatg tcattaatgc ataatagaga aatcaggtta ccaaattata ttaagcccat    7200
atattaactc aaaggtcata gctttgacaa atgctcctta cagatttctc cttgaaccaa    7260
tttgtaaaat atcctctcct tttttttgc gcgaacgcta aatatccttt gtttaacaac    7320
ctcgtcaatt tgtccatttc atatgtgtga acatccttgt acattctttt ttgtgccgtt    7380
tgaaataaaa ctttgaataa atatgcacaa cttaaatgct taaatgtcaa ttggatttgg    7440
atgaaacaaa accaaagttt tagaatttac gatctatcat tatgaattta tgtatgatat    7500
atcacactct ttctgaataa acttcagaat aatataaatt gcttaattat ggtatacatg    7560
agcatatata gcttgcgcaa atcaaaactg tacagtaggt gtgtgttcaa ttcagaatag    7620
tattctattt cgaatttaaa ttaataatac cttctgtagt aatttctata ttagaaaatt    7680
tatacataca aggagcactg ttaattagct agctagcttt atgggttcca ctaatcaatt    7740
```

<210> SEQ ID NO 7
<211> LENGTH: 10260
<212> TYPE: DNA
<213> ORGANISM: Artificial Sequence
<220> FEATURE:
<223> OTHER INFORMATION: Sources: FMV, CaMV, Oryza sativa

<400> SEQUENCE: 7

```
tatatataat aatgtgctaa actatacagc gtccatgcat ttttattctt catgcctaat      7800
taatttgatt caccattaat taattctacg tacaatgttc gaatgtgtga ctatatatgc      7860
tgcatctgca gttctgcacc tcattcagta ctaaattcaa gttcaggttc attaattaat      7920
tcacttattc cttcattttt cacttccagc taatacaaaa                            7960
acaaatttgt tgtaccacct acctaggggt gacaacactg cacatttggc tatttagggc        60
cacgcatata tgcatgaaaa attgacacac gacgttactt gagaacctat tcatgcaggt       120
ctatgagaaa accccaccaa aaaaaacaga tgtgcaaaat aatgctggat tttcatatgc       180
tataaattaa gtactacttt aatcaaacac cacattgaca cacaatgaca caaattaaat       240
actcttacga attcaagtca tatatactct aatacgcacg tgcagcttgt tactcaaata       300
aagaaacagg gcaatacgga tcagtatatc caaccaggct gcatgtaggc caagaacctg       360
acaattcgtt ttccttggag aaagcaaaga acgtttggaa cgtgtgatgt acatgcagat       420
cgaggaaaat agctaatcct gctctttccc tttccagcac aaaaaaagat tccttcgtag       480
ttcgcactgc atttatactc aaacctgcaa ggctcccaaa cagtttgaac caaggcgagg       540
gaaaaaaaa acatctccat agccaagaga aaacatactg tacatgtcaa gagattccct       600
cttcatattc ttacaatcct atttactcaa attaaatctt catatttcac ttcgtaaatt       660
ccaacggcta atttggtcag cacaaattca gcatctcaat caacacaatt tcaatgcatg       720
aaggcgatca agctcaccac tctcctgcca tacaagatgg accgccaccg cttggaattt       780
ccgcagtgac ggcaacacga ggaagaggca acactagcgg atgtatgaag gagtctgcca       840
agctcggcta tttccggcga gcttgagagt ataatcgaga tagaggccgg tggaaagacg       900
aaaggcggcg tactcttggg cttagtgtgg aggcaacggt ggcggcctcg cggagaggtg       960
acgacacctt ggcttggcat ggcagagttc cacttctcaa cagggatgca tgacactcct      1020
aggtaagaag gcggcggtgc tggtgggtgt gggtggaggc acatggactt ctctcaacaa      1080
taaagttgct ctcgctgtca aactattccc tctgccaagt ttgatcactc aatttcttga      1140
tttggctagt cggataagat agtcaccgac atagccaacc agatgggata cccctttttt      1200
ttttagcatg gagagtggga ccaaatgtcc aagctatctc ccatactccc tatgtccaaa      1260
aaaaaataat atttttttaaa ttcatatcta acatacgaag ataatactct tcgttgaaaa      1320
aaaaacaact tcagaatcta gacacaactt tattttttat aagacggaaa gactgtactc      1380
ctatactcct acatttcacc attttttttcc ccgcgtaaaa acaaaccccc gaattgaccg      1440
tccactgtag catcactcca tcagacttga agcgagtgag agacagagcg ctgcgttaaa      1500
aagaaaagag gaaagaaccg gacgcagagc cctactgtca aactgacaag gcaggaagaa      1560
gaaagggaag ccccccctac caagcccctag cctccttgtc cgtttgctcc ccccagcgc      1620
cacccccgt cgacacgcgt cgcccaccct ctgccattcc ctcttccgcc ctcccagcca      1680
ctactacgct tttactccct gccgcgcgcg cgagatcttc accttcaccg tatccgctcg      1740
cgttttgcac gcagttgatt tgcgctttgt ttttgcatcc tacgaaacta accgcacacc      1800
aatcacctcc tccaccaccg cacagagcta tagctagcga ggagcgtgct acagtgcgct      1860
```

```
gcgcaggaga gagaatcgat cgatggaaga acgcgacagg agcaagctag ccagcctagc    1920
tgtagcgacg tgacagcagt ttgatctttc ttttttttctt atgatggcta agcttatacg   1980
taagccgatc gatcgatggc gagatagatc agagattaat atacaggggt aattaatgta    2040
ctaattacaa ttaagtgtgt ggacgagcga gccgtgtgga gttacagcta gctagcgctt    2100
atgctactcc tacttaaggc gagaccccaa actccaagca tacgatcagg tagccaaacc    2160
acaccaccat aaagctagct tgcaaagggg atagagtagt agagagagag agagaggaga    2220
ggaggaggaa gaagtagggg aggggaagg tggagctgaa gcggatcgag aacaagatca     2280
gccggcaggt gacgttcgcc aagcgcagga acggcctgct caagaaggcc tacgagcact    2340
ccctcctctg cgacgccgag gtcgccctca tcatcttctc cggccgcggc cgcctcttcg    2400
agttctccag ctcatctagg tacgtatagc accaaaccaa cgccgccgcc gccgccggcg    2460
tgcttgttcc ggcgcagcag cgcatcatca tcgatcgatc taagtctaat aagataatca    2520
attaacccta actaaataaa atgataagaa cagtatatat ggttatgatc agtgaaacac    2580
tcgtcgatct gagggaaaat ccggtcgaga tcgagggagt ggggagacaa attgaactgc    2640
aggctagcta atttaatcgt gtcgatcgat ttctagcttt tgttgatctt tatatatacg    2700
aacgcatgca ctttccccctt tgtttttttt tccccttcgat ctgcttggag cacatatgct   2760
atagatcttg gggcatatgt atctgtcagc tttcgagagc ggctatgtcc atcgatccct    2820 ctttttttc tctttctttt tgtagtatca gctgccatgc atatatcaga tttcgttttc     2880
gcgtgctttt agtgcttcac ttatctgttc gccatatctg atttcttctc atcctttgcc    2940
gacgtcgtct gagcagtctg acctccaaga tctggcgaaa taaacctcaa tcgttgctat    3000
ttcttgcctt gaatctgcat aaacatgaca atagatcctt ctatttttt tcttcaagac     3060 aagatcttgc tgtttcttcc cttgctattt ttcattcaaa gattcttctt ttttttctaa    3120
aagaactata tatatgaa tcgagtttca tcttcatcga tctgtctctc tccttttgtt      3180
ttctgtaaac acacacacga gcgtacgtat atatactctc atctctactt ttatcaaaaa    3240
gaaacacaca tgttctagct tcagatccca aaataatcaa acaggaaaat atatataata    3300
tgcaattagt tcagatcccg aggtagattt cttgattatt ccattttcc aaagtgaggc     3360 gcgcgacaac tcgacgcggt tcctctttgc acacacacac agtataactg tacgcaaggg    3420
gtaagaacaa aggagcaatc ccttctgggt tgctgcttgc ttctcccatt tttagctatt    3480
tcagaatttc actttctgag actcatctct ctctctctac cagctgcatt atttcacttc    3540 cctttttttcc catttctgcc tattacacgg atggcctctt tgtggactcg tccaaattga    3600
ggcacggtag ctggtgtcaa aatgaacctg caggcccagc ccggttatgt atatgtatag    3660
ctatatagct tttcttgcaa gaggtatata cactttgtag ttttagccag tggtccagct    3720
agccaaggat ggatatatta tacacacgta tatatagtac atgtatgtac gagtgttaat    3780
taaactcgtt tagttaatttt ccaaagtcct tttttattac tacagctagc ctgatctgtg   3840
ttttagtgtg ttactgttcc attagttact gttctattga agagagcgcg tacacgttgt    3900 tgtttttattt ctctttttcc gatccggtgt tccttttttt tttctttggg tcatcttcct    3960
cgagtcccga gcagtagaaa tactactact gccctgcaaa gcacacacat caagtgatgt    4020
gtttttcttc agagcttcag acgtgtcata tcaagcaggt cagcacgcat tacatgcaat    4080
ataatactcc tatatggaca cgcagaactc actttgatca tgtgtgacca agctggatga    4140
gccgttaatt tgttgttggg acagggtatt gaatcattaa ttgcggtttt tcctcttttt    4200
```

```
cctgtcttgt tctactcaga gaattgaacg gtgaactgta taggcagagc tagtcctgca    4260
tgcatcggtt ttctgaaatt attaactata cacacacatg cacaattgct aaatctggta    4320
tacatgtctt gctgactcac atattcgttc ctcctaatta aagcactcat ttatttattt    4380
tacacggttt tcaatgatat actttaaata ttaatttgtt tgatgttata tttctatgaa    4440
tatgaaatta gcatcatatg aaaatacttt aaaacaaata tagtgatata acatgcataa    4500
tacttagcat atacttgtat gattagcatg gtcattaatc aaaagttgcc gagcttgaat    4560
tttctaaagg acagggtgcc ttgtaatttg ggacaaagaa ccattggaaa acgaacacaa    4620
agaaactttc attacattaa ttatctgaaa aagaaagaaa cttcattaa cctcgtacag     4680 taaatagaaa agaggaacta tgcatgtata acgaaatagc taggatcaca gcaattaatt    4740
agttgttctc tggctttact tttcttttgg agtaacttta attttctctt ggaggatgaa    4800
gtagttaatt atacaggttt ccaattcttg tttggtagat cctttttat gttcctggaa     4860 gagctactat attttgtac ttgagatgga gctgaggtac cgttatctag ctatgtcgca     4920
tctcaaggag ttacgaatta acatatatca ccaatatcac aaaaatgctc catacaaaaa    4980
gatcataaaa attcttgaat ttgcttgctg tgttttttta ctatatatgc ttggaattaa    5040
aaaaatgact gaattaatcg tttgcaatct ttaacggtgc gtgcagtacc aaattggaaa    5100
ggtatccact tgttcaaact taaaaatatt ttttttactg atattactct ctaaaaaggt    5160
gcatgggaaa tgctattgga actactagtt ttcgggacat tataagaaaa tgtatgcata    5220
tatatatata tatatggact tatgatatgg gccagatacc tatatatata gaagatatat    5280
gtgtgctact acctccattc aacaatacaa gcatttgagc cagttctggt caaggatata    5340
aacatcctgc actattagct tgtacttgtc aaattaatga tctctaattc aaactttctt    5400
gctactttac ccccaatcac ccttcccaac catcttaatc tttgctaaac attctagaaa    5460
tgcttattgt tggatggagg aagtagctat taactactcc tatagttttt ttaactacct    5520
catattaatt ttgtaatcct aataaatgca ctatatatgc ccacttttac cgtgtttcca    5580
aactggcatc aagctaaaat gaatgttaat ttagtttccc cataatttta tgagaatcgc    5640
aaaattgtac ctattttaaa caaatcaaag tcactgaaca aatgaacgga ggttaattat    5700
tatattcacc tgatataggc agactaggtt gggctaagag ggacattaat ttgggcatct    5760
aggttttgaa atgggagata tggagagtga accaaaaaaa aactgttagt gaattagtac    5820
atgatatata ctagtattat tagtgggaac ctagagaaat gcaaagaatg ttgcgcaaat    5880
catcattttg tgtaaattaa aatgggatat acactatggg gaactatagc tgagtgtcaa    5940
tccccacctt ttgtttgtaa ttaaacatgt gtttatgcta caaattactc cctccgtact    6000
cataaaggaa gtcgtttagg acaatgttta agtcaaaccct tgggaatata aattatgaat   6060
aactctcaag ttgttgagtt tgaaaatgta aaaaatatat gaatagattt gtcttgaaaa    6120
atactttcat aaaagtatac atatatcact tttcaataaa tattttatag aaacaagaag    6180
tcaaaattgt gttttggaga ccgtgtcact gtccaaaacg acttctttac gagtacggag    6240
ggagtatgtt ctacatattg gctaatattg ttgaacccctt cggatcaatc ttagacacag   6300
tagccatttt acccactgat gcagcaaccc aattaggtat ctactaatta gcatcatagt    6360
gcaaatttgt acttttcaag tggaaaatag aaattatttg tcctccttta ctttaatttc    6420
ttgataatat gatatatgta acataatttc tctttgctcc caagcatata aaaaacttca    6480
atttgatatg tccaaaaaat gtcatatata tagcatgtaa tcctctgtgg caaacacgtt    6540
tttttggctc aaattaagaa gaggaaaaaa tggtatatat gtataaacct aacaaaaatg    6600
```

```
ccccaacaag aatagcttta ttttgtgaac aaggtcatat agaccaggga acaaaaaccc    6660
tgtactgtgc ttctattttg ctatgcattt tggataagtg attctacaga aatatgacta    6720
tataggagat attctcaaat ctgatctttt ctattaatta gcccatacga tatgaagaca    6780
tatcttcctc tgttctgatt ctatttgttg tgctaagata gtctacagga tttgctaggt    6840
tgccacctgc cgtcaacaaa attcagctca tcagattttg ttatagttgc tagcacagtt    6900
atattatacg tatatctctt ttgagaatat attattacag tccattgatt tttcttgtag    6960
agtggaaaat attattgtgt tttctaaccg taggagttca tgtggtgtta tttattttgg    7020
ataatgtggt gtattttat gagaaatcag gatcgcgtca acatgaaagt ttcatctaat     7080
acattattaa gtgcatcgta gcaacaattc atatattaac tcaaaggtag ctttgaaatt    7140
aagatgcatg tcattaatgc ataatagaga atcaggttca ccaaattata ttaagcccat    7200
atattaactc aaaggtcata gctttgacaa atgctcctta cagatttctc cttgaaccaa    7260
tttgtaaaat atcctctcct ttttttttgc gcgaacgcta aatatccttt gtttaacaac    7320
ctcgtcaatt tgtccatttc atatgtgtga acatccttgt acattctttt ttgtgccgtt    7380
tgaaataaaa ctttgaataa atatgcacaa cttaaatgct taaatgtcaa ttggatttgg    7440
atgaaacaaa accaaagttt tagaatttac gatctatcat tatgaattta tgtatgatat    7500
atcacactct ttctgaataa acttcagaat aatataaatt gcttaattat ggtatacatg    7560
agcatatata gcttgcgcaa atcaaaactg tacagtaggt gtgtgttcaa ttcagaatag    7620
tattctattt cgaatttaaa ttaataatac cttctgtagt aatttctata ttagaaaatt    7680
tatacataca aggagcactg ttaattagct agctagcttt atgggttcca ctaatcaatt    7740
tatatataat aatgtgctaa actatacagc gtccatgcat ttttattctt catgcctaat    7800
taatttgatt caccattaat taattctacg tacaatgttc gaatgtgtga ctatatatgc    7860
tgcatctgca gttctgcacc tcattcagta ctaaattcaa gttcaggttc attaattaat    7920
tcacttattc cttcattttt cacttccagc taatacaaaa ccatggattt gagcaatagc    7980
tcacctgtca tcaccgatcc ggtggcgatc agccagcagt tgttgggcgg cctgccttca    8040
aatctgatgc agttttcagt catgcccggt ggctactcca gctctggcat gaacgttggt    8100
gtcagtaggc tcaaaatcga ggaagtcctt gtcaatggac tgcttgatgc catgaaatcc    8160
tcgtcacctc gcaggaggct gaatgtagca tttggcgagg acaattcatc tgaagaagaa    8220
gaccctgctt acagcgcttg gatggcaaaa tgtccttctg ctttggcttc cttcaagcaa    8280
attgtagcca gtgcacaagg gaagaagatt gctgtgtttc tagactatga cggcacactg    8340
tcgcctattg tggatgatcc tgacaaagca gtgatgtctc ccgtgatgag agctgctgtg    8400
agaaatgttg cgaagtactt ccccactgca attgtcagcg gaaggtcccg caataaggtg    8460
tttgaatttg taaaactgaa ggagctttat tatgctggaa gtcatggtat ggacataatg    8520
gcaccttcag caaatcatga gcacagtgct gaaaagagca acaggccaa tctcttccaa     8580 cctgcacacg actttctgcc aatgatcgat gaggttacca agtccctctt gcaagttgtc    8640
agtggaattg aaggtgcaac tgttgagaac aacaaattct gcgtttctgt acattatcgc    8700
aacgttgcag agaaggattg gaactggtc gcacggctcg taaacgaagt gctggaggct     8760
tttcctcgtc tcaaagtaac caatggacga atggtttag aggttcgtcc ggtgatcgac     8820
tgggacaagg gaaaggctgt ggagtttctg ctccagtcac tcgggctaaa tgactctgaa    8880
aatgtgatcc ccatctacat tggagacgac agaactgacg aagacgcttt caaggtactt    8940
```

```
cgacagcgaa attgcggtta tggaatacta gtttcacagg ttcccaagga aactgaagcc    9000
ttctactcgc tgagagatcc atctgaagtg atggagttcc tcaatttctt ggtgagatgg    9060
aagaagcact cagtgtgagc tctgtgtgtg ttcagttcag gcttcaggct tcagagaagc    9120
caatgcaaac agtgtcctgt aatccagtaa ttacagggca tatgtaatgt aatgtaatgt    9180
aatccctgat ctatattttg ctaagtacgt gcgtgctctc ttacgacctt ctcccccaaa    9240
cagttaatca ggggaataat aatttcgttt gatgcacgta ctgtatgtct gtatctgtca    9300
ctgtatcgta ggaccgtcca tgtataacaa tttccgtttt ggatgtggta acaagttaat    9360
tggcacttaa atttatattt gtgatgatct gggagagtac ctaatctcaa aaacttgtgg    9420
agattatgtt agggagtagt gcaagaaatg ttttaagacg gcagctgtta tctcatgaga    9480
tattgataat gatgttgtct ctgctgctgt cgcgatcgcc aaattatgct gttttttag    9540 attataccga aatatgctga tggatacgtg gttttgatct gtggccgttg cgaagtaagc    9600 gcgattatt tctgcaggcg ttcgaatcac gttttactgt tggcggtagt tactgcacgg    9660
tgactgttcg acgaaatgcc aaaacaaccc gcaggctgca gccagtcgac aagtgcggcg    9720
gccgtcgccc gatcgcgcgg ctagctagta gctgtcggca ccgccggttg gttacccgca    9780
ccaccgggcc ctcgccgtcg ccgtcggcg tccttgcgct gcacggacgc gtcacgcgca    9840
ctgccgcctg cctgcctttg cgctgtcggg cgggcgcgcg ggcagaaagc gaccgcgcgc    9900
gcggaggggg gcgccctctt ccacacgcag cgtagcggag gcggcactgg cacggaactc    9960
ccaccgagcc gacgggcccg cccgcccggc ggccggccgc gccgcgccag cagctggacg   10020
aacatccgtg cacagcgcgc gcgcaggcga ggcgcggcgc gacgtggtgc ttcggctcgc   10080
gtcctcgcgt acgtacgccg ccacggccac caccgccatc agtgtcgcgt tttgcactta   10140
ctcatactga acactggaca gagcacgata agcagcggtg tttgtaccgc ccggcccaag   10200
ggacggcaga ctcgccggca gaaaatcaaa ttaaaattgc atagttgcaa gtattagcag   10260
```

<210> SEQ ID NO 8
<211> LENGTH: 9156
<212> TYPE: DNA
<213> ORGANISM: Artificial Sequence
<220> FEATURE:
<223> OTHER INFORMATION: Sources: FMV, CaMV, Oryza sativa

<400> SEQUENCE: 8

```
acaaatttgt tgtaccacct acctaggggt gacaacactg cacatttggc tatttagggc      60
cacgcatata tgcatgaaaa attgacacac gacgttactt gagaacctat tcatgcaggt     120
ctatgagaaa accccaccaa aaaaaacaga tgtgcaaaat aatgctggat tttcatatgc     180
tataaattaa gtactacttt aatcaaacac cacattgaca cacaatgaca caaattaaat     240
actcttacga attcaagtca tatatactct aatacgcacg tgcagcttgt tactcaaata     300
aagaaacagg gcaatacgga tcagtatatc caaccaggct gcatgtaggc caagaacctg     360
acaattcgtt ttccttggag aaagcaaaga acgtttggaa cgtgtgatgt acatgcagat     420
cgaggaaaat agctaatcct gctctttccc tttccagcac aaaaaaagat tccttcgtag     480
ttcgcactgc atttatactc aaacctgcaa ggctcccaaa cagtttgaac caaggcgagg     540
gaaaaaaaaa acatctccat agccaagaga aaacatactg tacatgtcaa gagattccct     600
cttcatattc ttacaatcct atttactcaa attaaatctt catatttcac ttcgtaaatt     660
ccaacggcta atttggtcag cacaaattca gcatctcaat caacacaatt tcaatgcatg     720
aaggcgatca agctcaccac tctcctgcca tacaagatgg accgccaccg cttggaattt     780
```

```
ccgcagtgac ggcaacacga ggaagaggca acactagcgg atgtatgaag gagtctgcca      840
agctcggcta tttccggcga gcttgagagt ataatcgaga tagaggccgg tggaaagacg      900
aaaggcggcg tactcttggg cttagtgtgg aggcaacggt ggcggcctcg cggagaggtg      960
acgcaccctt ggcttggcat ggcagagttc cacttctcaa cagggatgca tgacactcct     1020
aggtaagaag gcggcggtgc tggtgggtgt gggtggaggc acatggactt ctctcaacaa     1080
taaagttgct ctcgctgtca aactattccc tctgccaagt tgatcactc aatttcttga      1140 tttggctagt cggataagat agtcaccgac atagccaacc agatgggata acccctttt      1200 ttttagcatg gagagtggga ccaaatgtcc aagctatctc ccatactccc tatgtccaaa     1260
aaaaaataat attttttaaa ttcatatcta acatacgaag ataatactct tcgttgaaaa     1320
aaaaacaact tcagaatcta gacacaactt tatttttat aagacggaaa gactgtactc      1380
ctatactcct acatttcacc attttttcc ccgcgtaaaa acaaacccc gaattgaccg       1440 tccactgtag catcactcca tcagacttga agcgagtgag agacagagcg ctgcgttaaa     1500
aagaaaagag gaaagaaccg gacgcagagc cctactgtca aactgacaag gcaggaagaa     1560
gaaagggaag cccccctac caagccctag cctccttgtc cgtttgctcc ccccagcgc       1620 caccccccgt cgacacgcgt cgcccaccct ctgccattcc ctcttccgcc ctcccagcca     1680
ctactacgct tttactccct gccgcgcgcg cgagatcttc accttcaccg tatccgctcg     1740
cgttttgcac gcagttgatt tgcgctttgt ttttgcatcc tacgaaacta accgcacacc     1800
aatcacctcc tccaccaccg cacagagcta tagctagcga ggagcgtgct acagtgcgct     1860
gcgcaggaga gagaatcgat cgatggaaga acgcgacagg agcaagctag ccagcctagc     1920
tgtagcgacg tgacagcagt ttgatctttc ttttttctt atgatggcta agcttatacg      1980
taagccgatc gatcgatggc gagatagatc agagattaat atacagggt aattaatgta      2040 ctaattacaa ttaagtgtgt ggacgagcga gccgtgtgga gttacagcta gctagcgctt     2100
atgctactcc tacttaaggc gagaccccaa actccaagca tacgatcagg tagccaaacc     2160
acaccaccat aaagctagct tgcaaagggg atagagtagt agagagagag agagaggaga     2220
ggaggaggaa gaagtagggg aggggggaagg tggagctgaa gcggatcgag aacaagatca     2280
gccggcaggt gacgttcgcc aagcgcagga acggcctgct caagaaggcc tacgagcact     2340
ccctcctctg cgacgccgag gtcgccctca tcatcttctc cggccgcggc cgcctcttcg     2400
agttctccag ctcatctagg tacgtatagc accaaaccaa cgccgccgcc gccgccggcg     2460
tgcttgttcc ggcgcagcag cgcatcatca tcgatcgatc taagtctaat aagataatca     2520 attaaccta actaaataaa atgataagaa cagtatatat ggttatgatc agtgaaacac      2580
tcgtcgatct gagggaaaat ccggtcgaga tcgagggagt ggggagacaa attgaactgc     2640
aggctagcta atttaatcgt gtcgatcgat ttctagcttt tgttgatctt tatatatacg     2700
aacgcatgca ctttccccctt tgtttttttt tcccttcgat ctgcttggag cacatatgct     2760
atagatcttg gggcatatgt atctgtcagc tttcgagagc ggctatgtcc atcgatccct     2820 ctttttttc tctttctttt tgtagtatca gctgccatgc atatatcaga tttcgttttc      2880
gcgtgctttt agtgcttcac ttatctgttc gccatatctg atttcttctc atcctttgcc     2940
gacgtcgtct gagcagtctg acctccaaga tctggcgaaa taaacctcaa tcgttgctat     3000
ttcttgcctt gaatctgcat aaacatgaca atagatcctt ctattttttt tcttcaagac     3060
aagatcttgc tgtttcttcc cttgctattt ttcattcaaa gattcttctt ttttttctaa     3120
```

-continued

```
aagaactata tatatatgaa tcgagtttca tcttcatcga tctgtctctc tccttttgtt      3180
ttctgtaaac acacacacga gcgtacgtat atatactctc atctctactt ttatcaaaaa      3240
gaaacacaca tgttctagct tcagatccca aaataatcaa acaggaaaat atatataata      3300
tgcaattagt tcagatcccg aggtagattt cttgattatt tccattttcc aaagtgaggc      3360
gcgcgacaac tcgacgcggt tcctctttgc acacacacac agtataactg tacgcaaggg      3420
gtaagaacaa aggagcaatc ccttctgggt tgctgcttgc ttctcccatt tttagctatt      3480
tcagaatttc actttctgag actcatctct ctctctctac cagctgcatt atttcacttc      3540
cctttttttcc catttctgcc tattacacgg atggcctctt tgtggactcg tccaaattga      3600
ggcacggtag ctggtgtcaa aatgaacctg caggcccagc ccggttatgt atatgtatag      3660
ctatatagct tttcttgcaa gaggtatata cactttgtag ttttagccag tggtccagct      3720
agccaaggat ggatatatta tacacacgta tatatagtac atgtatgtac gagtgttaat      3780
taaactcgtt tagttaattt ccaaagtcct tttttattac tacagctagc ctgatctgtg      3840
ttttagtgtg ttactgttcc attagttact gttctattga agagagcgcg tacacgttgt      3900
tgttttattt ctcttttttcc gatccggtgt tccttttttt tttctttttgg tcatcttcct      3960
cgagtcccga gcagtagaaa tactactact gccctgcaaa gcacacacat caagtgatgt      4020
gtttttcttc agagcttcag acgtgtcata tcaagcaggt cagcacgcat tacatgcaat      4080
ataatactcc tatatggaca cgcagaactc actttgatca tgtgtgacca agctggatga      4140
gccgttaatt tgttgttggg acagggtatt gaatcattaa ttgcggtttt tcctcttttt      4200
cctgtcttgt tctactcaga gaattgaacg gtgaactgta taggcagagc tagtcctgca      4260
tgcatcggtt ttctgaaatt attaactata cacacacatg cacaattgct aaatctggta      4320
tacatgtctt gctgactcac atattcgttc ctcctaatta aagcactcat ttatttattt      4380
tacacggttt tcaatgatat actttaaata ttaatttgtt tgatgttata tttctatgaa      4440
tatgaaatta gcatcatatg aaaatacttt aaaacaaata tagtgatata acatgcataa      4500
tacttagcat atacttgtat gattagcatg gtcattaatc aaaagttgcc gagcttgaat      4560
tttctaaagg acagggtgcc ttgtaatttg ggacaaagaa ccattggaaa acgaacacaa      4620
agaaactttc attacattaa ttatctgaaa aagaaagaaa ctttcattaa cctcgtacag      4680
taaatagaaa agaggaacta tgcatgtata acgaaatagc taggatcaca gcaattaatt      4740
agttgttctc tggctttact tttcttttgg agtaacttta attttctttt ggaggatgaa      4800
gtagttaatt atacaggttt ccaattcttg tttggtagat ccttttttat gttcctggaa      4860
gagctactat attttgtac ttgagatgga gctgaggtac cgttatctag ctatgtcgca      4920
tctcaaggag ttacgaatta acatatatca ccaatatcac aaaaatgctc atacaaaaa      4980
gatcataaaa attcttgaat ttgcttgctg tgttttttta ctatatatgc ttggaattaa      5040
aaaaatgact gaattaatcg tttgcaatct ttaacggtgc gtgcagtacc aaattggaaa      5100
ggtatccact tgttcaaact taaaatatatt tttttactg atattactct ctaaaaaggt      5160
gcatgggaaa tgctattgga actactagtt ttcgggacat tataagaaaa tgtatgcata      5220
tatatatata tatatggact tatgatatgg gccagatacc tatatatata gaagatatat      5280
gtgtgctact acctccattc aacaatacaa gcatttgagc cagttctggt caaggatata      5340
aacatcctgc actattagct tgtacttgtc aaattaatga tctctaattc aaactttctt      5400
gctactttac ccccaatcac ccttcccaac catcttaatc tttgctaaac attctagaaa      5460
tgcttattgt tggatggagg aagtagctat taactactcc tatagttttt ttaactacct      5520
```

```
catattaatt ttgtaatcct aataaatgca ctatatatgc ccacttttac cgtgtttcca   5580
aactggcatc aagctaaaat gaatgttaat ttagtttccc cataatttta tgagaatcgc   5640
aaaattgtac ctattttaaa caaatcaaag tcactgaaca aatgaacgga ggttaattat   5700
tatattcacc tgatataggc agactaggtt gggctaagag ggacattaat ttgggcatct   5760
aggttttgaa atgggagata tggagagtga accaaaaaaa aactgttagt gaattagtac   5820
atgatatata ctagtattat tagtgggaac ctagagaaat gcaagaatg ttgcgcaaat    5880 catcattttg tgtaaattaa aatgggatat acactatggg gaactatagc tgagtgtcaa   5940
tccccacctt ttgtttgtaa ttaaacatgt gtttatgcta caaattactc cctccgtact   6000
cataaaggaa gtcgtttagg acaatgttta agtcaaacct tgggaatata aattatgaat   6060
aactctcaag ttgttgagtt tgaaaatgta aaaaatatat gaatagattt gtcttgaaaa   6120
atactttcat aaaagtatac atatatcact tttcaataaa tattttatag aaacaagaag   6180
tcaaaattgt gttttggaga ccgtgtcact gtccaaaacg acttctttac gagtacggag   6240
ggagtatgtt ctacatattg gctaatattg ttgaacccct cggatcaatc ttagacacag   6300
tagccatttt acccactgat gcagcaaccc aattaggtat ctactaatta gcatcatagt   6360
gcaaatttgt acttttcaag tggaaaatag aaattatttg tcctccttta ctttaatttc   6420
ttgataatat gatatatgta acataatttc tctttgctcc caagcatata aaaaacttca   6480
atttgatatg tccaaaaaat gtcatatata tagcatgtaa tcctctgtgg caaacacgtt   6540
tttttggctc aaattaagaa gaggaaaaaa tggtatatat gtataaacct aacaaaaatg   6600
ccccaacaag aatagcttta ttttgtgaac aaggtcatat agaccaggga acaaaaaccc   6660
tgtactgtgc ttctattttg ctatgcattt tggataagtg attctacaga aatatgacta   6720
tataggagat attctcaaat ctgatctttt ctattaatta gcccatacga tatgaagaca   6780
tatcttcctc tgttctgatt ctatttgttg tgctaagata gtctacagga tttgctaggt   6840
tgccacctgc cgtcaacaaa attcagctca tcagattttg ttatagttgc tagcacagtt   6900
atattatacg tatatctctt ttgagaatat attattacag tccattgatt tttcttgtag   6960
agtggaaaat attattgtgt tttctaaccg taggagttca tgtggtgtta tttatttttgg  7020 ataatgtggt gtattttat gagaaatcag gatcgcgtca acatgaaagt ttcatctaat    7080
acattattaa gtgcatcgta gcaacaattc atatattaac tcaaaggtag cttttgaaatt  7140 aagatgcatg tcattaatgc ataatagaga aatcaggtta ccaaattata ttaagcccat   7200
atattaactc aaaggtcata gctttgacaa atgctcctta cagatttctc cttgaaccaa   7260
tttgtaaaat atcctctcct tttttttttgc gcgaacgcta aatatccttt gtttaacaac   7320
ctcgtcaatt tgtccatttc atatgtgtga acatccttgt acattctttt ttgtgccgtt   7380
tgaaataaaa ctttgaataa atatgcacaa cttaaatgct taaatgtcaa ttggatttgg   7440
atgaaacaaa accaaagttt tagaatttac gatctatcat tatgaattta tgtatgatat   7500
atcacactct ttctgaataa acttcagaat aatataaatt gcttaattat ggtatacatg   7560
agcatatata gcttgcgcaa atcaaaactg tacagtaggt gtgtgttcaa ttcagaatag   7620
tattctattt cgaatttaaa ttaataatac cttctgtagt aatttctata ttagaaaatt   7680
tatacataca aggagcactg ttaattagct agctagcttt atgggttcca ctaatcaatt   7740
tatatataat aatgtgctaa actatacagc gtccatgcat ttttattctt catgcctaat   7800
taatttgatt caccattaat taattctacg tacaatgttc gaatgtgtga ctatatatgc   7860
```

| | |
|---|---|
| tgcatctgca gttctgcacc tcattcagta ctaaattcaa gttcaggttc attaattaat | 7920 |
| tcacttattc cttcattttt cacttccagc taatacaaaa ccatggatat atgagctctg | 7980 |
| tgtgtgttca gttcaggctt caggcttcag agaagccaat gcaaacagtg tcctgtaatc | 8040 |
| cagtaattac agggcatatg taatgtaatg taatgtaatc cctgatctat attttgctaa | 8100 |
| gtacgtgcgt gctctcttac gaccttctcc cccaaacagt taatcagggg aataataatt | 8160 |
| tcgtttgatg cacgtactgt atgtctgtat ctgtcactgt atcgtaggac cgtccatgta | 8220 |
| taacaatttc cgttttggat gtggtaacaa gttaattggc acttaaattt atatttgtga | 8280 |
| tgatctggga gagtacctaa tctcaaaaac ttgtggagat tatgttaggg agtagtgcaa | 8340 |
| gaaatgtttt aagacggcag ctgttatctc atgagatatt gataatgatg ttgtctctgc | 8400 |
| tgctgtcgcg atcgccaaat tatgctgttt ttttagatta taccgaaata tgctgatgga | 8460 |
| tacgtggttt tgatctgtgg ccgttgcgaa gtaagcgcga tttatttctg caggcgttcg | 8520 |
| aatcacgttt tactgttggc ggtagttact gcacggtgac tgttcgacga atgccaaaa | 8580 |
| caacccgcag gctgcagcca gtcgacaagt gcggcggccg tcgcccgatc gcgcggctag | 8640 |
| ctagtagctg tcggcaccgc cggttggtta cccgcaccac cgggccctcg ccgtcgccgt | 8700 |
| cggccgtcct tgcgctgcac ggacgcgtca cgcgcactgc cgcctgcctg cctttgcgct | 8760 |
| gtcgggcggg cgcgcgggca gaaagcgacc gcgcgcgcgg agggggggcgc cctcttccac | 8820 |
| acgcagcgta gcggaggcgg cactggcacg gaactcccac cgagccgacg ggcccgcccg | 8880 |
| cccggcggcc ggccgcgccg cgccagcagc tggacgaaca tccgtgcaca gcgcgcgcgc | 8940 |
| aggcgaggcg cggcgcgacg tggtgcttcg gctcgcgtcc tcgcgtacgt acgccgccac | 9000 |
| ggccaccacc gccatcagtg tcgcgttttg cacttactca tactgaacac tggacagagc | 9060 |
| acgataagca gcgtgtttg taccgcccgg cccaagggac ggcagactcg ccggcagaaa | 9120 |
| atcaaattaa aattgcatag ttgcaagtat tagcag | 9156 |

<210> SEQ ID NO 9
<211> LENGTH: 5607
<212> TYPE: DNA
<213> ORGANISM: Artificial Sequence
<220> FEATURE:
<223> OTHER INFORMATION: sources: FMV, CaMV, Oryza sativa

<400> SEQUENCE: 9

| | |
|---|---|
| agctgcttgt ggggaccaga caaaaaagga atggtgcaga attgttaggc gcacctacca | 60 |
| aaagcatctt tgcctttatt gcaaagataa agcagattcc tctagtacaa gtggggaaca | 120 |
| aaataacgtg gaaagagct gtcctgacag cccactcact aatgcgtatg acgaacgcag | 180 |
| tgacgaccac aaaactcgag actttcaac aaagggtaat atccggaaac ctcctcggat | 240 |
| tccattgccc agctatctgt cactttattg tgaagatagt ggaaaggaa ggtggctcct | 300 |
| acaaatgcca tcattgcgat aaaggaaagg ctatcgttga agatgcctct ccgacagtg | 360 |
| gtcccaaaga tggacccca cccacgagga gcatcgtgga aaagaagac gttccaacca | 420 |
| cgtcttcaaa gcaagtggat tgatgtgata tctccactga cgtaagggat gacgaacaat | 480 |
| cccactatcc ttcggtaccg gaccctcgtc gccgtcgttg gctcggcgtc tcgccgccgt | 540 |
| ttaccttcc cgtttccgag cccggagagg gtatcgcttg ccttgatgga cgcgcgcgtg | 600 |
| ggccggggga atgtggtttt ggttgactcg cgcctgtctt gggccgtgat tgattcagcc | 660 |
| cagtctgcca gtttgctgtc ttgaattctc ggaggcccat gtagagaaat ccatctatcc | 720 |
| acgtggaaac gtgggccatc gccattgagc gaaatcagat tagaaaaagt ataatttgac | 780 |

```
tccctcaact atcgcccgag tatgattcat atcctcccac tacaaaacag atacatcgac     840
ccctacaatt atcaaaacca atgcaaacaa tgtccctcgg tggttttggc tgaagtgtcg     900
cctacgtggc ggttttggct gagtctttgt cctacgtggc gcgtggcatt agaataaaaa     960
aatatggcac ccatatgtca ttcataaaaa aatatattat gggagccaca tgtcatcctt    1020
cctctccttc ccttcttcct cccgtctttc tctctcccTT atctctctcc cagcctttct    1080
gatcgaagcg gcggtggcgg cggtcgggag cagctgcggt ggtggtgggg agcggcgacg    1140
atggcggtcg ggagcggcgg ctgtggcgat ggggacgagg tggttgggag cagcggcggt    1200
agcagtgggg acaaggcggt gggaaggggc ggacgtgggc cagtgctcgg gcttgacggc    1260
ggtgcagagt agggcgacct cggtgagcct cagcatgtcg ccgtggcggt cccggtcggt    1320
gacgatctcc acatcgagga tgtctgtcga ccactcatgg ctcagcgcca gttgcgccca    1380
ctccgccagg tcgtcgtcct cgtcgacggg gaccttcccg gtgaccacct cgagcagcac    1440
gagcccgagg cagaacacgt cggcatggga ggacagccgc ctcccgcacg tgaactctga    1500
gcacttggcc gccgcgagac gatgaccgtg gtgcagaagc agcgggtaga acccgtggtc    1560
ggtcaacttg gccaccggca ccacgtcgcc gccgctgccg ggcgccggga agacgacgag    1620
cacgttcgac gacttgaggt tgccgtgcgg cggccggtgg acgaggtcgc ctggctctgg    1680
acacgcgcgt gcaccaccac cggacgccgc cgtcgctccc taccgtcgtc cccaccgcca    1740
ccgccgccgc tccagagaga gagataaggg agagagaggg ggaggaagaa gggaaagaga    1800
gggaagatga catgtgcgtc ccacaatact ttttattgtg tgaatgacat atgggtccta    1860
catatttttt tttgttttta ttctaatgca acgtaagcgc tacgtaggac taagactggg    1920
tcaatactgc cgcgtaggcg ccacgtcagc caaaaccgct tccaaaacca cacaggaata    1980
tattttgcac cgatttTaat agttagagga gtcaatatac ctggttttgt ggttggaggt    2040
tatgaatcat actcgaggca tagttgaggg aggccgtgtt tagttgcaaa ttttctcttc    2100
aaacttcaaa cttttccatc acatcaaaac tttcgtacac acacaaactt ccaactttt    2160 cgtcacattg ttccaatttc aaccaaactt ccaattttga actaaacagc agccggagtc    2220
aaagtacttt ttccaatcag atttgagccg atcatgattt gaactcttca aaactactag    2280
taattttcag ttcgaattca tgaaagttca catcatgcta tacctacacc tagcatgtat    2340
aggactggac tgtattggta ctagtactac agagtatcat agccgtacgg gtatcataga    2400
caagacaata cagaaagtac agtgtcctgg aaacgtcaat gatcaaatcg accatcaatc    2460
cctcctcacc tttcggcttt ccatcaaccg gaatcaaatc ggatagcgaa gcaaagccaa    2520
cggaagcaaa gtaaacaggg cattgccgtt tctggagcac ccctactgaa ccgcctcgaa    2580
agcctcctca tcaccattcc tcttcctccc aaggcgaact cctttactcc tcctccaccc    2640
ccaccgcctc gcccatccac accgacgcct aggtagcgct tgttcttgtt gttgttgtta    2700
ttgttggctt cgctttgctg ctaagctagc tggaggaagg aggaggagga ggaggaggcg    2760
ggaaggggcg cgggaagatc gagatcaaga ggatcgagaa ctccaccaac cgccaggtga    2820
ccttctccaa gcgcaggagc gggatcctca agaaggcccg cgagatcagc gtcctgtgcg    2880
acgccgaggt cggcgtcgtc atcttctcca gcgccggcaa gctcttagac tactgatccc    2940
ctaagacctc gtgcgtcccc ccctcttctc ctcccccTgg ttcttttgca cataatattt    3000
ttcagtgtac tctttgtcta gatgataagg tatatatgca agaatcgttt tgatgcaaca    3060
actaggttga agatttttac tctactcccc aaaaaaaggg aaaagggaga tttttactct    3120
```

```
accaacttgc caggaccgga actgtgtttt tgtattggtt aaagtcagtt tcttttgcag    3180
gaaatgccat gtccttactc ttttcctaa aatcggtttt gagttatgct gatatagtat    3240
cttgaaccac tcgcatctgt tgcactgaca tgcttgatta accttccaat ggtgggacat    3300
gtataaggct atcaagaaac catggatttg agcaatagct cacctgtcat caccgatccg    3360
gtggcgatca gccagcagtt gttgggcggc ctgccttcaa atctgatgca gttttcagtc    3420
atgcccggtg gctactccag ctctggcatg aacgttggtg tcagtaggct caaaatcgag    3480
gaagtccttg tcaatggact gcttgatgcc atgaaatcct cgtcacctcg caggaggctg    3540
aatgtagcat ttggcgagga caattcatct gaagaagaag accctgctta cagcgcttgg    3600
atggcaaaat gtccttctgc tttggcttcc ttcaagcaaa ttgtagccag tgcacaaggg    3660
aagaagattg ctgtgtttct agactatgac ggcacactgt cgcctattgt ggatgatcct    3720
gacaaagcag tgatgtctcc cgtgatgaga gctgctgtga aaatgttgc gaagtacttc    3780 cccactgcaa ttgtcagcgg aaggtcccgc aataaggtgt ttgaatttgt aaaactgaag    3840
gagctttatt atgctggaag tcatggtatg acataatgg caccttcagc aaatcatgag    3900
cacagtgctg aaaagagcaa acaggccaat ctcttccaac ctgcacacga ctttctgcca    3960
atgatcgatg aggttaccaa gtccctcttg caagttgtca gtggaattga aggtgcaact    4020
gttgagaaca acaaattctg cgtttctgta cattatcgca acgttgcaga gaaggattgg    4080
aaactggtcg cacggctcgt aaacgaagtg ctggaggctt ttcctcgtct caaagtaacc    4140
aatggacgaa tggttttaga ggttcgtccg gtgatcgact gggacaaggg aaaggctgtg    4200
gagtttctgc tccagtcact cgggctaaat gactctgaaa atgtgatccc catctacatt    4260
ggagacgaca gaactgacga agacgctttc aaggtacttc gacagcgaaa ttgcggttat    4320
ggaatactag tttcacaggt tcccaaggaa actgaagcct tctactcgct gagagatcca    4380
tctgaagtga tggagttcct caatttcttg gtgagatgga agaagcactc agtgtgagct    4440
cgctgctagg tagccccgcc acttagatca gttatctcat ccactgatcc accactggat    4500
tgaatgtcct agtgcattgt caactgtatc cctgttttca tgtctgtttc gatgaactat    4560
tgagcatgtc atatgtgagt tgcttttgtgt gccaatatat agtctgtctc tagtacaagc    4620
tctgtgcttg ccattctgcc tcgctgtaga tagcaccagc aatggagcta gctcagatat    4680
cagtaacttc gtgcaagctg caaggtatgc ttgtgttatc accgcatttg tcagatggtg    4740
aatagtagtt tgtgattgta acaaacaatt tatgcaagct tggtttcatg ctaatgtcgt    4800
ttcacttgca tttcaacaca tgatatactg tcagttactg agttacatga ctctgaggct    4860
ctgagcatca gttagctacc acttacaaat taaagtacag tatatattat gcataatatc    4920
attagcattc caacacaaag acagtgatac actgtcattt acatcaacta ttggtgttga    4980
ctaactctga acatcagttg gtctgcattc gttgcaattt tacatgctgc aataaactgc    5040
agcattgcag cctgtaaaat tgcagatcga tcgttgtctc caaactcaaa acatatttct    5100
cgttgcatcc atcaacgatt gataccttg ccctcaccgg agcaagtcgc cgaagtccaa    5160
gaacgggggg ccgctcagca cggacgaggc gctgaaattg gcttcgcctt cgtcgaacgc    5220
gatcctctgg ccgtacggct gcggccgttc cggcaggtcg ggcacgtcct tgtcgccctc    5280
caggatcctc agcgcctccg gcttggtggg gcggcacgcc acggtgacgt gcgcgcacag    5340
gatcccgacg agcacgaacc tctcgaaggc gtgcaccccg gcggggccct cccgctcgcg    5400
cagcgccgcg gcgaccacct ccgccgcgcg cccggccctg acgagcgccc acgcccagtc    5460
ggtgatcagc acgacgccgg aggggtcgga caggtcgagc gcgcgccggc cgctcaacac    5520
```

-continued

| | |
|---|---|
| ctccagcacc agcacgccga agctgtacac gtcgctcttc tcggttagct gcccgttgag | 5580 |
| cgcgtagtca ggcgtcagct agctatc | 5607 |

<210> SEQ ID NO 10
<211> LENGTH: 3494
<212> TYPE: DNA
<213> ORGANISM: Artificial Sequence
<220> FEATURE:
<223> OTHER INFORMATION: Sources: Zea mays, Escherichia coli,
      Agrobacterium tumefaciens

<400> SEQUENCE: 10

| | |
|---|---|
| ctgcagtgca gcgtgacccg gtcgtgcccc tctctagaga taatgagcat tgcatgtcta | 60 |
| agttataaaa aattaccaca tattttttt gtcacacttg tttgaagtgc agtttatcta | 120 |
| tctttataca tatatttaaa ctttactcta cgaataatat aatctatagt actacaataa | 180 |
| tatcagtgtt ttagagaatc atataaatga acagttagac atggtctaaa ggacaattga | 240 |
| gtattttgac aacaggactc tacagtttta tctttttagt gtgcatgtgt tctcctttt | 300 |
| ttttgcaaat agcttcacct atataatact tcatccattt tattagtaca tccatttagg | 360 |
| gtttagggtt aatggttttt atagactaat tttttagta catctatttt attctatttt | 420 |
| agcctctaaa ttaagaaaac taaaactcta ttttagtttt tttatttaat aatttagata | 480 |
| taaaatagaa taaaataaag tgactaaaaa ttaaacaaat acccttaag aaattaaaaa | 540 |
| aactaaggaa acattttct tgtttcgagt agataatgcc agcctgttaa acgccgtcga | 600 |
| cgagtctaac ggacaccaac cagcgaacca gcagcgtcgc gtcgggccaa gcgaagcaga | 660 |
| cggcacggca tctctgtcgc tgcctctgga cccctctcga gagttccgct ccaccgttgg | 720 |
| acttgctccg ctgtcggcat ccagaaattg cgtggcggag cggcagacgt gagccggcac | 780 |
| ggcaggcggc ctcctcctcc tctcacggca ccggcagcta cggggattc ctttcccacc | 840 |
| gctccttcgc tttcccttcc tcgcccgccg taataaatag acaccccctc cacaccctct | 900 |
| ttccccaacc tcgtgttgtt cggagcgcac acacacacaa ccagatctcc cccaaatcca | 960 |
| cccgtcggca cctccgcttc aaggtacgcc gctcgtcctc ccccccccc cctctctacc | 1020 |
| ttctctagat cggcgttccg gtccatggtt agggcccggt agttctactt ctgttcatgt | 1080 |
| ttgtgttaga tccgtgtttg tgttagatcc gtgctgctag cgttcgtaca cggatgcgac | 1140 |
| ctgtacgtca gacacgttct gattgctaac ttgccagtgt ttctcttgg ggaatcctgg | 1200 |
| gatggctcta gccgttccgc agacgggatc gatttcatga tttttttgt ttcgttgcat | 1260 |
| aggggtttggt ttgcccttt cctttatttc aatatatgcc gtgcacttgt ttgtcgggtc | 1320 |
| atcttttcat gctttttttt gtcttggttg tgatgatgtg gtctggttgg gcggtcgttc | 1380 |
| tagatcggag tagaattctg tttcaaacta cctggtggat ttattaattt tggatctgta | 1440 |
| tgtgtgtgcc atacatattc atagttacga attgaagatg atggatggaa atatcgatct | 1500 |
| aggataggta tacatgttga tgcgggtttt actgatgcat atacagagat gcttttgtt | 1560 |
| cgcttggttg tgatgatgtg gtgtggttgg gcggtcgttc attcgttcta gatcggagta | 1620 |
| gaatactgtt tcaaactacc tggtgtattt attaattttg gaactgtatg tgtgtgtcat | 1680 |
| acatcttcat agttacgagt ttaagatgga tggaaatatc gatctaggat aggtatacat | 1740 |
| gttgatgtgg gttttactga tgcatataca tgatggcata tgcagcatct attcatatgc | 1800 |
| tctaaccttg agtaccctatc tattataata aacaagtatg ttttataatt attttgatct | 1860 |
| tgatatactt ggatgatggc atatgcagca gctatatgtg gatttttta gccctgcctt | 1920 |

```
catacgctat ttatttgctt ggtactgttt cttttgtcga tgctcaccct gttgtttggt    1980
gttacttctg cagggatccc cgatcatgca aaaactcatt aactcagtgc aaaactatgc    2040
ctggggcagc aaaacggcgt tgactgaact ttatggtatg gaaaatccgt ccagccagcc    2100
gatggccgag ctgtgatgg gcgcacatcc gaaaagcagt tcacgagtgc agaatgccgc    2160
cggagatatc gtttcactgc gtgatgtgat tgagagtgat aaatcgactc tgctcggaga    2220
ggccgttgcc aaacgctttg gcgaactgcc tttcctgttc aaagtattat gcgcagcaca    2280
gccactctcc attcaggttc atccaaacaa acacaattct gaaatcggtt ttgccaaaga    2340
aaatgccgca ggtatcccga tggatgccgc cgagcgtaac tataaagatc taaccacaa     2400 gccggagctg gttttgcgc tgacgccttt ccttgcgatg aacgcgtttc gtgaattttc     2460
cgagattgtc tccctactcc agccggtcgc aggtgcacat ccggcgattg ctcactttt      2520 acaacagcct gatgccgaac gtttaagcga actgttcgcc agcctgttga atatgcaggg    2580
tgaagaaaaa tcccgcgcgc tggcgatttt aaaatcggcc ctcgatagcc agcagggtga    2640
accgtggcaa acgattcgtt taatttctga attttacccg aagacagcg gtctgttctc      2700 cccgctattg ctgaatgtgg tgaaattgaa ccctggcgaa gcgatgttcc tgttcgctga    2760
aacaccgcac gcttacctgc aaggcgtggc gctggaagtg atggcaaact ccgataacgt    2820
gctgcgtgcg ggtctgacgc ctaaatacat tgatattccg gaactggttg ccaatgtgaa    2880
attcgaagcc aaaccggcta accagttgtt gacccagccg gtgaaacaag gtgcagaact    2940
ggacttcccg attccagtgg atgattttgc cttctcgctg catgacccta gtgataaaga    3000
aaccaccatt agccagcaga gtgccgccat tttgttctgc gtcgaaggcg atgcaacgtt    3060
gtggaaaggt tctcagcagt tacagcttaa accgggtgaa tcagcgttta ttgccgccaa    3120
cgaatcaccg gtgactgtca aaggccacgg ccgtttagcg cgtgtttaca acaagctgta    3180
agagcttact gaaaaaatta acatctcttg ctaagctggg agctcgatcc gtcgacctgc    3240
agatcgttca acatttggc aataaagttt cttaagattg aatcctgttg ccggtcttgc      3300
gatgattatc atataatttc tgttgaatta cgttaagcat gtaataatta acatgtaatg    3360
catgacgtta tttatgagat gggttttat gattagagtc ccgcaattat acatttaata    3420
cgcgatagaa acaaaatat agcgcgcaaa ctaggataaa ttatcgcgcg cggtgtcatc    3480
tatgttacta gatc                                                     3494
```

<210> SEQ ID NO 11
<211> LENGTH: 2903
<212> TYPE: DNA
<213> ORGANISM: Artificial Sequence
<220> FEATURE:
<223> OTHER INFORMATION: Sources: Cestrum Yellow Leaf Curl Virus,
    Escherichia coli, CaMV, Arabidopsis thaliana

<400> SEQUENCE: 11

```
tggcagacaa agtggcagac atactgtccc acaaatgaag atggaatctg taaaagaaaa     60
cgcgtgaaat aatgcgtctg acaaaggtta ggtcggctgc ctttaatcaa taccaaagtg    120
gtccctacca cgatggaaaa actgtgcagt cggtttggct ttttctgacg aacaaataag    180
attcgtggcc gacaggtggg ggtccaccat gtgaaggcat cttcagactc caataatgga    240
gcaatgacgt aagggcttac gaaataagta agggtagttt ggaaatgtc cactcacccg      300 tcagtctata aatacttagc ccctcccctca ttgttaaggg agcaaaatct cagagagata    360
gtcctagaga gagaaagaga gcaagtagcc tagaagtacg gtcgatcccc catcaaggta    420
```

```
cgccgctcgt cctccccccc cccccctctc taccttctct agatcggcgt tccggtccat      480
ggttagggcc cggtagttct acttctgttc atgtttgtgt tagatccgtg tttgtgttag      540
atccgtgctg ctagcgttcg tacacggatg cgacctgtac gtcagacacg ttctgattgc      600
taacttgcca gtgtttctct ttggggaatc ctgggatggc tctagccgtt ccgcagacgg      660
gatcgatttc atgattttt ttgtttcgtt gcataggggtt tggtttgccc ttttccttta      720
tttcaatata tgccgtgcac ttgtttgtcg ggtcatcttt tcatgctttt ttttgtcttg      780
gttgtgatga tgtggtctgg ttgggcggtc gttctagatc ggagtagaat tctgtttcaa      840
actacctggt ggatttatta attttggatc tgtatgtgtg tgccatacat attcatagtt      900
acgaattgaa gatgatggat ggaaatatcg atctaggata ggtatacatg ttgatgcggg      960
ttttactgat gcatatacag agatgctttt tgttcgcttg gttgtgatga tgtggtgtgg     1020
ttgggcggtc gttcattcgt tctagatcgg agtagaatac tgtttcaaac tacctggtgt     1080
atttattaat tttggaactg tatgtgtgtg tcatacatct tcatagttac gagtttaaga     1140
tggatggaaa tatcgatcta ggataggtat acatgttgat gtgggtttta ctgatgcata     1200
tacatgatgg catatgcagc atctattcat atgctctaac cttgagtacc tatctattat     1260
aataaacaag tatgttttat aattattttg atcttgatat acttggatga tggcatatgc     1320
agcagctata tgtggatttt tttagccctg ccttcatacg ctatttattt gcttggtact     1380
gtttcttttg tcgatgctca ccctgttgtt tggtgttact tctgcagctc gagtccgccg     1440
gctggagtag ggagacaatc tcggaaaatt cacgaaacgc gttcatcgca aggaaaggcg     1500
tcagcgcaaa aaccagctcc ggcttgtggt taggatcttt atagttacgc tcggcggcat     1560
ccatcgggat acctgcggca ttttctttgg caaaaccgat ttcagaattg tgtttgtttg     1620
gatgaacctg aatggagagt ggctgtgctg cgcataatac tttgaacagg aaaggcagtt     1680
cgccaaagcg tttggcaacg gcctctccga gcagagtcga tttatcactc tcaatcacat     1740
cacgcagtga acgatatctc ccggcggcat tctgcactcg tgaactgctt ttcggatgtg     1800
cgcccatcca cagctcggcc atcggctggc tggacggatt ttccatacca taaagttcag     1860
tcaacgccgt tttgctgccc caggcatagt tttgcactga gttaatgagt ttttgcatca     1920
attgaggtac caagctgcga atcttcgttt ttttaaggaa ttctcgatct ttatggtgta     1980
taggctctgg gttttctgtt ttttgtatct cttaggattt tgtaaattcc agatcttttct    2040 atggccactt agtagtatat ttcaaaaatt ctccaatcga gttcttcatt cgcatttttca    2100 gtcattttct cttcgacgtt gttttttaagc ctgggtatta ctcctattta gttgaactct    2160
gcagcaatct tagaaaatta gggttttgag gtttcgattt ctctaggtaa ccgatctatt    2220
gcattcatct gaatttctgc atatatgtct tagatttctg ataagcttac gatacgttag    2280
gtgtaattga agtttatttt tcaagagtgt tatttttttgt ttctgaattt tcaggtgag     2340 ctcatgcaaa aactcattaa ctcagtgcaa aactatgcct ggggcagcaa aacgggcgttg   2400 actgaacttt atggtatgga aaatccgtcc agccagccga tggccgagct gtggatgggc    2460
gcacatccga aaagcagttc acgagtgcag aatgccgccg gagatatcgt ttcactgcgt    2520
gatgtgattg agagtgataa atcgactctg ctcggagagg ccgttgccaa acgctttggc    2580
gaactgcctt tcctgttcaa agtattatgc gcagcacagc cactctccat tcaggttcat    2640
ccaaacaaac acaattctga aatcggtttt gccaaagaaa atgccgcagg tatcccgatg    2700
gatgccgccg agcgtaacta taaagatcct aaccacaagc cggagctggt ttttgcgctg    2760
```

| acgcctttcc ttgcgatgaa cgcgtttcgt gaattttccg agattgtctc cctactccag | 2820 |
| ccggttaatt aaacttagta tgtatttgta tttgtaaaat acttctatca ataaaatttc | 2880 |
| taattcctaa aaccaaaatc cag | 2903 |

<210> SEQ ID NO 12
<211> LENGTH: 1338
<212> TYPE: DNA
<213> ORGANISM: Artificial Sequence
<220> FEATURE:
<223> OTHER INFORMATION: Source: Zea mays

<400> SEQUENCE: 12

| atggccggtg ccgaggagat cgtgctgcag ccgatcaagg agatcagcgg caccgtgaag | 60 |
| ctgccgggca gcaagagcct gagcaaccgc atcctgctgc tggccgccct gagcgagggc | 120 |
| accaccgtgg tggacaacct gctgaacagc gaggacgtgc actacatgct gggcgccctg | 180 |
| aggaccctgg gcctgagcgt ggaggccgac aaggccgcca gaggccgt ggtggtgggc | 240 |
| tgcggcggca agttcccggt ggaggacgcc aaggaggagg tgcagctgtt cctgggcaac | 300 |
| gccggcatcg ccatgaggag cctgaccgcc gccgtgaccg ccgccggcgg caacgccacc | 360 |
| tacgtgctga cggcgtgcc gaggatgagg gagaggccga tcggcgacct ggtggtgggc | 420 |
| ctgaagcagc tgggcgccga cgtggactgc ttcctgggca ccgactgccc gccggtgagg | 480 |
| gtgaacggca tcggcggcct gccgggcggc aaggtgaagc tgagcggcag catcagcagc | 540 |
| cagtacctga gcgccctgct gatggccgcc ccgctggccc tgggcgacgt ggagatcgag | 600 |
| atcatcgaca agctgatcag catcccgtac gtggagatga ccctgaggct gatggagagg | 660 |
| ttcggcgtga aggccgagca cagcgacagc tgggacaggt tctacatcaa gggcggccag | 720 |
| aagtacaaga gcccgaagaa cgcctacgtg gagggcgacg ccagcagcgc cagctacttc | 780 |
| ctggccggcg ccgccatcac cggcggcacc gtgaccgtgg agggctgcgg caccaccagc | 840 |
| ctgcagggcg acgtgaagtt cgccgaggtg ctggagatga tgggcgccaa ggtgacctgg | 900 |
| accgagacca gcgtgaccgt gaccggcccg ccgagggagc cgttcggcag gaagcacctg | 960 |
| aaggccatcg acgtgaacat gaacaagatg ccggacgtgg ccatgaccct ggccgtggtg | 1020 |
| gccctgttcg ccgacggccc gaccgccatc agggacgtgg ccagctggag ggtgaaggag | 1080 |
| accgagagga tggtggccat caggaccgag ctgaccaagc tgggcgccag cgtggaggag | 1140 |
| ggcccggact actgcatcat caccccgccg gagaagctga acgtgaccgc catcgacacc | 1200 |
| tacgacgacc acaggatggc gatggccttc agcctggccg cctgcgccga ggtgccggtg | 1260 |
| accatcagag acccgggctg caccaggaag accttcccgg actacttcga cgtgctgagc | 1320 |
| accttcgtga agaactaa | 1338 |

<210> SEQ ID NO 13
<211> LENGTH: 1176
<212> TYPE: DNA
<213> ORGANISM: Artificial Sequence
<220> FEATURE:
<223> OTHER INFORMATION: Source: Escherichia coli

<400> SEQUENCE: 13

| atgcaaaaac tcattaactc agtgcaaaac tatgcctggg gcagcaaaac ggcgttgact | 60 |
| gaactttatg gtatggaaaa tccgtccagc cagccgatgg ccgagctgtg gatgggcgca | 120 |
| catccgaaaa gcagttcacg agtgcagaat gccgccggaa atatcgtttc actgcgtgat | 180 |
| gtgattgaga gtgataaatc gactctgctc ggagaggccg ttgccaaacg ctttggcgaa | 240 |

```
ctgcctttcc tgttcaaagt attatgcgca gcacagccac tctccattca ggttcatcca         300
aacaaacaca attctgaaat cggttttgcc aagaaaatg  ccgcaggtat cccgatggat         360
gccgccgagc gtaactataa agatcctaac cacaagccgg agctggtttt tgcgctgacg         420
cctttccttg cgatgaacgc gtttcgtgaa ttttccgaga ttgtctccct actccagccg         480
gtcgcaggtg cacatccggc gattgctcac ttttttacaac agcctgatgc cgaacgttta       540
agcgaactgt tcgccagcct gttgaatatg cagggtgaag aaaaatcccg cgcgctggcg         600 atttttaaaat cggccctcga tagccagcag ggtgaaccgt ggcaaacgat tcgtttaatt       660
tctgaatttt acccggaaga cagcggtctg ttctccccgc tattgctgaa tgtggtgaaa         720
ttgaaccctg gcgaagcgat gttcctgttc gctgaaacac cgcacgctta cctgcaaggc         780
gtggcgctgg aagtgatggc aaactccgat aacgtgctgc gtgcgggtct gacgcctaaa         840
tacattgata ttccggaact ggttgccaat gtgaaattcg aagccaaacc ggctaaccag         900
ttgttgaccc agccggtgaa acaaggtgca gaactggact tcccgattcc agtggatgat         960
tttgccttct cgctgcatga ccttagtgat aaagaaacca ccattagcca gcagagtgcc        1020
gccattttgt tctgcgtcga aggcgatgca acgttgtgga aggttctca  gcagttacag        1080 cttaaaccgg gtgaatcagc gtttattgcc gccaacgaat caccggtgac tgtcaaaggc        1140
cacggccgtt tagcgcgtgt ttacaacaag ctgtaa                                  1176

<210> SEQ ID NO 14
<211> LENGTH: 5802
<212> TYPE: DNA
<213> ORGANISM: Artificial Sequence
<220> FEATURE:
<223> OTHER INFORMATION: source:  Oryza sativa

<400> SEQUENCE: 14
acaccaccat aaagctagct tgcaaagggg atagagtagt agagagagag agagaggaga          60
ggaggaggaa gaagtagggg aggggggaagg tggagctgaa gcggatcgag aacaagatca       120
gccggcaggt gacgttcgcc aagcgcagga acggcctgct caagaaggcc tacgagcact        180
ccctcctctg cgacgccgag gtcgccctca tcatcttctc cggccgcggc cgcctcttcg        240
agttctccag ctcatctagg tacgtatagc accaaaccaa cgccgccgcc gccgccggcg        300
tgcttgttcc ggcgcagcag cgcatcatca tcgatcgatc taagtctaat aagataatca       360 attaaccta  actaaataaa atgataagaa cagtatatat ggttatgatc agtgaaacac        420
tcgtcgatct gagggaaaat ccggtcgaga tcgagggagt ggggagacaa attgaactgc        480
aggctagcta atttaatcgt gtcgatcgat ttctagcttt tgttgatctt tatatatacg       540
aacgcatgca ctttccccct tgtttttttt tcccttcgat ctgcttggag cacatatgct       600
atagatcttg gggcatatgt atctgtcagc tttcgagagc ggctatgtcc atcgatccct       660
cttttttttc tctttctttt tgtagtatca gctgccatgc atatatcaga tttcgttttc       720
gcgtgctttt agtgcttcac ttatctgttc gccatatctg atttcttctc atcctttgcc       780
gacgtcgtct gagcagtctg acctccaaga tctggcgaaa taaacctcaa tcgttgctat       840
ttcttgcctt gaatctgcat aaacatgaca atagatcctt ctattttttt tcttcaagac       900
aagatcttgc tgtttcttcc cttgctattt tcattcaaa  gattcttct  ttttttctaa       960 aagaactata tatatatgaa tcgagtttca tcttcatcga tctgtctctc tccttttgtt      1020
ttctgtaaac acacacacga gcgtacgtat atatactctc atctctactt ttatcaaaaa      1080
```

-continued

```
gaaacacaca tgttctagct tcagatccca aaataatcaa acaggaaaat atatataata    1140
tgcaattagt tcagatcccg aggtagattt cttgattatt tccattttcc aaagtgaggc    1200
gcgcgacaac tcgacgcggt tcctctttgc acacacacac agtataactg tacgcaaggg    1260
gtaagaacaa aggagcaatc ccttctgggt tgctgcttgc ttctcccatt tttagctatt    1320
tcagaatttc actttctgag actcatctct ctctctctac cagctgcatt atttcacttc    1380 cctttttttcc catttctgcc tattacacgg atggcctctt tgtggactcg tccaaattga    1440
ggcacggtag ctggtgtcaa aatgaacctg caggcccagc ccggttatgt atatgtatag    1500
ctatatagct tttcttgcaa gaggtatata cactttgtag ttttagccag tggtccagct    1560
agccaaggat ggatatatta tacacacgta tatatagtac atgtatgtac gagtgttaat    1620
taaactcgtt tagttaattt ccaaagtcct tttttattac tacagctagc ctgatctgtg    1680
ttttagtgtg ttactgttcc attagttact gttctattga agagagcgcg tacacgttgt    1740
tgttttattt ctcttttttcc gatccggtgt tcctttttttt tttctttttgg tcatcttcct    1800 cgagtcccga gcagtagaaa tactactact gccctgcaaa gcacacacat caagtgatgt    1860
gtttttcttc agagcttcag acgtgtcata tcaagcaggt cagcacgcat tacatgcaat    1920
ataatactcc tatatggaca cgcagaactc actttgatca tgtgtgacca agctggatga    1980
gccgttaatt tgttgttggg acagggtatt gaatcattaa ttgcggtttt tcctctttttt    2040 cctgtcttgt tctactcaga gaattgaacg gtgaactgta taggcagagc tagtcctgca    2100
tgcatcggtt ttctgaaatt attaactata cacacacatg cacaattgct aaatctggta    2160
tacatgtctt gctgactcac atattcgttc ctcctaatta aagcactcat ttatttattt    2220
tacacggttt tcaatgatat actttaaata ttaatttgtt tgatgttata tttctatgaa    2280
tatgaaatta gcatcatatg aaaatacttt aaaacaaata tagtgatata acatgcataa    2340
tacttagcat atacttgtat gattagcatg gtcattaatc aaaagttgcc gagcttgaat    2400
tttctaaagg acagggtgcc ttgtaatttg ggacaaagaa ccattggaaa acgaacacaa    2460
agaaactttc attacattaa ttatctgaaa aagaaagaaa ctttcattaa cctcgtacag    2520
taaatagaaa agaggaacta tgcatgtata acgaaatagc taggatcaca gcaattaatt    2580
agttgttctc tggctttact tttcttttgg agtaacttta attttctttt ggaggatgaa    2640
gtagttaatt atacaggttt ccaattcttg tttggtagat cctttttttat gttcctggaa    2700 gagctactat attttttgtac ttgagatgga gctgaggtac cgttatctag ctatgtcgca    2760
tctcaaggag ttacgaatta acatatatca ccaatatcac aaaaatgctc atacaaaaa    2820 gatcataaaa attcttgaat ttgcttgctg tgtttttttta ctatatatgc ttggaattaa    2880
aaaaatgact gaattaatcg tttgcaatct ttaacggtgc gtgcagtacc aaattggaaa    2940
ggtatccact tgttcaaact taaaaatatt ttttttactg atattactct ctaaaaaggt    3000
gcatgggaaa tgctattgga actactagtt ttcgggacat tataagaaaa tgtatgcata    3060
tatatatata tatatggact tatgatatgg gccagatacc tatatatata gaagatatat    3120
gtgtgctact acctccattc aacaatacaa gcatttgagc cagttctggt caaggatata    3180
aacatcctgc actattagct tgtacttgtc aaattaatga tctctaattc aaactttctt    3240
gctactttac ccccaatcac ccttcccaac catcttaatc tttgctaaac attctagaaa    3300
tgcttattgt tggatggagg aagtagctat taactactcc tatagttttt ttaactacct    3360
catattaatt ttgtaatcct aataaatgca ctatatatgc ccacttttac cgtgtttcca    3420
aactggcatc aagctaaaat gaatgttaat ttagtttccc cataatttta tgagaatcgc    3480
```

```
aaaattgtac ctattttaaa caaatcaaag tcactgaaca aatgaacgga ggttaattat    3540
tatattcacc tgatataggc agactaggtt gggctaagag ggacattaat ttgggcatct    3600
aggttttgaa atgggagata tggagagtga accaaaaaaa aactgttagt gaattagtac    3660
atgatatata ctagtattat tagtgggaac ctagagaaat gcaaagaatg ttgcgcaaat    3720
catcattttg tgtaaattaa aatgggatat acactatggg gaactatagc tgagtgtcaa    3780
tccccacctt ttgtttgtaa ttaaacatgt gtttatgcta caaattactc cctccgtact    3840
cataaaggaa gtcgtttagg acaatgttta agtcaaacct tgggaatata aattatgaat    3900
aactctcaag ttgttgagtt tgaaaatgta aaaaatatat gaatagattt gtcttgaaaa    3960
atactttcat aaaagtatac atatatcact tttcaataaa tattttatag aaacaagaag    4020
tcaaaattgt gttttggaga ccgtgtcact gtccaaaacg acttctttac gagtacggag    4080
ggagtatgtt ctacatattg gctaatattg ttgaaccctt cggatcaatc ttagacacag    4140
tagccatttt acccactgat gcagcaaccc aattaggtat ctactaatta gcatcatagt    4200
gcaaatttgt acttttcaag tggaaaatag aaattatttg tcctccttta ctttaatttc    4260
ttgataatat gatatatgta acataatttc tctttgctcc caagcatata aaaaacttca    4320
atttgatatg tccaaaaaat gtcatatata tagcatgtaa tcctctgtgg caaacacgtt    4380
tttttggctc aaattaagaa gaggaaaaaa tggtatatat gtataaacct aacaaaaatg    4440
ccccaacaag aatagcttta ttttgtgaac aaggtcatat agaccaggga acaaaaaccc    4500
tgtactgtgc ttctattttg ctatgcattt tggataagtg attctacaga aatatgacta    4560
tataggagat attctcaaat ctgatctttt ctattaatta gcccatacga tatgaagaca    4620
tatcttcctc tgttctgatt ctatttgttg tgctaagata gtctacagga tttgctaggt    4680
tgccacctgc cgtcaacaaa attcagctca tcagattttg ttatagttgc tagcacagtt    4740
atattatacg tatatctctt ttgagaatat attattacag tccattgatt tttcttgtag    4800
agtggaaaat attattgtgt tttctaaccg taggagttca tgtggtgtta tttattttgg    4860
ataatgtggt gtattttttat gagaaatcag gatcgcgtca acatgaaagt ttcatctaat    4920
acattattaa gtgcatcgta gcaacaattc atatattaac tcaaaggtag ctttgaaatt    4980
aagatgcatg tcattaatgc ataatagaga aatcaggtta ccaaattata ttaagcccat    5040
atattaactc aaaggtcata gctttgacaa atgctcctta cagatttctc cttgaaccaa    5100
tttgtaaaat atcctctcct ttttttttgc gcgaacgcta aatatccttt gtttaacaac    5160
ctcgtcaatt tgtccatttc atatgtgtga acatccttgt acattctttt ttgtgccgtt    5220
tgaaataaaa ctttgaataa atatgcacaa cttaaatgct taaatgtcaa ttggatttgg    5280
atgaaacaaa accaaagttt tagaatttac gatctatcat tatgaattta tgtatgatat    5340
atcacactct ttctgaataa acttcagaat aatataaatt gcttaattat ggtatacatg    5400
agcatatata gcttgcgcaa atcaaaactg tacagtaggt gtgtgttcaa ttcagaatag    5460 tattctatt cgaatttaaa ttaataatac cttctgtagt aatttctata ttagaaaatt    5520
tatacataca aggagcactg ttaattagct agctagcttt atgggttcca ctaatcaatt    5580
tatatataat aatgtgctaa actatacagc gtccatgcat ttttattctt catgcctaat    5640
taatttgatt caccattaat taattctacg tacaatgttc gaatgtgtga ctatatatgc    5700
tgcatctgca gttctgcacc tcattcagta ctaaattcaa gttcaggttc attaattaat    5760
tcacttattc cttcattttt cacttccagc taatacaaaa cc                      5802
```

<210> SEQ ID NO 15
<211> LENGTH: 1710
<212> TYPE: DNA
<213> ORGANISM: Artificial Sequence
<220> FEATURE:
<223> OTHER INFORMATION: source: Zea mays

<400> SEQUENCE: 15

| | |
|---|---|
| atggcttcga tctcctcctc agtcgcgacc gttagcagga ccgcccctgc tcaggccaac | 60 |
| atggtggctc cgttcaccgg ccttaagtcc aacgccgcct tccccaccac caagaaggct | 120 |
| aacgacttct ccaccttcc cagcaacggt ggaagagttc aatgtatgca ggtgtggccg | 180 |
| gcctacggca acaagaagtt cgagacgctg tcgtacctgc cgccgctgtc tatggcgccc | 240 |
| accgtgatga tggcctcgtc ggccaccgcc gtcgctccgt tccagggct caagtccacc | 300 |
| gccagcctcc ccgtcgcccg ccgctcctcc agaagcctcg gcaacgtcag caacggcgga | 360 |
| agaatccggt gctgagccgg tgccgaggag atcgtgctgc agccgatcaa ggagatcagc | 420 |
| ggcaccgtga agctgccggg cagcaagagc ctgagcaacc gcatcctgct gctggccgcc | 480 |
| ctgagcgagg gcaccaccgt ggtggacaac ctgctgaaca gcgaggacgt gcactacatg | 540 |
| ctgggcgccc tgaggaccct gggcctgagc gtggaggccg acaaggccgc caagagggcc | 600 |
| gtggtggtgg gctgcggcgg caagttcccg gtggaggacg ccaaggagga ggtgcagctg | 660 |
| ttcctgggca acgccggcat cgccatgagg agcctgaccg ccgccgtgac cgccgccggc | 720 |
| ggcaacgcca cctacgtgct ggacggcgtg ccgaggatga gggagaggcc gatcggcgac | 780 |
| ctggtggtgg gcctgaagca gctgggcgcc gacgtggact gcttcctggg caccgactgc | 840 |
| ccgccggtga gggtgaacgg catcggcggc ctgccgggcg gcaaggtgaa gctgagcggc | 900 |
| agcatcagca gccagtacct gagcgccctg ctgatggccg ccccgctggc cctgggcgac | 960 |
| gtggagatcg agatcatcga caagctgatc agcatcccgt acgtggagat gacgctgagg | 1020 |
| ctgatggaga ggttcggcgt gaaggccgag cacagcgaca gctgggacag gttctacatc | 1080 |
| aagggcggcc agaagtacaa gagcccgaag aacgcctacg tggagggcga cgccagcagc | 1140 |
| gccagctact cctggccgg cgccgccatc accggcggca ccgtgaccgt ggagggctgc | 1200 |
| ggcaccacca gcctgcaggg cgacgtgaag ttcgccgagg tgctggagat gatgggcgcc | 1260 |
| aaggtgacct ggaccgagac cagcgtgacc gtgaccggcc cgccgaggga gcgttcggc | 1320 |
| aggaagcacc tgaaggccat cgacgtgaac atgaacaaga tgccggacgt ggccatgacc | 1380 |
| ctggccgtgg tggccctgtt cgccgacggc ccgaccgcca tcaggacgt ggccagctgg | 1440 |
| agggtgaagg agaccgagag gatggtggcc atcaggaccg agctgaccaa gctgggcgcc | 1500 |
| agcgtggagg agggccccgga ctactgcatc atcaccccgc cggagaagct gaacgtgacc | 1560 |
| gccatcgaca cctacgacga ccacaggatg gcgatggcct tcagcctggc cgcctgcgcc | 1620 |
| gaggtgccgg tgaccatcag agacccgggc tgcaccagga gaccttccc ggactacttc | 1680 |
| gacgtgctga gcaccttcgt gaagaactaa | 1710 |

<210> SEQ ID NO 16
<211> LENGTH: 1387
<212> TYPE: DNA
<213> ORGANISM: Artificial Sequence
<220> FEATURE:
<223> OTHER INFORMATION: Sources: Escherichia coli, Arabidopsis
     thaliana

<400> SEQUENCE: 16

| | |
|---|---|
| ccggctggag tagggagaca atctcggaaa attcacgaaa cgcgttcatc gcaaggaaag | 60 |
| gcgtcagcgc aaaaaccagc tccggcttgt ggttaggatc tttatagtta cgctcggcgg | 120 |
| catccatcgg gatacctgcg gcattttctt tggcaaaacc gatttcagaa ttgtgtttgt | 180 |
| ttggatgaac ctgaatggag agtggctgtg ctgcgcataa tactttgaac aggaaaggca | 240 |
| gttcgccaaa gcgtttggca acggcctctc cgagcagagt cgatttatca ctctcaatca | 300 |
| catcacgcag tgaaacgata tctccggcgg cattctgcac tcgtgaactg cttttcggat | 360 |
| gtgcgcccat ccacagctcg gccatcggct ggctggacgg attttccata ccataaagtt | 420 |
| cagtcaacgc cgttttgctg ccccaggcat agttttgcac tgagttaatg agttttttgca | 480 |
| tcaattgagg taccaagctg cgaatcttcg ttttttttaag gaattctcga tctttatggt | 540 |
| gtataggctc tgggttttct gttttttgta tctcttagga ttttgtaaat tccagatctt | 600 |
| tctatggcca cttagtagta tatttcaaaa attctccaat cgagttcttc attcgcattt | 660 |
| tcagtcattt tctcttcgac gttgttttta agcctgggta ttactcctat ttagttgaac | 720 |
| tctgcagcaa tcttagaaaa ttagggtttt gaggtttcga tttctctagg taaccgatct | 780 |
| attgcattca tctgaatttc tgcatatatg tcttagattt ctgataagct tacgatacgt | 840 |
| taggtgtaat tgaagtttat ttttcaagag tgttattttt tgtttctgaa ttttttcaggt | 900 |
| gagctcatgc aaaaactcat taactcagtg caaaactatg cctggggcag caaaacggcg | 960 |
| ttgactgaac tttatggtat ggaaaatccg tccagccagc cgatggccga gctgtggatt | 1020 |
| ggcgcacatc cgaaaagcag ttcacgagtg cagaatgccg ccggagatat cgtttcactg | 1080 |
| cgtgatgtga ttgagagtga taaatcgact ctgctcggag aggccgttgc caaacgcttt | 1140 |
| ggcgaactgc ctttcctgtt caaagtatta tgcgcagcac agccactctc cattcaggtt | 1200 |
| catccaaaca aacacaattc tgaaatcggt tttgccaaag aaaatgccgc aggtatcccg | 1260 |
| atggatgccg ccgagcgtaa ctataaagat cctaaccaca agccggagct ggttttttgcg | 1320 |
| ctgacgcctt tccttgcgat gaacgcgttt cgtgaatttt ccgagattgt ctccctactc | 1380 |
| cagccgg | 1387 |

<210> SEQ ID NO 17
<211> LENGTH: 10865
<212> TYPE: DNA
<213> ORGANISM: Artificial Sequence
<220> FEATURE:
<223> OTHER INFORMATION: Sources: FMV, CaMV, Oryza sativa, Escherichia coli

<400> SEQUENCE: 17

| | |
|---|---|
| agctgcttgt ggggaccaga caaaaaagga atggtgcaga attgttaggc gcacctacca | 60 |
| aaagcatctt tgcctttatt gcaaagataa agcagattcc tctagtacaa gtggggaaca | 120 |
| aaataacgtg gaaagagct gtcctgacag cccactcact aatgcgtatg acgaacgcag | 180 |
| tgacgaccac aaaactcgag acttttcaac aaagggtaat atccggaaac ctcctcggat | 240 |
| tccattgccc agctatctgt cactttattg tgaagatagt ggaaaggaa ggtggctcct | 300 |
| acaaatgcca tcattgcgat aaaggaaagg ctatcgttga agatgcctct gccgacagtg | 360 |
| gtcccaaaga tggacccca cccacgagga gcatcgtgga aaagaagac gttccaacca | 420 |
| cgtcttcaaa gcaagtggat tgatgtgata tctccactga cgtaagggat gacgaacaat | 480 |
| cccactatcc ttcggtaccg gacccacaaa tttgttgtac cacctaccta ggggtgacaa | 540 |
| cactgcacat ttggctattt agggccacgc atatatgcat gaaaaattga cacacgacgt | 600 |

| | | | | | |
|---|---|---|---|---|---|
| tacttgagaa | cctattcatg | caggtctatg | agaaaacccc | accaaaaaaa | acagatgtgc | 660 |
| aaaataatgc | tggatttca | tatgctataa | attaagtact | actttaatca | aacaccacat | 720 |
| tgacacacaa | tgacacaaat | taaatactct | tacgaattca | agtcatatat | actctaatac | 780 |
| gcacgtgcag | cttgttactc | aaataaagaa | acagggcaat | acggatcagt | atatccaacc | 840 |
| aggctgcatg | taggccaaga | acctgacaat | tcgttttcct | tggagaaagc | aaagaacgtt | 900 |
| tggaacgtgt | gatgtacatg | cagatcgagg | aaaatagcta | atcctgctct | ttccctttcc | 960 |
| agcacaaaaa | aagattcctt | cgtagttcgc | actgcattta | tactcaaacc | tgcaaggctc | 1020 |
| ccaaacagtt | tgaaccaagg | cgagggaaaa | aaaaaacatc | tccatagcca | agagaaaaca | 1080 |
| tactgtacat | gtcaagagat | tccctcttca | tattcttaca | atcctattta | ctcaaattaa | 1140 |
| atcttcatat | ttcacttcgt | aaattccaac | ggctaatttg | gtcagcacaa | attcagcatc | 1200 |
| tcaatcaaca | caatttcaat | gcatgaaggc | gatcaagctc | accactctcc | tgccatacaa | 1260 |
| gatggaccgc | caccgcttgg | aatttccgca | gtgacggcaa | cacgaggaag | aggcaacact | 1320 |
| agcggatgta | tgaaggagtc | tgccaagctc | ggctatttcc | ggcgagcttg | agagtataat | 1380 |
| cgagatagag | gccggtggaa | agacgaaagg | cggcgtactc | ttgggcttag | tgtggaggca | 1440 |
| acggtggcgg | cctcgcggag | aggtgacgac | accttggctt | ggcatggcag | agttccactt | 1500 |
| ctcaacaggg | atgcatgaca | ctcctaggta | agaaggcggc | ggtgctggtg | ggtgtgggtg | 1560 |
| gaggcacatg | gacttctctc | aacaataaag | ttgctctcgc | tgtcaaacta | ttccctctgc | 1620 |
| caagtttgat | cactcaattt | cttgatttgg | ctagtcggat | aagatagtca | ccgacatagc | 1680 |
| caaccagatg | ggataacccc | ttttttttta | gcatggagag | tgggaccaaa | tgtccaagct | 1740 |
| atctcccata | ctccctatgt | ccaaaaaaaa | ataatatttt | ttaaattcat | atctaacata | 1800 |
| cgaagataat | actcttcgtt | gaaaaaaaaa | caacttcaga | atctagacac | aactttattt | 1860 |
| tttataagac | ggaaagactg | tactcctata | ctcctacatt | tcaccatttt | tttccccgcg | 1920 |
| taaaaacaaa | cccccgaatt | gaccgtccac | tgtagcatca | ctccatcaga | cttgaagcga | 1980 |
| gtgagagaca | gagcgctgcg | ttaaaagaa | aagaggaaag | aaccggacgc | agagccctac | 2040 |
| tgtcaaactg | acaaggcagg | aagaagaaag | ggaagccccc | cctaccaagc | cctagcctcc | 2100 |
| ttgtccgttt | gctcccccc | agcgccaccc | cccgtcgaca | cgcgtcgccc | accctctgcc | 2160 |
| attccctctt | ccgccctccc | agccactact | acgcttttac | tccctgccgc | gcgcgcgaga | 2220 |
| tcttcacctt | caccgtatcc | gctcgcgttt | tgcacgcagt | tgatttgcgc | tttgttttg | 2280 |
| catcctacga | aactaaccgc | acaccaatca | cctcctccac | caccgcacag | agctatagct | 2340 |
| agcgaggagc | gtgctacagt | gcgctgcgca | ggagagagaa | tcgatcgatg | gaagaacgcg | 2400 |
| acaggagcaa | gctagccagc | ctagctgtag | cgacgtgaca | gcagtttgat | ctttctttt | 2460 |
| ttcttatgat | ggctaagctt | atacgtaagc | cgatcgatcg | atggcgagat | agatcagaga | 2520 |
| ttaatataca | ggggtaatta | atgtactaat | tacaattaag | tgtgtggacg | agcgagccgt | 2580 |
| gtggagttac | agctagctag | cgcttatgct | actcctactt | aaggcgagac | cccaaactcc | 2640 |
| aagcatacga | tcaggtagcc | aaaccacacc | accataaagc | tagcttgcaa | agggatagaa | 2700 |
| gtagtagaga | gagagagaga | ggagaggagg | aggaagaagt | aggggagggg | gaaggtggag | 2760 |
| ctgaagcgga | tcgagaacaa | gatcagccgg | caggtgacgt | tcgccaagcg | caggaacggc | 2820 |
| ctgctcaaga | aggcctacga | gcactccctc | ctctgcgacg | ccgaggtcgc | cctcatcatc | 2880 |
| ttctccggcc | gcggccgcct | cttcgagttc | tccagctcat | ctaggtacgt | atagcaccaa | 2940 |
| accaacgccg | ccgccgccgc | cggcgtgctt | gttccggcgc | agcagcgcat | catcatcgat | 3000 |

```
cgatctaagt ctaataagat aatcaattaa ccctaactaa ataaaatgat aagaacagta    3060
tatatggtta tgatcagtga acactcgtc gatctgaggg aaaatccggt cgagatcgag     3120
ggagtgggga gacaaattga actgcaggct agctaattta atcgtgtcga tcgatttcta    3180
gcttttgttg atctttatat atacgaacgc atgcactttc cctttgttt tttttttccct   3240 tcgatctgct tggagcacat atgctataga tcttggggca tatgtatctg tcagctttcg   3300
agagcggcta tgtccatcga tccctctttt ttttctcttt cttttgtag tatcagctgc    3360 catgcatata tcagatttcg ttttcgcgtg cttttagtgc ttcacttatc tgttcgccat   3420
atctgatttc ttctcatcct tgccgacgt cgtctgagca gtctgacctc caagatctgg    3480
cgaaataaac ctcaatcgtt gctatttctt gccttgaatc tgcataaaca tgacaataga   3540
tccttctatt tttttcttc aagacaagat cttgctgttt cttcccttgc tatttttcat    3600
tcaaagattc ttctttttt tctaaaagaa ctatatatat atgaatcgag tttcatcttc    3660
atcgatctgt ctctctcctt tgttttctg taaacacaca cacgagcgta cgtatatata    3720
ctctcatctc tactttatc aaaaagaaac acacatgttc tagcttcaga tcccaaaata    3780
atcaaacagg aaaatatata taatatgcaa ttagttcaga tcccgaggta gatttcttga   3840
ttatttccat tttccaaagt gaggcgcgcg acaactcgac gcggttcctc tttgcacaca   3900
cacacagtat aactgtacgc aagggtaag aacaaaggag caatcccttc tgggttgctg    3960
cttgcttctc ccatttttag ctatttcaga atttcacttt ctgagactca tctctctctc   4020
tctaccagct gcattatttc acttcccttt tttcccattt ctgcctatta cacggatggc   4080
ctctttgtgg actcgtccaa attgaggcac ggtagctggt gtcaaaatga acctgcaggc   4140
ccagcccggt tatgtatatg tatagctata tagcttttct tgcaagaggt atatacactt   4200
tgtagtttta gccagtggtc cagctagcca aggatggata tattatacac acgtatatat   4260
agtacatgta tgtacgagtg ttaattaaac tcgtttagtt aatttccaaa gtccttttt    4320 attactacag ctagcctgat ctgtgtttta gtgtgttact gttccattag ttactgttct   4380
attgaagaga gcgcgtacac gttgttgttt tatttctctt tttccgatcc ggtgttcctt   4440 tttttttct tttggtcatc ttcctcgagt cccgagcagt agaaatacta ctactgccct    4500
gcaaagcaca cacatcaagt gatgtgtttt tcttcagagc ttcagacgtg tcatatcaag   4560
caggtcagca cgcattacat gcaatataat actcctatat ggacacgcag aactcacttt   4620
gatcatgtgt gaccaagctg gatgagccgt taatttgttg ttgggacagg gtattgaatc   4680
attaattgcg gttttttcctc ttttcctgt cttgttctac tcagagaatt gaacggtgaa   4740
ctgtataggc agagctagtc ctgcatgcat cggttttctg aaattattaa ctatacacac   4800
acatgcacaa ttgctaaatc tggtatacat gtcttgctga ctcacatatt cgttcctcct   4860
aattaaagca ctcatttatt tattttacac ggttttcaat gatatacttt aaatattaat   4920
ttgtttgatg ttatatttct atgaatatga aattagcatc atatgaaaat actttaaaac   4980
aaatatagtg atataacatg cataatactt agcatatact tgtatgatta gcatggtcat   5040
taatcaaaag ttgccgagct tgaattttct aaaggacagg gtgccttgta atttgggaca   5100
aagaaccatt ggaaaacgaa cacaaagaaa ctttcattac attaattatc tgaaaagaa    5160 agaaactttc attaacctcg tacagtaaat agaaagagg aactatgcat gtataacgaa    5220
atagctagga tcacagcaat taattagttg ttctctggct ttacttttct tttggagtaa   5280
ctttaatttt tctttggagg atgaagtagt taattataca ggtttccaat tcttgtttgg   5340
```

```
tagatccttt tttatgttcc tggaagagct actatatttt tgtacttgag atggagctga    5400
ggtaccgtta tctagctatg tcgcatctca aggagttacg aattaacata tatcaccaat    5460
atcacaaaaa tgctccatac aaaaagatca taaaaattct tgaatttgct tgctgtgttt    5520
ttttactata tatgcttgga attaaaaaaa tgactgaatt aatcgtttgc aatcttttaac   5580 ggtgcgtgca gtaccaaatt ggaaaggtat ccacttgttc aaacttaaaa atatttttt    5640 tactgatatt actctctaaa aaggtgcatg ggaaatgcta ttggaactac tagttttcgg    5700
gacattataa gaaaatgtat gcatatatat atatatatat ggacttatga tatgggccag    5760 ataccctatat atatagaaga tatatgtgtg ctactacctc cattcaacaa tacaagcatt    5820
tgagccagtt ctggtcaagg atataaacat cctgcactat tagcttgtac ttgtcaaatt    5880
aatgatctct aattcaaact ttcttgctac tttacccccca atcaccctt ccaaccatct    5940 taatctttgc taaacattct agaaatgctt attgttggat ggaggaagta gctattaact    6000
actcctatag ttttttaac tacctcatat taattttgta atcctaataa atgcactata    6060
tatgcccact tttaccgtgt ttccaaactg gcatcaagct aaaatgaatg ttaatttagt    6120
ttccccataa ttttatgaga atcgcaaaat tgtacctatt ttaaacaaat caaagtcact    6180
gaacaaatga acggaggtta attattatat tcacctgata taggcagact aggttgggct    6240
aagagggaca ttaatttggg catctaggtt ttgaaatggg agatatggag agtgaaccaa    6300
aaaaaaactg ttagtgaatt agtacatgat atatactagt attattagtg ggaacctaga    6360
gaaatgcaaa gaatgttgcg caaatcatca ttttgtgtaa attaaaatgg gatatacact    6420
atggggaact atagctgagt gtcaatcccc acctttttgtt tgtaattaaa catgtgttta    6480
tgctacaaat tactccctcc gtactcataa aggaagtcgt ttaggacaat gtttaagtca    6540
aaccttggga atataaatta tgaataactc tcaagttgtt gagtttgaaa atgtaaaaaa    6600
tatatgaata gatttgtctt gaaaaatact ttcataaaag tatacatata tcacttttca    6660
ataaatattt tatagaaaca agaagtcaaa attgtgtttt ggagaccgtg tcactgtcca    6720
aaacgacttc tttacgagta cggagggagt atgttctaca tattggctaa tattgttgaa    6780
cccttcggat caatcttaga cacagtagcc attttaccca ctgatgcagc aacccaatta    6840
ggtatctact aattagcatc atagtgcaaa tttgtacttt tcaagtggaa aatagaaatt    6900
atttgtcctc ctttacttta atttcttgat aaatatgatat atgtaacata atttctcttt    6960
gctcccaagc atataaaaaa cttcaatttg atatgtccaa aaaatgtcat atatatagca    7020
tgtaatcctc tgtggcaaac acgtttttt ggctcaaatt aagaagagga aaaaatggta    7080
tatatgtata aacctaacaa aaatgcccca acaagaatag ctttatttg tgaacaaggt    7140 catatagacc agggaacaaa aaccctgtac tgtgcttcta ttttgctatg cattttggat    7200
aagtgattct acagaaatat gactatatag gagatattct caaatctgat cttttctatt    7260
aattagccca tacgatatga agacatatct tcctctgttc tgattctatt tgttgtgcta    7320
agatagtcta caggatttgc taggttgcca cctgccgtca acaaaattca gctcatcaga    7380
ttttgttata gttgctagca cagttatatt atacgtatat ctctttgag aatatattat    7440 tacagtccat tgatttttct tgtagagtgg aaaatattat tgtgttttct aaccgtagga    7500
gttcatgtgg tgttatttat tttggataat gtggtgtatt tttatgagaa atcaggatcg    7560
cgtcaacatg aaagtttcat ctaatacatt attaagtgca tcgtagcaac aattcatata    7620
ttaactcaaa ggtagctttg aaattaagat gcatgtcatt aatgcataat agagaaatca    7680
ggttaccaaa ttatattaag cccatatatt aactcaaagg tcatagcttt gacaaatgct    7740
```

```
ccttacagat ttctccttga accaatttgt aaaatatcct ctcctttttt tttgcgcgaa    7800
cgctaaatat cctttgttta acaacctcgt caatttgtcc atttcatatg tgtgaacatc    7860
cttgtacatt cttttttgtg ccgtttgaaa taaaactttg aataaatatg cacaacttaa    7920
atgcttaaat gtcaattgga tttggatgaa acaaaaccaa agttttagaa tttacgatct    7980
atcattatga atttatgtat gatatatcac actctttctg aataaacttc agaataatat    8040
aaattgctta attatggtat acatgagcat atatagcttg cgcaaatcaa aactgtacag    8100
taggtgtgtg ttcaattcag aatagtattc tatttcgaat ttaaattaat aatacct tct    8160 gtagtaattt ctatattaga aaatttatac atacaaggag cactgttaat tagctagcta    8220
gctttatggg ttccactaat caatttatat ataataatgt gctaaactat acagcgtcca    8280 tgcatttta ttcttcatgc ctaattaatt tgattcacca ttaattaatt ctacgtacaa    8340
tgttcgaatg tgtgactata tatgctgcat ctgcagttct gcacctcatt cagtactaaa    8400
ttcaagttca ggttcattaa ttaattcact tattccttca tttttcactt ccagctaata    8460
caaaaccatg caaaaactca ttaactcagt gcaaaactat gcctggggca gcaaaacggc    8520
gttgactgaa ctttatggta tggaaaatcc gtccagccag ccgatggccg agctgtggat    8580
gggcgcacat ccgaaaagca gttcacgagt gcagaatgcc gccggagata tcgtttcact    8640
gcgtgatgtg attgagagtg ataaatcgac tctgctcgga gaggccgttg ccaaacgctt    8700
tggcgaactg cctttcctgt tcaaagtatt atgcgcagca cagccactct ccattcaggt    8760
tcatccaaac aaaacacaat tctgaaatcgg ttttgccaaa gaaatgccg caggtatccc    8820 gatggatgcc gccgagcgta actataaaga tcctaaccac aagccggagc tggttttgc    8880 gctgacgcct ttccttgcga tgaacgcgtt tcgtgaattt tccgagattg tctccctact    8940
ccagccggtc gcaggtgcac atccggcgat tgctcacttt ttacaacagc ctgatgccga    9000
acgtttaagc gaactgttcg ccagcctgtt gaatatgcag ggtgaagaaa atcccgcgc    9060 gctggcgatt ttaaaatcgg ccctcgatag ccagcagggt gaaccgtggc aaacgattcg    9120
tttaatttct gaattttacc cggaagacag cggtctgttc tccccgctat tgctgaatgt    9180
ggtgaaattg aaccctggcg aagcgatgtt cctgttcgct gaaacaccgc acgcttacct    9240
gcaaggcgtg gcgctggaag tgatggcaaa ctccgataac gtgctgcgtg cgggtctgac    9300
gcctaaatac attgatattc cggaactggt tgccaatgtg aaattcgaag ccaaaccggc    9360
taaccagttg tttgacccagc cggtgaaaca aggtgcagaa ctggacttcc cgattccagt    9420
ggatgatttt gccttctcgc tgcatgacct tagtgataaa gaaaccacca ttagccagca    9480
gagtgccgcc attttgttct gcgtcgaagg cgatgcaacg ttgtggaaag gttctcagca    9540
gttacagctt aaaccgggtg aatcagcgtt tattgccgcc aacgaatcac cggtgactgt    9600
caaaggccac ggccgtttag cgcgtgttta acaacaagctg taagagctta ctgaaaaaat    9660
taacatctct tgctaagctg ggagctctgt gtgtgttcag ttcaggcttc aggcttcaga    9720
gaagccaatg caaacagtgt cctgtaatcc agtaattaca gggcatatgt aatgtaatgt    9780
aatgtaatcc ctgatctata ttttgctaag tacgtgcgtg ctctcttacg accttctccc    9840
ccaaacagtt aatcagggga ataataattt cgtttgatgc acgtactgta tgtctgtatc    9900
tgtcactgta tcgtaggacc gtccatgtat aacaatttcc gttttggatg tggtaacaag    9960
ttaattggca cttaaatta tatttgtgat gatctgggag agtacctaat ctcaaaaact   10020
tgtggagatt atgttaggga gtagtgcaag aaatgtttta agacggcagc tgttatctca   10080
```

```
                                                      -continued tgagatattg ataatgatgt tgtctctgct gctgtcgcga tcgccaaatt atgctgtttt  10140
tttagattat accgaaatat gctgatggat acgtggtttt gatctgtggc cgttgcgaag  10200
taagcgcgat ttatttctgc aggcgttcga atcacgtttt actgttggcg gtagttactg  10260
cacggtgact gttcgacgaa atgccaaaac aacccgcagg ctgcagccag tcgacaagtg  10320
cggcggccgt cgcccgatcg cgcggctagc tagtagctgt cggcaccgcc ggttggttac  10380
ccgcaccacc gggccctcgc cgtcgccgtc ggccgtcctt gcgctgcacg gacgcgtcac  10440
gcgcactgcc gcctgcctgc ctttgcgctg tcgggcgggc gcgcgggcag aaagcgaccg  10500
cgcgcgcgga gggggcgcc ctcttccaca cgcagcgtag cggaggcggc actggcacgg  10560 aactccacc gagccgacgg gcccgcccgc ccggcggccg gccgcgccgc gccagcagct  10620
ggacgaacat ccgtgcacag cgcgcgcgca ggcgaggcgc ggcgcgacgt ggtgcttcgg  10680
ctcgcgtcct cgcgtacgta cgccgccacg gccaccaccg ccatcagtgt cgcgttttgc  10740
acttactcat actgaacact ggacagagca cgataagcag cggtgtttgt accgcccggc  10800
ccaagggacg gcagactcgc cggcagaaaa tcaaattaaa attgcatagt tgcaagtatt  10860
agcag                                                              10865
```